(12) United States Patent
Nasir et al.

(10) Patent No.: US 11,701,484 B2
(45) Date of Patent: Jul. 18, 2023

(54) AIRWAY DEVICE

(71) Applicant: ASHKAL DEVELOPMENTS LIMITED, Isle of Man (GB)

(72) Inventors: Muhammed Aslam Nasir, Isle of Man (GB); Andrew Honour, Isle of Man (GB); Ivan Crotaz, Isle of Man (GB)

(73) Assignee: ASHKAL DEVELOPMENTS LIMITED

( * ) Notice: Subject to any disclaimer, the term of this patent is extended or adjusted under 35 U.S.C. 154(b) by 228 days.

(21) Appl. No.: 16/954,147

(22) PCT Filed: Dec. 13, 2018

(86) PCT No.: PCT/GB2018/053622
§ 371 (c)(1),
(2) Date: Jun. 15, 2020

(87) PCT Pub. No.: WO2019/116041
PCT Pub. Date: Jun. 20, 2019

(65) Prior Publication Data
US 2021/0162155 A1 Jun. 3, 2021

(30) Foreign Application Priority Data
Dec. 13, 2017 (GB) ..................................... 1720733

(51) Int. Cl.
*A61M 16/04* (2006.01)
(52) U.S. Cl.
CPC .... *A61M 16/0431* (2014.02); *A61M 16/0409* (2014.02); *A61M 16/0443* (2014.02);
(Continued)

(58) Field of Classification Search
CPC ..... A61D 7/00; A61M 16/04; A61M 16/0409; A61M 16/0415; A61M 16/0431;
(Continued)

(56) References Cited

U.S. PATENT DOCUMENTS

| 478,582 A | 7/1892 | Ermold | 128/207.14 |
| 2,099,127 A | 11/1937 | Leech | 128/207.15 |

(Continued)

FOREIGN PATENT DOCUMENTS

| AU | B-52036/90 | 9/1990 | ............ A61M 16/04 |
| AU | B-45803/93 | 2/1994 | ............ A61M 16/04 |

(Continued)

OTHER PUBLICATIONS

Australian examination report issued in application No. 2018241061, dated Dec. 5, 2018 (4 pgs).
(Continued)

*Primary Examiner* — Colin W Stuart
*Assistant Examiner* — Matthew D Ziegler
(74) *Attorney, Agent, or Firm* — Hayes Soloway P.C.

(57) ABSTRACT

Laryngeal airway devices for human and veterinary use include an airway tube having a distal end and a proximal end. The distal end of the airway tube is provided with a pre-formed and non-inflatable peri-pharyngeal bowl. The peri-pharyngeal bowl has a posterior bowl portion having a back dorsal portion and a side wall extending around and depending from the periphery of the back dorsal portion to define an internal space, and further having a resiliently deformable flange extending laterally from the side wall of the back dorsal portion which defines an extended internal space, the resiliently deformable flange has inner and outer surfaces that extend to a circumferential edge.

24 Claims, 29 Drawing Sheets

(52) U.S. Cl.
CPC . *A61M 16/0415* (2014.02); *A61M 2205/0216* (2013.01); *A61M 2210/065* (2013.01); *A61M 2210/105* (2013.01); *A61M 2210/1046* (2013.01); *A61M 2250/00* (2013.01)

(58) Field of Classification Search
CPC .......... A61M 16/0443; A61M 16/0463; A61M 39/10; A61M 2039/082; A61M 2205/0216; A61M 2210/065; A61M 2210/1046; A61M 2210/105; A61M 2250/00
See application file for complete search history.

(56) References Cited

U.S. PATENT DOCUMENTS

| | | | |
|---|---|---|---|
| 3,443,564 A | 5/1969 | Oehmig | 128/351 |
| 3,616,799 A | 11/1971 | Sparks | 128/351 |
| 3,734,100 A | 5/1973 | Walker et al. | 128/351 |
| 3,968,800 A | 7/1976 | Vilasi | 128/343 |
| 3,995,643 A | 12/1976 | Merav | 128/351 |
| 4,509,514 A | 4/1985 | Brain | 128/207.15 |
| 4,846,791 A | 7/1989 | Hattler | A61M 25/0026 |
| 4,913,139 A | 4/1990 | Ballew | A61M 16/0488 |
| 4,919,126 A | 4/1990 | Baildon | 128/207.14 |
| 4,987,895 A | 1/1991 | Heimlich | A61M 16/0465 |
| 4,995,388 A | 2/1991 | Brain | 128/207.15 |
| 5,054,483 A | 10/1991 | Marten et al. | 128/207.14 |
| 5,174,283 A | 12/1992 | Parker | 128/200.26 |
| 5,181,505 A | 1/1993 | Lew | 128/200.26 |
| 5,241,956 A | 9/1993 | Brain | 128/207.15 |
| 5,249,571 A | 10/1993 | Brain | 128/207.14 |
| 5,259,371 A | 11/1993 | Tonrey | 128/200.26 |
| 5,282,464 A | 2/1994 | Brain | 128/207.15 |
| 5,285,778 A | 2/1994 | Mackin | 128/207.15 |
| 5,297,547 A | 3/1994 | Brain | 128/207.15 |
| 5,303,697 A | 4/1994 | Brain | 128/200.26 |
| 5,305,743 A | 4/1994 | Brain | 128/207.15 |
| 5,309,906 A | 5/1994 | LaBombard | 128/207.14 |
| 5,322,062 A | 6/1994 | Servas | 128/207.14 |
| 5,339,805 A | 8/1994 | Parker | 128/200.26 |
| 5,355,879 A | 10/1994 | Brain | 128/207.15 |
| 5,391,248 A | 2/1995 | Brain | 156/242 |
| 5,477,851 A | 12/1995 | Callaghan et al. | 128/207.15 |
| 5,584,290 A | 12/1996 | Brain | 128/207.15 |
| 5,605,149 A | 2/1997 | Warters | 128/207.14 |
| 5,618,267 A | 4/1997 | Palestrant | 605/53 |
| 5,623,921 A | 4/1997 | Kinsinger et al. | 128/200.26 |
| 5,632,271 A | 5/1997 | Brain | 128/207.15 |
| 5,653,229 A | 8/1997 | Greenberg | 128/207.15 |
| 5,655,519 A | 8/1997 | Alfery | 128/200.26 |
| 5,682,880 A | 11/1997 | Brain | 128/207.15 |
| 5,711,293 A | 1/1998 | Brain | 128/200.24 |
| 5,791,341 A | 8/1998 | Bullard | 128/207.15 |
| 5,827,243 A | 10/1998 | Palestrant | A61M 25/0023 |
| 5,853,004 A | 12/1998 | Goodman | 128/207.15 |
| 5,865,176 A | 2/1999 | O'Neil | 128/207.15 |
| 5,878,745 A | 3/1999 | Brain | 128/207.15 |
| 5,881,726 A | 3/1999 | Neame | 128/207.15 |
| 5,896,858 A | 4/1999 | Brain | 128/207.15 |
| 5,915,383 A | 6/1999 | Pagan | 128/207.15 |
| 5,921,988 A | 7/1999 | Legrand | 606/87 |
| 5,937,859 A | 8/1999 | Augustine et al. | 128/207.15 |
| 5,937,860 A | 8/1999 | Cook | 128/207.15 |
| 5,964,217 A | 10/1999 | Christopher | 128/200.26 |
| 5,976,072 A | 11/1999 | Greenberg | 600/120 |
| 5,979,445 A | 11/1999 | Neame et al. | 128/207.15 |
| 5,988,167 A | 11/1999 | Kamen | 128/207.15 |
| 6,003,514 A | 12/1999 | Pagan | 128/207.15 |
| 6,055,984 A | 5/2000 | Brain | 128/207.14 |
| 6,070,581 A | 6/2000 | Augustine et al. | 128/207.15 |
| 6,079,409 A | 6/2000 | Brain | 128/200.26 |
| D429,811 S | 8/2000 | Bermudez | D24/110.5 |
| 6,095,144 A | 8/2000 | Pagan | 128/207.15 |
| 6,152,136 A | 11/2000 | Pagan | 128/207.15 |
| 6,216,696 B1 | 4/2001 | van den Berg | 128/207.14 |
| 6,240,922 B1 | 6/2001 | Pagan | A61M 16/00 |
| 6,280,675 B1 | 8/2001 | Legrand | 264/262 |
| 6,311,688 B1 | 11/2001 | Augustine et al. | 128/200.26 |
| 6,318,367 B1 | 11/2001 | Mongeon | 128/207.15 |
| 6,422,239 B1 | 7/2002 | Cook | 128/207.15 |
| 6,439,232 B1 | 8/2002 | Brain | 128/207.15 |
| 6,474,332 B2 | 11/2002 | Arndt | 128/200.26 |
| 6,536,437 B1 | 3/2003 | Dragisic | 128/207.18 |
| 6,604,525 B2 | 8/2003 | Pagan | 128/207.15 |
| 6,631,720 B1 | 10/2003 | Brain | 128/207.14 |
| D482,118 S | 11/2003 | Dave et al. | D24/110 |
| 6,672,305 B2 | 1/2004 | Parker | 128/200.26 |
| 6,679,263 B2 | 1/2004 | Luchetti et al. | 128/207.15 |
| 6,698,430 B2 | 3/2004 | Van Landuyt | 128/207.15 |
| 6,705,318 B1 | 3/2004 | Brain | 128/207.14 |
| 6,705,321 B2 | 3/2004 | Cook | 128/207.15 |
| 6,705,322 B2 | 3/2004 | Chang | 128/207.15 |
| 6,792,948 B2 | 9/2004 | Brain | 128/207.14 |
| 6,799,574 B1 | 10/2004 | Collins | 128/207.15 |
| 6,827,710 B1 | 12/2004 | Mooney | A61B 17/3417 |
| 6,877,512 B2 | 4/2005 | Imai et al. | 128/207.15 |
| 6,918,388 B2 | 7/2005 | Brain | 128/200.26 |
| 6,918,391 B1 | 7/2005 | Moore | 128/842 |
| 6,971,382 B1 | 12/2005 | Corso | 128/200.26 |
| 7,004,169 B2 | 2/2006 | Brain | 128/207.14 |
| D518,572 S | 4/2006 | Nasir | D24/110.5 |
| D518,890 S | 4/2006 | Nasir | D24/110.5 |
| 7,040,312 B2 | 5/2006 | Alfery et al. | 128/200.26 |
| 7,040,322 B2 | 5/2006 | Fortuna | 128/207.15 |
| 7,047,973 B2 | 5/2006 | Chang | 128/207.15 |
| 7,096,868 B2 | 8/2006 | Tateo et al. | 128/207.15 |
| 7,097,802 B2 | 8/2006 | Brain | 264/255 |
| 7,134,431 B2 | 11/2006 | Brain | 128/200.26 |
| 7,140,368 B1 | 11/2006 | Collins | 128/207.14 |
| D542,675 S | 5/2007 | Luxton et al. | D9/749 |
| 7,263,998 B2 | 9/2007 | Miller | 128/207.15 |
| RE39,938 E | 12/2007 | Brain | 128/207.15 |
| 7,305,985 B2 | 12/2007 | Brain | 128/200.26 |
| 7,357,845 B2 | 4/2008 | Cook | 156/242 |
| 7,506,648 B2 | 3/2009 | Brain | 128/207.15 |
| D611,138 S | 3/2010 | Nasir | D24/110.5 |
| D615,188 S | 5/2010 | Nasir | D24/110.5 |
| D618,788 S | 6/2010 | Dubach | D24/110.5 |
| 7,762,261 B1 | 7/2010 | Fortuna | 128/207.14 |
| 7,784,464 B2 | 8/2010 | Cook | A61M 16/0409 |
| 7,806,119 B2 | 10/2010 | Nasir | 128/205.25 |
| 7,896,007 B2 | 3/2011 | Brain | 128/207.15 |
| 7,900,632 B2 | 3/2011 | Cook | 128/207.14 |
| 7,934,502 B2 | 5/2011 | Cook | A61M 16/04 |
| 8,001,964 B2 | 8/2011 | McDonald et al. | 128/200.26 |
| D650,520 S | 12/2011 | Timmermans | D27/163 |
| 8,091,242 B2 | 1/2012 | Teys et al. | 30/324 |
| 8,215,307 B2 | 7/2012 | Nasir | 128/207.15 |
| D665,495 S | 8/2012 | Nasir | D24/110.5 |
| D668,759 S | 10/2012 | Nasir | D24/110 |
| D693,920 S | 11/2013 | Miller | D24/110.5 |
| D710,990 S | 8/2014 | Brain | D24/110.5 |
| 8,809,682 B2 | 8/2014 | Hepfinger | H02G 9/065 |
| D716,937 S | 11/2014 | Brain | D24/110.5 |
| 9,265,905 B2 | 2/2016 | Aslam | 128/207.15 |
| D768,846 S | 10/2016 | Nasir | D24/110 |
| D791,305 S | 7/2017 | Poulsen | D24/110.5 |
| D809,125 S | 1/2018 | Kheong | D24/110 |
| 9,907,919 B2 | 3/2018 | Dubach | A61M 16/00 |
| 10,806,880 B2 | 10/2020 | Miller | A61M 16/04 |
| 2001/0015207 A1 | 8/2001 | Pagan | 128/207.15 |
| 2001/0025641 A1 | 10/2001 | Doane et al. | 128/207.15 |
| 2001/0027793 A1 | 10/2001 | Tielemans | 128/848 |
| 2002/0010417 A1 | 1/2002 | Bertram | 604/96.01 |
| 2002/0010617 A1 | 1/2002 | Hamaguchi et al. | 705/10 |
| 2002/0078961 A1 | 6/2002 | Collins | 128/207.15 |
| 2002/0103472 A1 | 8/2002 | Kramer | 604/507 |
| 2002/0108610 A1 | 8/2002 | Christopher | 128/200.26 |
| 2002/0112728 A1 | 8/2002 | Landuyt | 128/207.15 |
| 2002/0170556 A1 | 11/2002 | Gaitini | 128/200.14 |
| 2003/0037790 A1 | 2/2003 | Brain | 128/207.14 |
| 2003/0066532 A1 | 4/2003 | Gobel | 128/207.15 |
| 2003/0101998 A1 | 6/2003 | Zocca et al. | 128/207.15 |

(56) References Cited

U.S. PATENT DOCUMENTS

| | | | |
|---|---|---|---|
| 2003/0136413 A1 | 7/2003 | Brain et al. | 128/207.15 |
| 2003/0172925 A1 | 9/2003 | Zocca et al. | 128/202.22 |
| 2003/0172933 A1 | 9/2003 | Nimmo | 128/207.14 |
| 2003/0213492 A1 | 11/2003 | Alfery | A61M 16/04 |
| 2004/0020488 A1 | 2/2004 | Kniewasser | 128/204.18 |
| 2004/0020491 A1 | 2/2004 | Fortuna | 128/207.15 |
| 2004/0060564 A1 | 4/2004 | Brain | A61M 16/00 |
| 2004/0200479 A1 | 10/2004 | Chang | 128/207.14 |
| 2005/0016529 A1 | 1/2005 | Cook | 128/200.24 |
| 2005/0051173 A1 | 3/2005 | Brain | 128/207.14 |
| 2005/0051175 A1 | 3/2005 | Brain | 128/207.14 |
| 2005/0066975 A1 | 3/2005 | Brain | 128/207.15 |
| 2005/0081861 A1 | 4/2005 | Nasir | 128/207.14 |
| 2005/0103345 A1 | 5/2005 | Brain | 128/207.15 |
| 2005/0104255 A1 | 5/2005 | Mejlhede et al. | 264/328.1 |
| 2005/0199244 A1 | 9/2005 | Tateo | A61M 16/04 |
| 2005/0274383 A1 | 12/2005 | Brain | 128/207.15 |
| 2006/0076021 A1 | 4/2006 | Chang | A62B 9/06 |
| 2006/0081245 A1 | 4/2006 | Gould | 128/200.26 |
| 2006/0207601 A1 | 9/2006 | Nasir | 128/207.14 |
| 2007/0137651 A1 | 6/2007 | Glassenberg et al. | 128/207.15 |
| 2008/0099026 A1 | 5/2008 | Chang | 128/207.15 |
| 2008/0142017 A1 | 6/2008 | Brain | 128/207.15 |
| 2008/0236590 A1 | 10/2008 | Reissmann | 128/207.14 |
| 2008/0257356 A1 | 10/2008 | Swick | A61M 16/04 |
| 2008/0276932 A1 | 11/2008 | Bassoul | A61M 16/04 |
| 2008/0308109 A1 | 12/2008 | Brain | 128/207.14 |
| 2009/0090356 A1 | 4/2009 | Cook | 128/200.26 |
| 2009/0247868 A1 | 10/2009 | Chesnin | A61M 25/0032 |
| 2010/0059061 A1 | 3/2010 | Brain | 128/207.14 |
| 2010/0089393 A1 | 4/2010 | Brain | 128/203.12 |
| 2010/0126512 A1 | 5/2010 | Nasir | 128/207.14 |
| 2010/0147309 A1 | 6/2010 | Cuevas et al. | 128/207.14 |
| 2010/0242957 A1 | 9/2010 | Fortuna | 128/202.22 |
| 2010/0319704 A1 | 12/2010 | Nasir | 128/207.15 |
| 2011/0004197 A1 | 1/2011 | Sansoucy | A61M 25/0102 |
| 2011/0023890 A1 | 2/2011 | Baska | 128/207.15 |
| 2011/0120474 A1 | 5/2011 | Daugherty | A61M 16/04 |
| 2011/0226256 A1 | 9/2011 | Dubach | |
| 2011/0247619 A1 | 10/2011 | Formica | F16L 11/111 |
| 2011/0265799 A1 | 11/2011 | Lisogurski | 128/207.15 |
| 2011/0277772 A1 | 11/2011 | Nasir | 128/207.15 |
| 2012/0024292 A1 | 2/2012 | Sandmore et al. | 128/207.14 |
| 2013/0092172 A1 | 4/2013 | Nasir | 128/207.15 |
| 2013/0220332 A1 | 8/2013 | Baska et al. | 128/207.15 |
| 2013/0247917 A1 | 9/2013 | Brain | 128/207.15 |
| 2013/0269689 A1 | 10/2013 | Brain | A61M 16/04 |
| 2013/0324798 A1 | 12/2013 | Molnar et al. | 600/120 |
| 2014/0000624 A1 | 1/2014 | Miller | A61M 16/04 |
| 2014/0171855 A1 | 6/2014 | Mastri | A61M 39/1011 |
| 2015/0000672 A1 | 1/2015 | Jassell | 128/207.15 |
| 2015/0005743 A1 | 1/2015 | McCullough | A61M 25/1011 |
| 2015/0144134 A1 | 5/2015 | Dubach | A61M 16/0447 |
| 2015/0320962 A1 | 11/2015 | Bafile | A61M 16/0816 |
| 2016/0101254 A1 | 4/2016 | Hansen | A61M 16/0409 |
| 2016/0235934 A1 | 8/2016 | Poulsen | A61M 16/0409 |
| 2016/0317768 A1 | 11/2016 | Nasir et al. | A61M 16/0486 |
| 2016/0331918 A1 | 11/2016 | Nasir | A61M 16/0488 |
| 2017/0043111 A1 | 2/2017 | Hoftman | A61M 39/105 |
| 2017/0072154 A1 | 3/2017 | Hoftman | A61M 16/0816 |
| 2018/0177964 A1 | 6/2018 | Zhu | A61M 16/04 |
| 2018/0221051 A1 | 8/2018 | Durkin | A61B 17/3423 |

FOREIGN PATENT DOCUMENTS

| | | | |
|---|---|---|---|
| AU | 200076743 | 5/2001 | A61M 16/04 |
| CA | 1 324 551 | 11/1993 | A61M 16/04 |
| CA | 2 191 749 | 12/1995 | A61M 16/01 |
| CA | 2 346 248 | 4/2000 | A61M 16/04 |
| CN | 1 166 138 | 11/1997 | A61M 16/00 |
| CN | 1 236 326 | 11/1999 | A61M 16/04 |
| CN | 1 351 509 | 5/2002 | A61M 16/04 |
| CN | 103316412 | 9/2013 | A61M 16/01 |
| CN | 105251091 | 1/2016 | A61M 16/04 |
| DE | 42 33 933 | 4/1993 | H02N 2/00 |
| DE | 43 30 032 | 4/1994 | H02N 2/00 |
| DE | 195 00 550 | 7/1996 | A61M 16/04 |
| DE | 299 02 267 | 7/1999 | A61M 16/06 |
| DE | 201 00 176 | 5/2001 | A61M 16/01 |
| DE | 202 06 692 | 8/2002 | A61M 16/00 |
| DE | 102008052752 | 4/2010 | A61M 25/14 |
| EM | 000067210-0001 | 8/2003 | |
| EM | 000067210-0002 | 8/2003 | |
| EM | 000197124-0001 | 6/2004 | |
| EM | 000197124-0002 | 6/2004 | |
| EM | 000197124-0003 | 6/2004 | |
| EM | 000197124-0004 | 6/2004 | |
| EM | 000197124-0005 | 6/2004 | |
| EM | 000197124-0006 | 6/2004 | |
| EM | 000180757-0001 | 7/2004 | |
| EM | 000482195-0001 | 2/2006 | |
| EM | 000482195-0002 | 2/2006 | |
| EP | 0 277 797 | 8/1988 | A61M 16/04 |
| EP | 0 389 272 | 9/1990 | A61M 16/04 |
| EP | 0 448 878 | 10/1991 | A61M 16/04 |
| EP | 0 586 717 | 3/1994 | A61M 16/04 |
| EP | 0 794 807 | 9/1997 | A61M 16/00 |
| EP | 0 834 331 | 8/1998 | A61M 16/04 |
| EP | 0 857 492 | 8/1998 | A61M 16/04 |
| EP | 0 875 260 | 11/1998 | A61M 16/04 |
| EP | 0 884 061 | 12/1998 | A61M 16/04 |
| EP | 0 911 049 | 4/1999 | A61M 16/04 |
| EP | 0 935 971 | 8/1999 | A61M 16/04 |
| EP | 1 125 595 | 8/2001 | A61M 16/04 |
| EP | 1504870 | 2/2005 | |
| EP | 1 579 885 | 9/2005 | A61M 16/04 |
| EP | 1220701 | 3/2007 | A61M 16/04 |
| EP | 1169077 | 12/2007 | A61M 16/04 |
| EP | 1 875 937 | 1/2008 | A61M 16/04 |
| ES | 1 046 206 | 1/2000 | A61M 25/00 |
| FR | 2 094 264 | 1/1972 | C07C 31/00 |
| FR | 2 690 018 | 10/1993 | H02N 2/00 |
| FR | 2 760 186 | 9/1998 | A61F 2/30 |
| FR | 2 807 307 | 10/2001 | A47J 37/06 |
| FR | 2 827 482 | 1/2003 | A24B 1/10 |
| FR | 2 851 107 | 8/2004 | H04M 11/06 |
| GB | 1 402 255 | 8/1975 | A61M 25/00 |
| GB | 2 113 348 | 8/1983 | B06B 1/16 |
| GB | 2 128 561 | 5/1984 | B60R 19/54 |
| GB | 2 168 256 | 6/1986 | A61M 16/04 |
| GB | 2 249 959 | 5/1992 | A61M 16/04 |
| GB | 2 267 034 | 11/1993 | A61M 25/02 |
| GB | 2 285 765 | 7/1995 | A61M 16/04 |
| GB | 2 317 342 | 3/1998 | A61M 16/04 |
| GB | 2 319 182 | 5/1998 | A61M 16/04 |
| GB | 2 323 292 | 9/1998 | A61M 16/04 |
| GB | 2 326 009 | 12/1998 | A61M 16/04 |
| GB | 2 330 312 | 4/1999 | A61M 16/04 |
| GB | 2 337 020 | 11/1999 | B29D 31/00 |
| GB | 2 359 996 | 9/2001 | A61M 16/04 |
| GB | 2 364 644 | 2/2002 | A61M 16/04 |
| GB | 2 373 188 | 9/2002 | A61M 16/04 |
| GB | 2 393 399 | 3/2004 | A61M 16/04 |
| GB | 2 404 863 | 2/2005 | A61M 16/04 |
| GB | 2 413 963 | 11/2005 | A61M 16/04 |
| GB | 2438799 | 12/2007 | A61M 16/04 |
| GB | 2 465 453 | 5/2010 | A61M 16/04 |
| GB | 2479823 | 10/2011 | A61M 16/12 |
| GB | 2481538 | 12/2011 | A61M 16/04 |
| GB | 2521375 | 6/2015 | A61M 16/04 |
| GB | 2546167 | 7/2017 | A61M 16/04 |
| IE | 922073 | 12/1993 | A61M 16/00 |
| IT | 1224077 | 9/1990 | |
| JP | 3-236858 | 10/1991 | A61M 16/04 |
| JP | 6/277286 | 10/1994 | A61M 16/04 |
| JP | 2706567 | 1/1998 | A61B 1/00 |
| JP | 2007-509154 | 4/2007 | A61K 31/4409 |
| JP | 2015518760 | 7/2015 | |
| TW | 224047 | 11/2004 | B29C 45/76 |
| WO | WO91/12844 | 9/1991 | A61M 16/04 |
| WO | WO 94/17848 | 8/1994 | A61M 16/04 |
| WO | WO 95/09665 | 4/1995 | A61M 16/04 |
| WO | WO 97/12640 | 4/1997 | A61M 16/00 |
| WO | WO 98/06276 | 2/1998 | A23L 1/30 |

(56) References Cited

FOREIGN PATENT DOCUMENTS

| WO | WO 98/24498 | 6/1998 | ............ A61M 16/04 |
|---|---|---|---|
| WO | WO 98/50096 | 11/1998 | ............ A61M 16/00 |
| WO | WO 99/24101 | 5/1999 | ............ A61M 16/00 |
| WO | WO 99/44665 | 9/1999 | ............ A61M 16/04 |
| WO | WO 00/09189 | 2/2000 | ............ A61M 16/04 |
| WO | WO 00/30706 | 6/2000 | ............ A61M 16/04 |
| WO | WO 00/61213 | 10/2000 | ............ A61M 16/04 |
| WO | WO0112844 | 2/2001 | ............... C12Q 1/34 |
| WO | WO 01/13980 | 3/2001 | ............ A61M 16/04 |
| WO | WO2011131974 | 10/2001 | ............ A61M 16/04 |
| WO | WO 0197890 | 12/2001 | ............ A61M 16/00 |
| WO | WO 02/32490 | 4/2002 | ............ A61M 16/04 |
| WO | WO 03/020340 | 3/2003 | ............ A61M 16/04 |
| WO | WO 03018094 | 3/2003 | ............ A61M 16/04 |
| WO | WO 2004/016308 | 2/2004 | ............ A61M 16/04 |
| WO | WO2004/089453 | 10/2004 | |
| WO | WO 2005/016427 | 2/2005 | ............ A61M 16/04 |
| WO | WO2005027999 | 3/2005 | |
| WO | WO 2005/041864 | 5/2005 | ............ A61K 31/415 |
| WO | WO2005099800 | 10/2005 | ............ A61M 16/04 |
| WO | WO2006/125986 | 11/2006 | ............ A61M 16/04 |
| WO | WO 2009/129081 | 10/2009 | ............ A61M 16/04 |
| WO | WO2009142821 | 11/2009 | ............... A61B 1/31 |
| WO | WO2011161473 | 12/2011 | ............ A61M 16/04 |
| WO | WO2012/049448 | 4/2012 | ............ A61M 16/04 |
| WO | WO2014058840 | 4/2014 | ............ A61M 16/00 |
| WO | WO2014159522 | 10/2014 | ............ A61M 16/04 |
| WO | WO2015092404 | 6/2015 | ............ A61M 16/04 |

OTHER PUBLICATIONS

"The Development of the Laryngeal Mask—a Brief History of the Invention, Early Clinical Studies and Experimental Work from Which the Laryngeal Mask Evolved" A.I.J. Brain, European Journal of Anesthesiology, 1991, Supplement 4, pp. 5-17.
Chinese Official Action issued in application No. 201480074768.1, dated Jun. 5, 2017 with machine translation (21 pages).
Combined Search and Examination Report issued in corresponding application No. GB1110775.2, dated Oct. 18, 2011 (8 pgs).
Combined Search and Examination Report issued in corresponding application No. GB0718849.3, dated Oct. 29, 2007 (4 pgs).
Combined Search and Examination Report issued in corresponding application No. GB0502519.2, dated Sep. 13, 2005 (6 pgs).
Combined Search and Examination Report issued in corresponding application No. GB1019839.8, dated Dec. 1, 2010 (2 pgs).
Combined Search and Examination Report issued in corresponding application No. GB 0418050.1, dated Nov. 29, 2004 (7 pgs).
Combined Search and Examination Report issued in related application No. GB1301478.2, dated May 23, 2013 (5 Pgs).
Combined Search and Examination Report issued in application No. GB16213121.7, dated May 4, 2017 (5 pgs).
European Patent Office Examination Report Issued In Corresponding Application No. 14824070.8, dated Apr. 24, 2017 (9 Pages).
European Patent Office Examination Report and Search Issued In Corresponding Application No. 19156241.2, dated May 13, 2020 (4 Pages).
Examination Report issued in corresponding application No. 09 756 353.0-1257, dated Aug. 17, 2012 (5 pgs).
Extended European Search Report and Written Opinion issued in corresponding EPO application No. 07019251.3, dated Feb. 1, 2008 (8 pgs).
European examination report issued in application No. 14824070.8, dated f, 2018 (5 pgs).
European Search Report issued in application No. 19156241.2, dated Jun. 14, 2019 (6 pgs).
First Office Action issued in corresponding Chinese application No. 200480023382.4, dated Aug. 22, 2008 (15 Pgs).
Further examination as result of telephone conversation with examiner issued in corresponding EPO application No. 03 787 902.0 (1 pg).

Great Britain Combined Search and Examination Report issued in application No. GB 1322330.0, dated May 20, 2015(8 pgs).
Great Britain Combined Search and Examination Report issued in application No. GB 1322328.4, dated Feb. 26, 2015 (8 pgs).
Great Britain Combined Search and Examination Report issued in application No. GB1800914.2, dated Feb. 2, 2018 (6 pgs).
Great Britain Combined Search and Examination Report Issued In Corresponding Application No. GB1621321.7, dated May 4, 2017 (5 Pages).
Great Britain Examination Report Issued In Corresponding Application No. GB1322330.0, dated Mar. 8, 2016 (3 Pages).
Great Britain Search and Examination Report issued in application No. GB1820348.9, dated May 31, 2019 (7 Pgs).
Great Britain Search and Examination Report issued in application No. GB1720733.3, dated May 31, 2018 (9 Pgs).
International Preliminary Report on Patentability issued in application No. PCT/GB2014/053744, dated Jun. 21, 2016(9 pgs).
International Preliminary Report on Patentability issued in application No. PCT/GB2014/053745, dated Jun. 21, 2016(9 pgs).
International Search Authority issued in corresponding PCT application PCT/GB03/03577 dated Dec. 9, 2003 (5 pgs).
International Search Report and Written Opinion issued in application PCT/GB2018/053622, dated Feb. 12, 2019 (11 pgs).
International Preliminary Report on Patentability issued in application PCT/GB2018/053622, dated Jun. 16, 2020 (18 pgs).
International Search Report and Written Opinion issued in Applicant's corresponding UK Patent Application Serial No. GB0817776.8, dated Jan. 8, 2009 (6 pgs).
International Search Report and Written Opinion issued in application No. PCT/GB2014/053745, dated Mar. 11, 2015 (14 pgs).
International Search Report and Written Opinion issued in application No. PCT/GB2014/053744, dated Jul. 14, 2015 (15 pgs).
International Search Report and Written Opinion issued in corresponding application No. PCT/GB2011/051203, dated Jul. 12, 2011 (13 pgs).
International Search Report and Written Opinion issued in corresponding application No. PCT/GB2011/051203, dated Dec. 7, 2011 (15 pgs).
International Search Report and Written Opinion issued in corresponding PCT application No. PCT /GB2009/051574, dated Jun. 7, 2010 (28 pgs).
International Search Report and Written Opinion issued in related application No. PCT/GB2013/050180, dated May 7, 2013 (13 pgs).
International Search Report issued in corresponding PCT application PCT/GB03/03577 dated Aug. 14, 2003 (9 pgs).
Invitation to Pay Additional Fees with International Search Report issued in corresponding application No. PCT/GB2004/003481, dated Nov. 12, 2004 (8 pgs).
Japanese Office Action (no translation) issued in related application No. 2012-38633, dated Apr. 23, 2013 (2 pgs).
Japanese Office Action (no translation) issued in related application No. 2019-114088, dated Jun. 12, 2020 (12 pgs).
Letter from IP Australia regarding third party application for re-examination dated Sep. 21, 2011 involving corresponding application No. 2008207412 (2 pgs).
Merriam-Webster Lumen Definition (Year: 2019) (1 pg).
Notice for Reasons for Rejection issued in corresponding Japanese application No. 2006/523053, dated Nov. 8, 2010, with English translation (4 pgs).
Notice of Allowance issued in U.S. Appl. No. 13/805,956, dated Dec. 21, 2015 (26 pgs).
Notice of Allowance issued in U.S. Appl. No. 14/315,141, dated Nov. 13, 2015 (36 pgs).
Notice of Allowance issued in U.S. Appl. No. 14/315,149, dated Mar. 11, 2016 (42 pgs).
Notice of Allowance issued in U.S. Appl. No. 14/315,149, dated Aug. 30, 2016 (16 pgs).
Notice of Allowance issued in U.S. Appl. No. 14/375,109, dated Feb. 9, 2018 (8 pgs).
Notice of Allowance issued in U.S. Appl. No. 29/428,284, dated Mar. 8, 2016 (17 pgs).
Notice of Allowance issued in U.S. Appl. No. 29/548,655, dated Oct. 11, 2018 (28 pgs).

(56) References Cited

OTHER PUBLICATIONS

Notice of Allowance issued in U.S. Appl. No. 29/676,952, dated Nov. 5, 2019 (5 pgs).
Notice of Allowance issued in related U.S. Appl. No. 13/403,806, dated Mar. 12, 2014 (16 pgs).
Notice of Allowance issued in related U.S. Appl. No. 29/416,561, dated May 9, 2014 (7 pgs).
Notice of Allowance issued in related U.S. Appl. No. 29/449,900, dated Jul. 24, 2013 (11 pgs).
Notice of Allowance issued in related U.S. Appl. No. 29/407,461, dated Jun. 12, 2013 (26 pgs).
Office Action issued in U.S. Appl. No. 12/627,844, dated Jan. 27, 2017 (28 pgs).
Office Action issued in U.S. Appl. No. 12/627,844, dated May 5, 2016 (33 pgs).
Office Action issued in U.S. Appl. No. 12/627,844, dated Sep. 17, 2015 (26 pgs).
Office Action issued in U.S. Appl. No. 14/375,109, dated Aug. 10, 2016 (49 pgs).
Office Action issued in U.S. Appl. No. 14/375,109, dated Dec. 15, 2017 (17 pgs).
Office Action issued in U.S. Appl. No. 14/375,109, dated Nov. 7, 2016 (17 pgs).
Office Action issued in U.S. Appl. No. 15/106,239, dated Jul. 18, 2019 (18 pgs).
Office Action issued in U.S. Appl. No. 15/106,239, dated Oct. 28, 2019 (21 pgs).
Office Action issued in U.S. Appl. No. 15/106,243, dated Aug. 2, 2019 (18 pgs).
Office Action issued in U.S. Appl. No. 15/106,243, dated Jan. 10, 2020 (23 pgs).
Office Action issued in U.S. Appl. No. 15/106,243, dated Jul. 7, 2020 (30 pgs).
Office Action issued in U.S. Appl. No. 29/353,658 dated Aug. 19, 2011 (10 pgs).
Office Action issued in U.S. Appl. No. 29/428,284, dated Mar. 19, 2015 (6 pgs).
Office Action issued in U.S. Appl. No. 29/428,284, dated Nov. 10, 2015 (5 pgs).
Office Action issued in U.S. Appl. No. 29/512,931, dated Mar. 8, 2016 (8 pgs).
Office Action issued in U.S. Appl. No. 29/512,931, dated Nov. 23, 2015 (20 pgs).
Office Action issued in U.S. Appl. No. 29/512,932, dated Mar. 8, 2016 (8 pgs).
Office Action issued in U.S. Appl. No. 29/512,932, dated Nov. 19, 2015 (19 pgs).
Office Action issued in U.S. Appl. No. 29/548,655, dated Mar. 8, 2018, (7 pgs).
Office Action issued in U.S. Appl. No. 29/676,952, dated Jun. 6, 2019 (22 pgs).
Office Action issued in related U.S. Appl. No. 12/627,844, dated Feb. 28, 2014 (22 pgs).
Office Action issued in related U.S. Appl. No. 12/627,844, dated Oct. 23, 2014 (38 pgs).
Office Action issued in related U.S. Appl. No. 13/130,555, dated Jun. 20, 2014 (36 pgs).
Office Action issued in related U.S. Appl. No. 13/403,806, dated Apr. 25, 2013 (6 pgs).
Office Action issued in related U.S. Appl. No. 13/403,806, dated Aug. 15, 2013 (45 pgs).
Office Action issued in related U.S. Appl. No. 29/428,284, dated Oct. 6, 2014 (66 pgs).
Office Action issued in related U.S. Appl. No. 29/475,489, dated Jun. 20, 2014 (25 pgs).
Office Action issued in related U.S. Appl. No. 29/475,489, dated Dec. 4, 2014 (13 pgs).
Official Action issued in U.S. Appl. No. 14/375,109, dated Jun. 23, 2017 (10 pgs).
PCT International Search Report, PCT Application Serial No. PCT/GB2008/050880, dated Jan. 14, 2009 (20 pgs).
UK Search Report issued in corresponding application No. GB1110775.2, dated Oct. 18, 2011 (8 pgs).
U.S. Official Action dated Feb. 14, 2013, issued in U.S. Appl. No. 29/407,461 (21 pgs).
U.S. Appl. No. 10/983,199, filed Nov. 5, 2004.
U.S. Appl. No. 10/568,362, filed Feb. 14, 2006.
U.S. Appl. No. 12/627,844, filed Nov. 30, 2009.
U.S. Appl. No. 29/353,658, filed Jan. 12, 2010.
U.S. Appl. No. 12/680,731, filed Mar. 29, 2010.
U.S. Appl. No. 12/859,169, filed Aug. 18, 2010.
U.S. Appl. No. 13/130,555, filed May 20, 2011.
U.S. Appl. No. 29/402,009, filed Sep. 19, 2011.
U.S. Appl. No. 29/407,461, filed Nov. 29, 2011.
U.S. Appl. No. 13/403,806, filed Feb. 23, 2012.
U.S. Appl. No. 29/416,561, filed Mar. 23, 2012.
U.S. Appl. No. 29/428,284, filed Jul. 27, 2012.
U.S. Appl. No. 13/805,956, filed Dec. 20, 2012.
U.S. Appl. No. 29/449,900, filed Mar. 15, 2013.
U.S. Appl. No. 29/475,489, filed Dec. 3, 2013.
U.S. Appl. No. 14/315,141, filed Jun. 25, 2014.
U.S. Appl. No. 14/315,149, filed Jun. 25, 2014.
U.S. Appl. No. 14/375,109, filed Jul. 28, 2014.
U.S. Appl. No. 29/512,931, filed Dec. 23, 2014.
U.S. Appl. No. 29/512,932, filed Dec. 23, 2014.
U.S. Appl. No. 29/548,655, filed Dec. 15, 2015.
U.S. Appl. No. 15/106,239, filed Jun. 17, 2016.
U.S. Appl. No. 15/106,243, filed Jun. 17, 2016.
U.S. Appl. No. 29/731,615, filed Apr. 16, 2020.
U.S. Appl. No. 12/627,844, filed Nov. 30, 2009, Nasir.
U.S. Appl. No. 29/428,284, filed Jul. 27, 2012, Nasir et al.
U.S. Appl. No. 14/315,149, filed Jun. 25, 2014, Nasir.
U.S. Appl. No. 14/375,109, filed Jul. 28, 2014, Jassell et al.
U.S. Appl. No. 29/512,931, filed Dec. 23, 2014, Nasir et al.
U.S. Appl. No. 29/512,932, filed Dec. 23, 2014, Nasir et al.
U.S. Appl. No. 29/548,655, filed Dec. 15, 2015, Miller et al.
U.S. Appl. No. 15/106,243, filed Jun. 17, 2016, Nasir et al.
U.S. Appl. No. 15/106,239, filed Jun. 17, 2016, Nasir et al.
Australian Notice of Acceptance issued in application No. 2018241061, dated Feb. 13, 2019 (4 pgs).
U.S. Official Action dated Mar. 2, 2022, issued in U.S. Appl. No. 16/833,458 (24 pgs).
Decision dated Feb. 19, 2019 issued in Japanese Application Serial No. 2016-541075 (6 pgs).
Official Action dated Aug. 13, 2018 issued in Japanese Application Serial No. 2016-541075 (10 pgs).
Official Action dated Jun. 28, 2018 issued in Chinese Application Serial No. 201810691201.9 (15 pgs).
Search dated Jun. 1, 2020 issued in Chinese Application Serial No. 2018106912019 (3 pgs).
India Official Action issued in related Indian Patent Application. 202118007650, dated Mar. 9, 2022 (5 pages).
Official Action dated Jan. 29, 2018 issued in Chinese Application Serial No. 201480072822.9 (15 pgs).
Chinese Official Action issued in related application No. 201880079916.7, dated Aug. 30, 2022, with translation, 11 pgs.
European Search Report issued in related application No. 22172616.9, dated Jul. 26, 2022, 8 pgs.
Japanese Official Action issued in related application No. 2020-532021, dated Aug. 29, 2022, with translation, 6 pgs.
Official Action issued in related U.S. Appl. No. 29/698,547, dated Jan. 18, 2023, 6 pages.

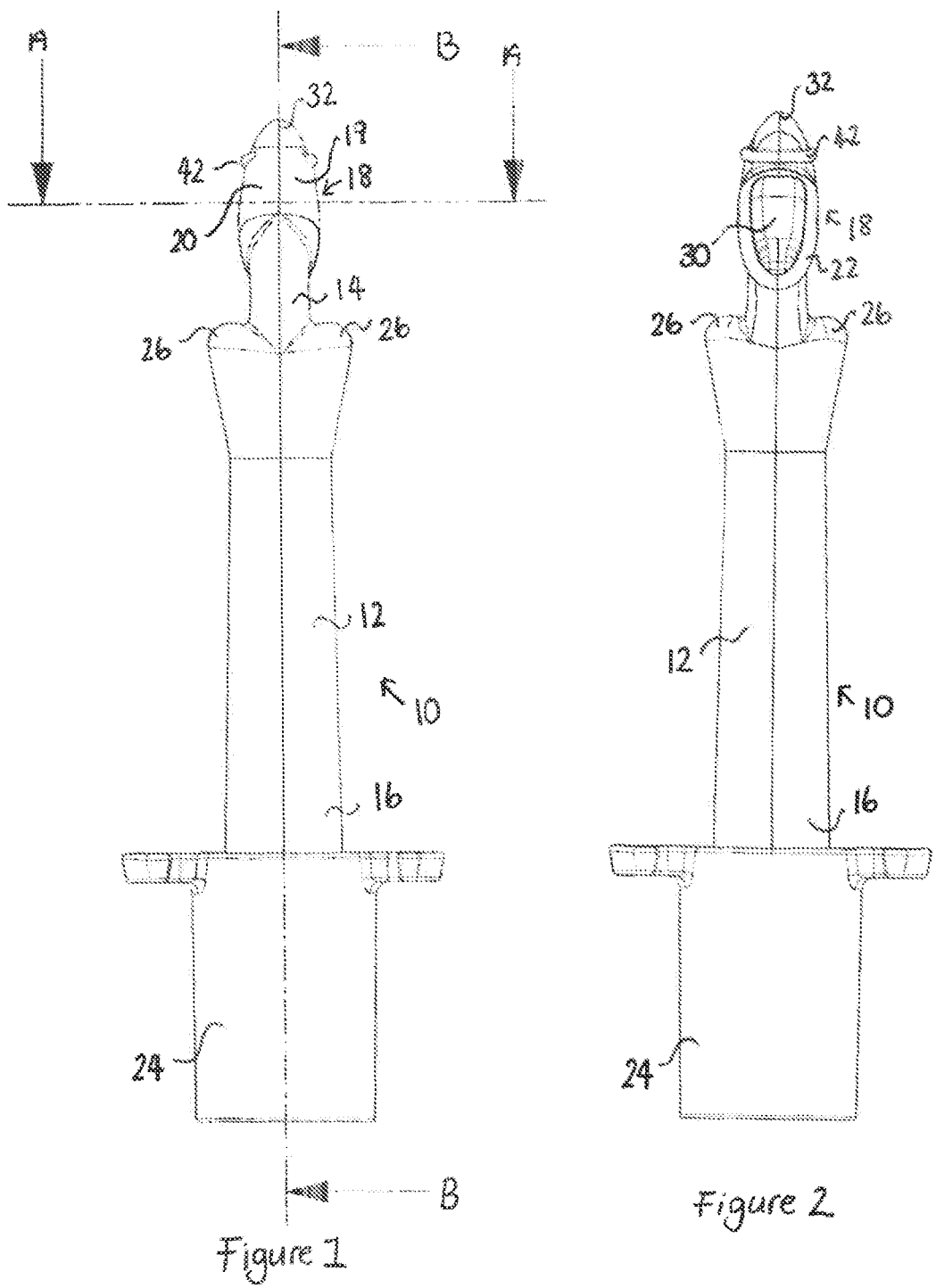

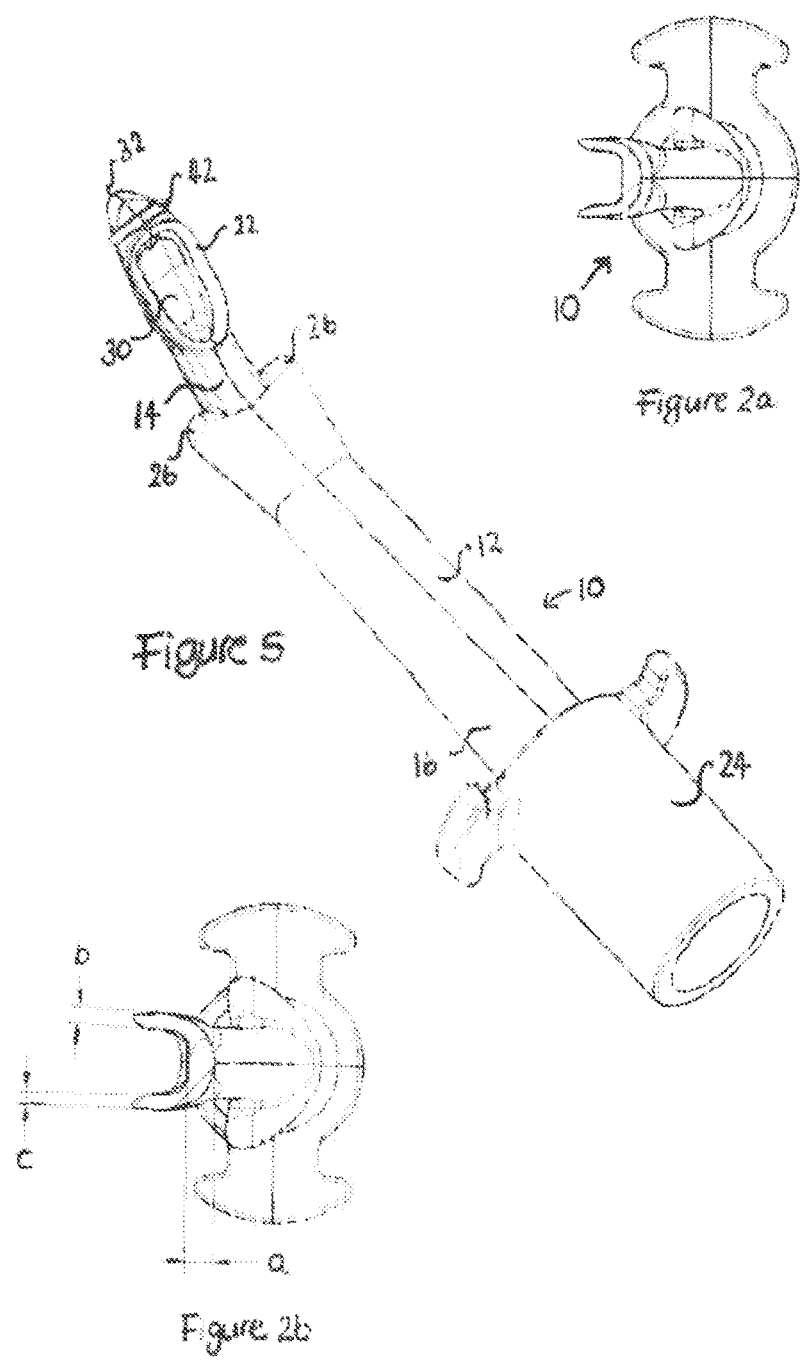

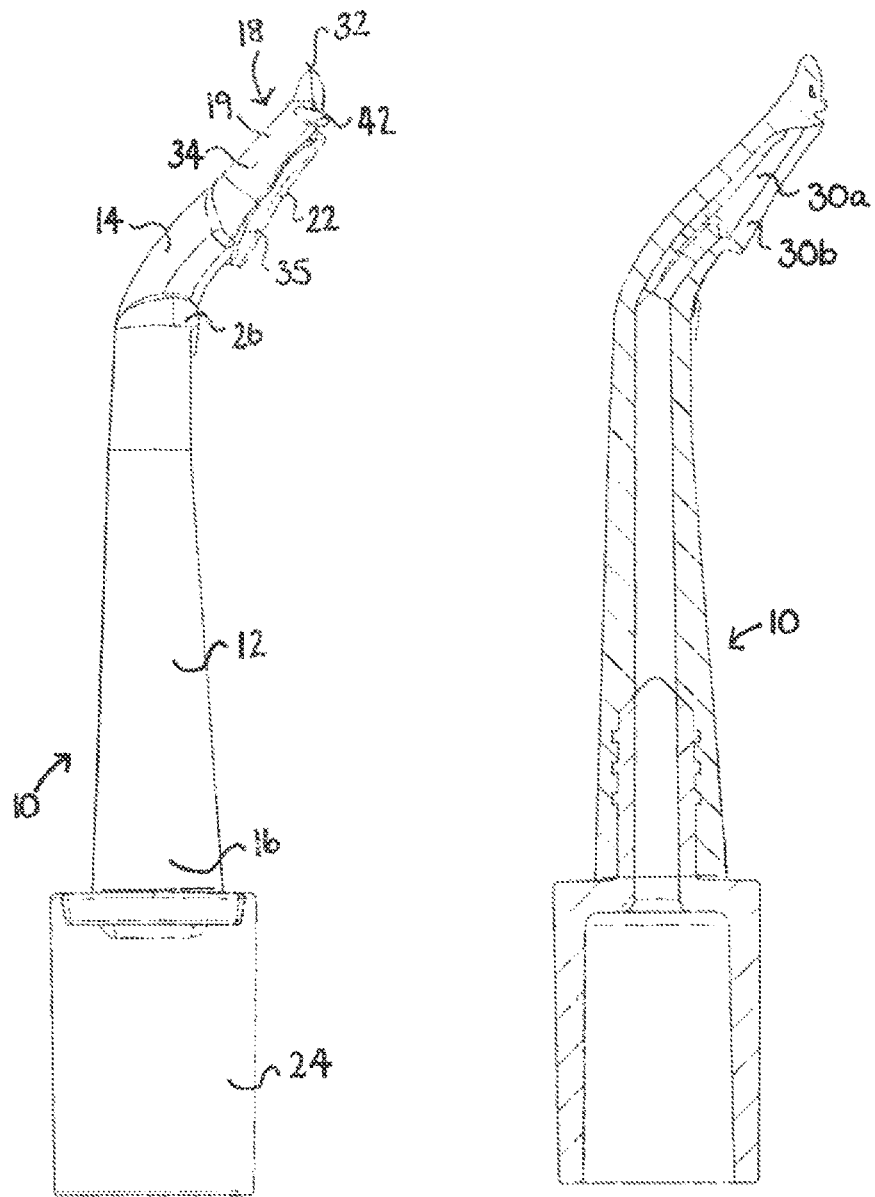

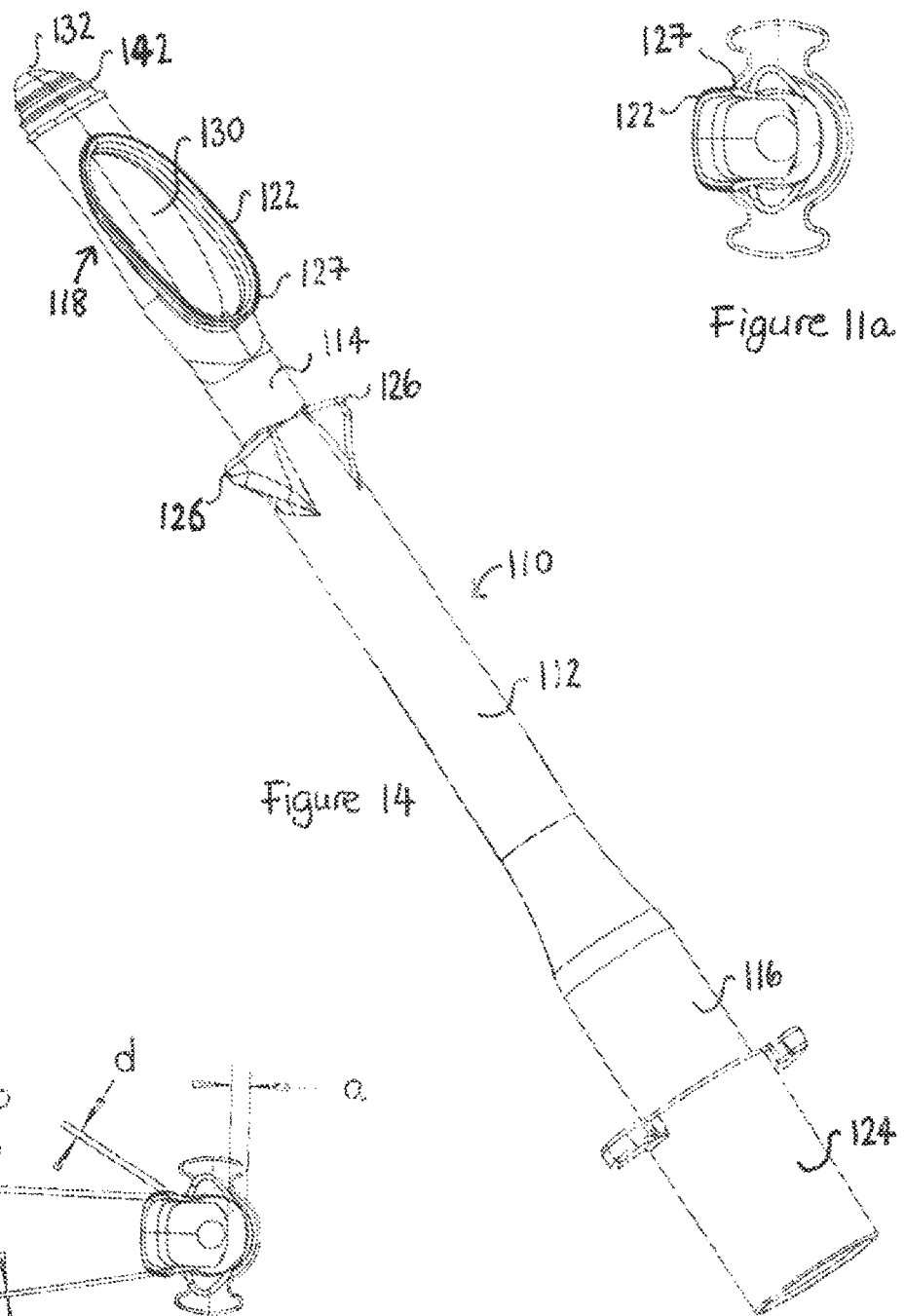

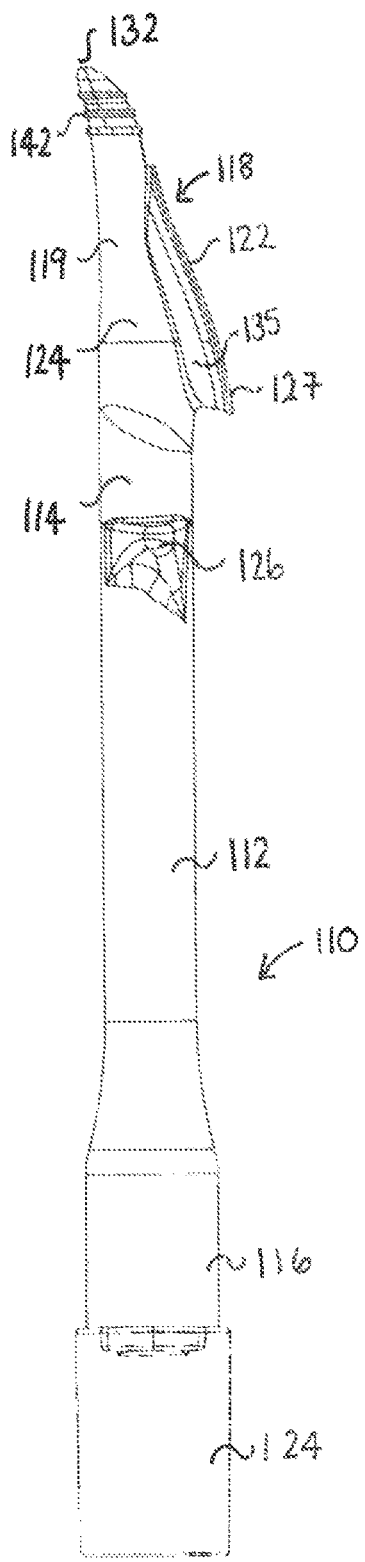
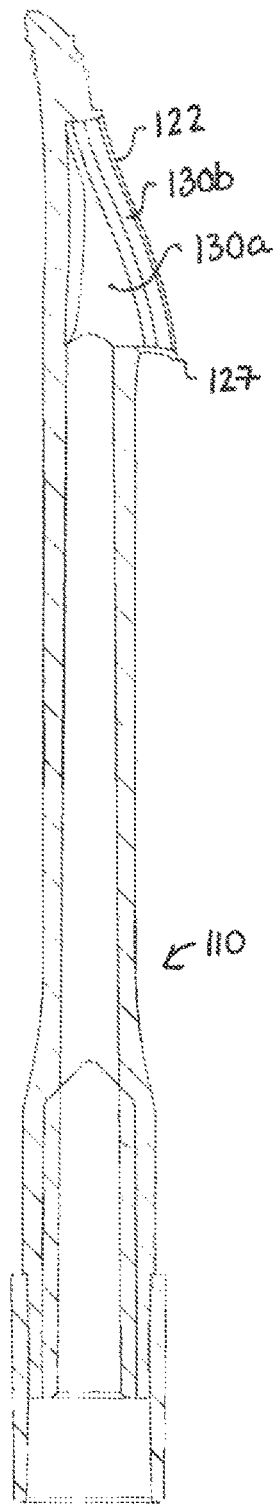
Figure 12
Figure 13

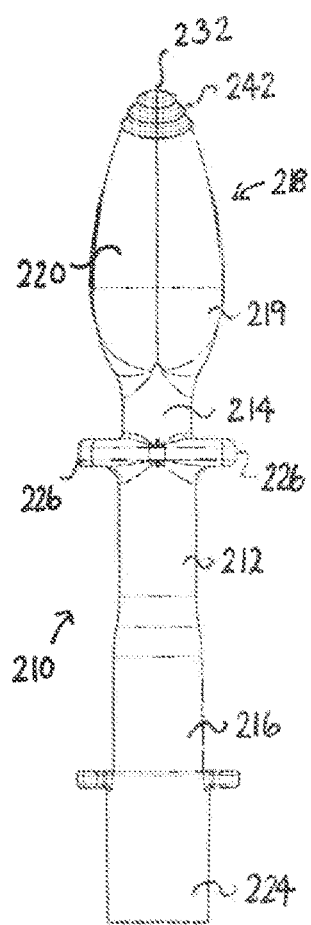
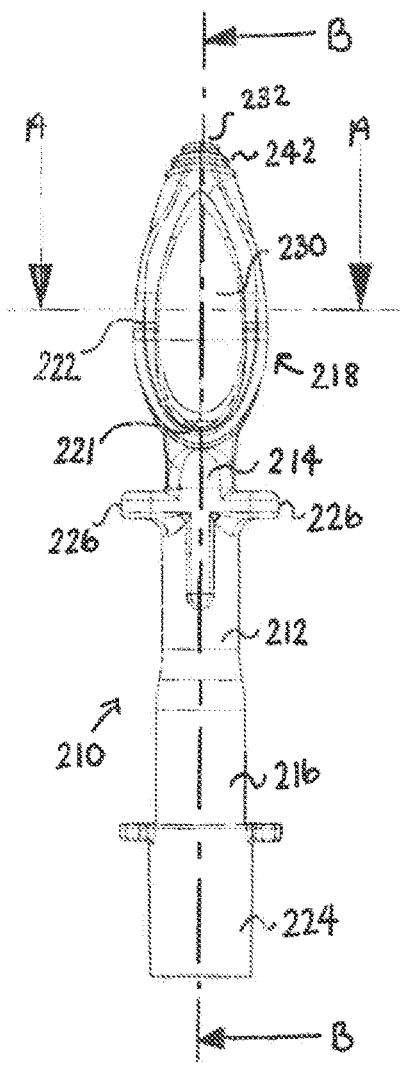
Figure 19
Figure 20

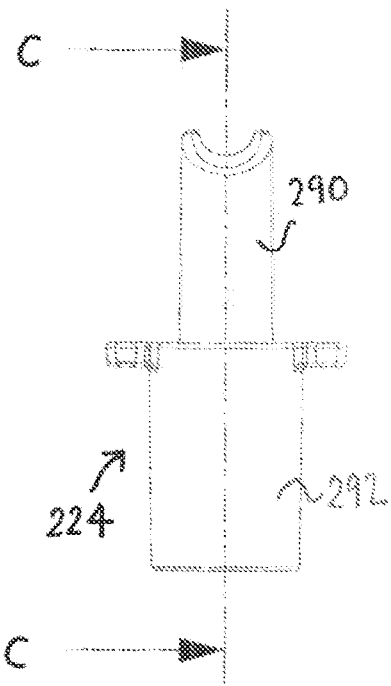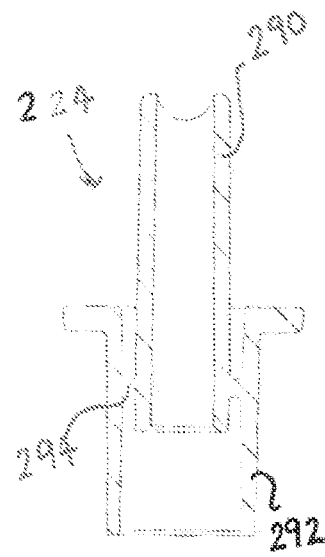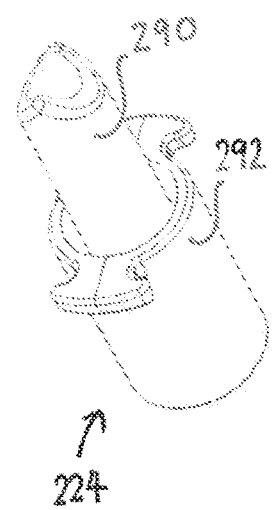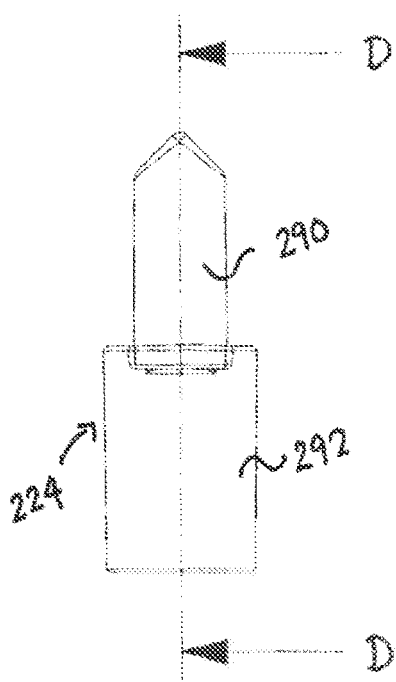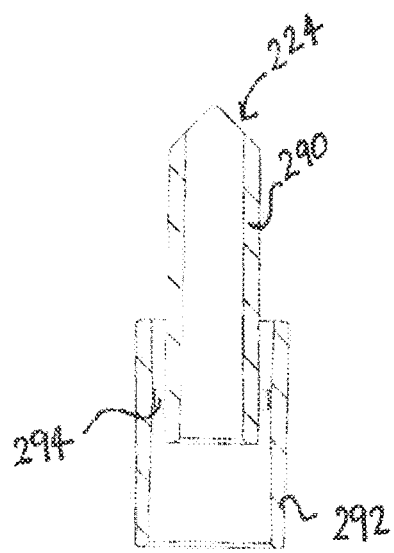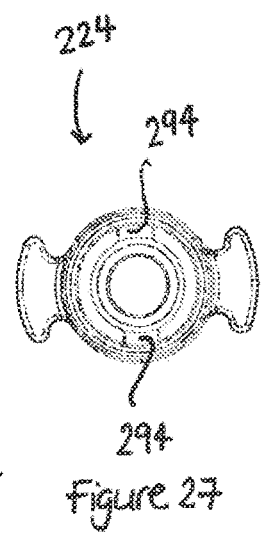
Figure 24
Figure 24a
Figure 26
Figure 25
Figure 25a
Figure 27

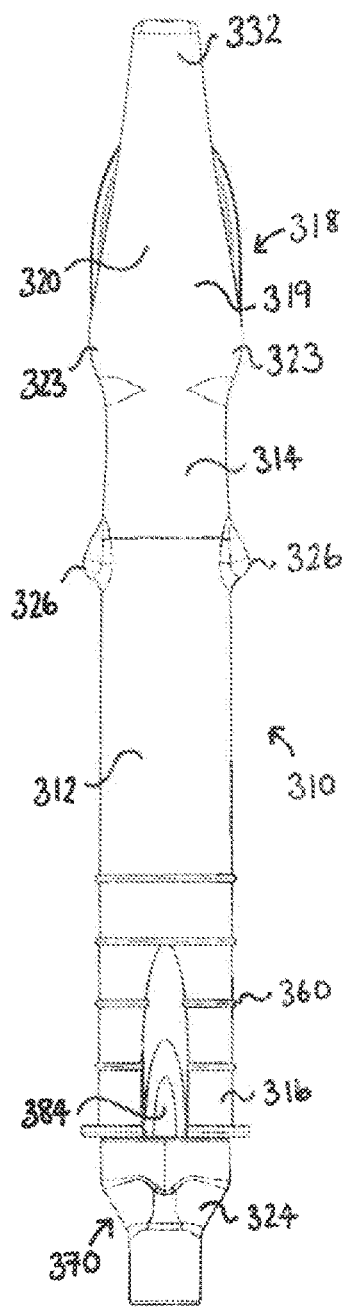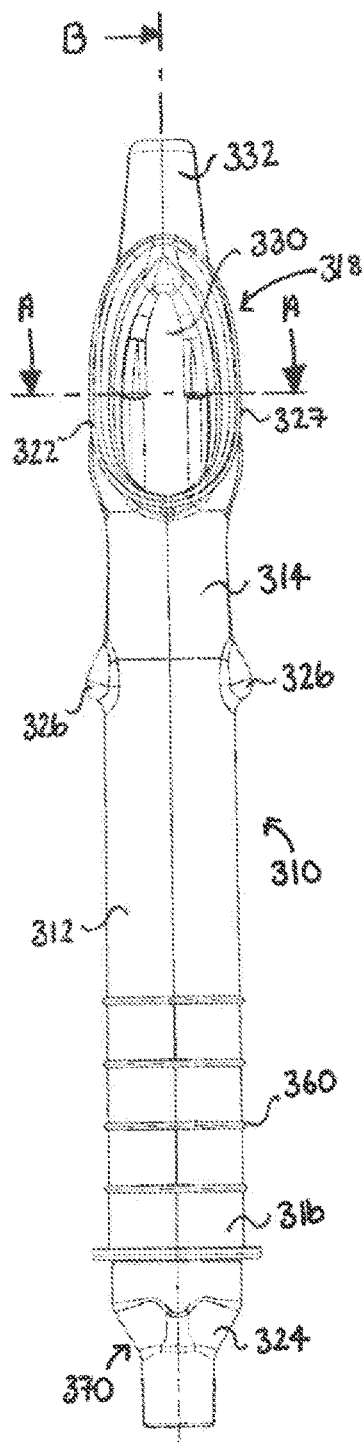
Figure 28
Figure 29

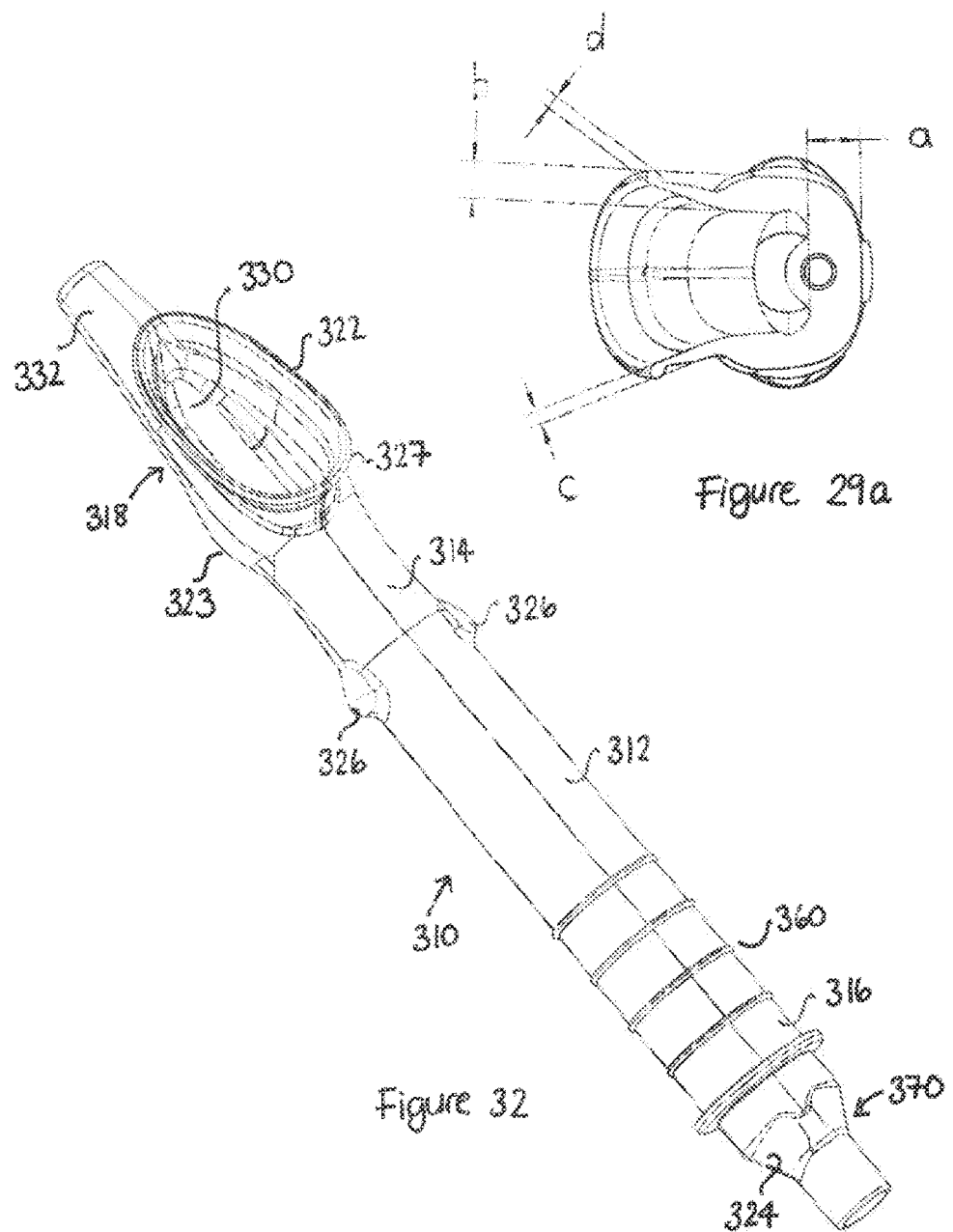

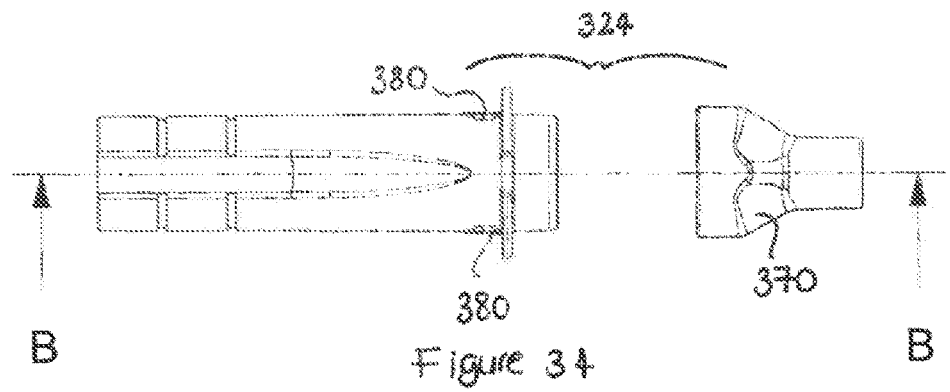
Figure 34
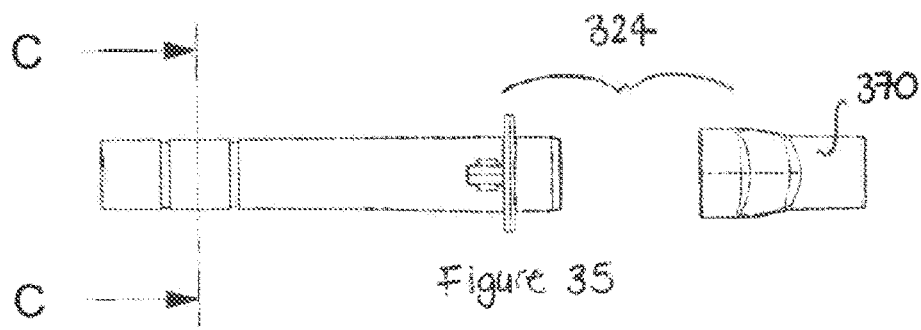
Figure 35
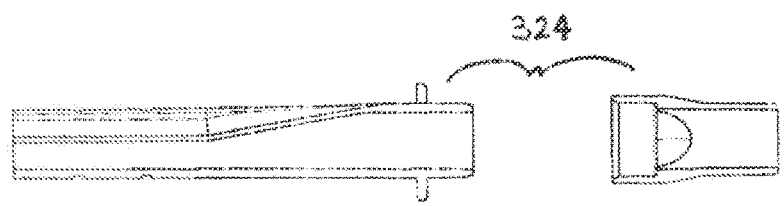
Figure 36
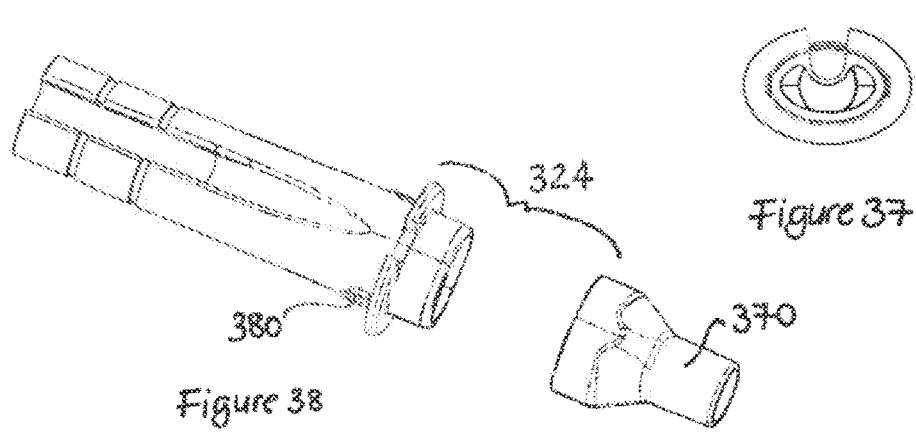
Figure 37
Figure 38

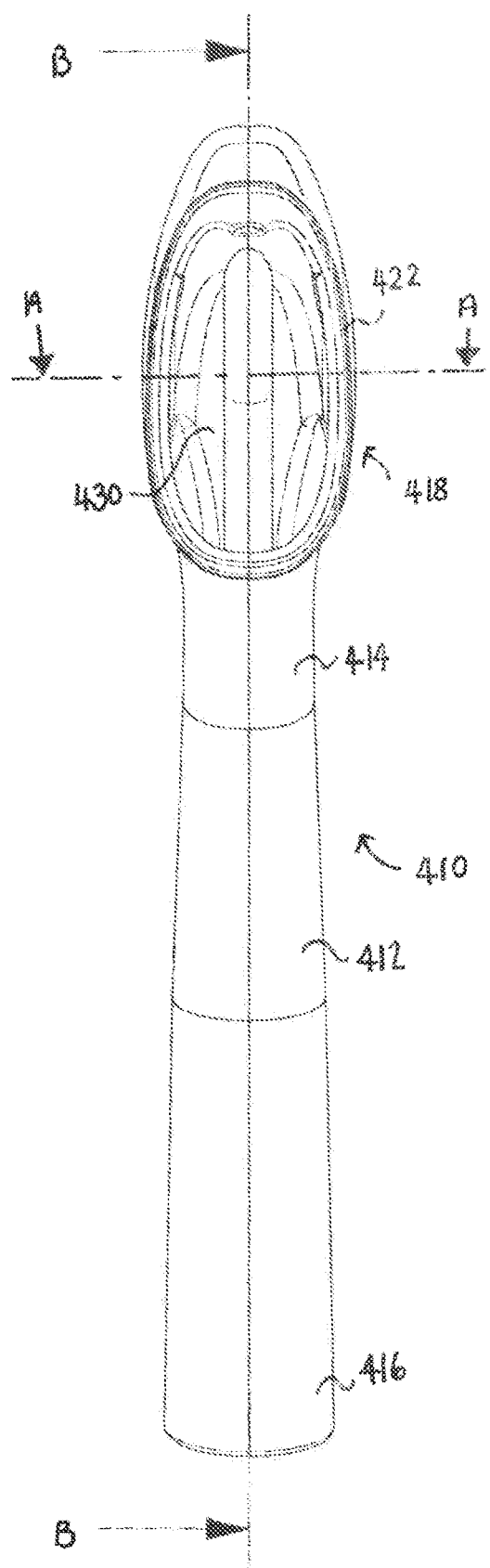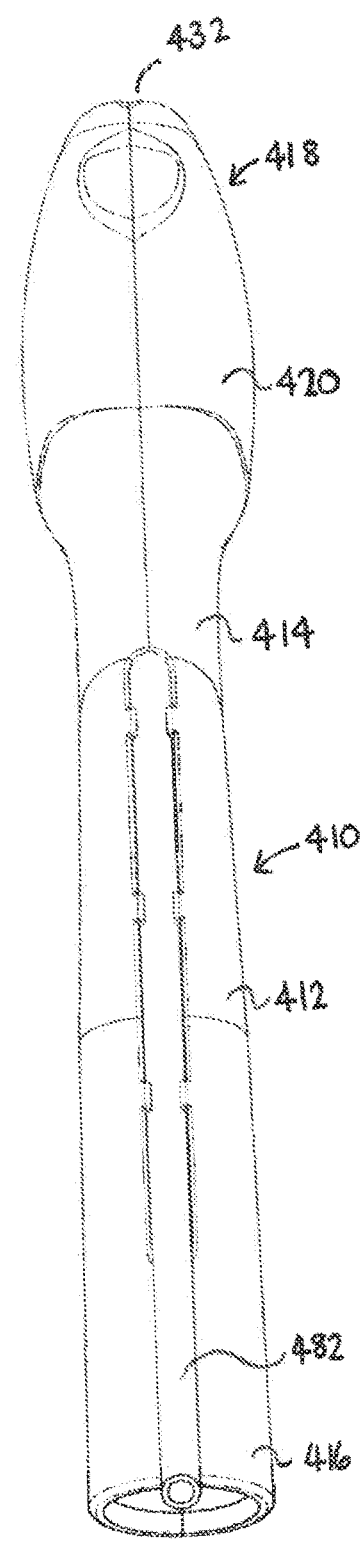
Figure 54
Figure 53

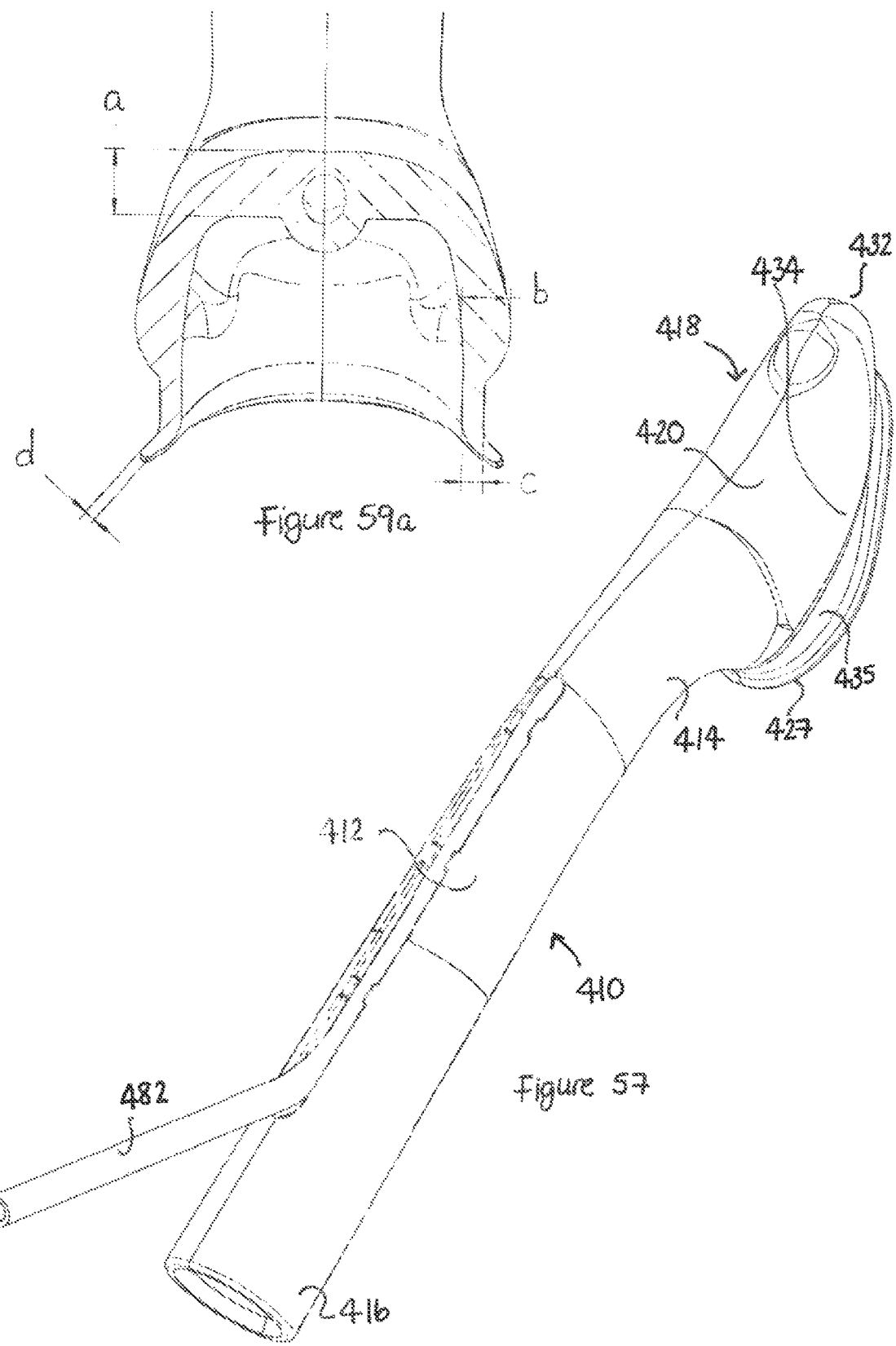

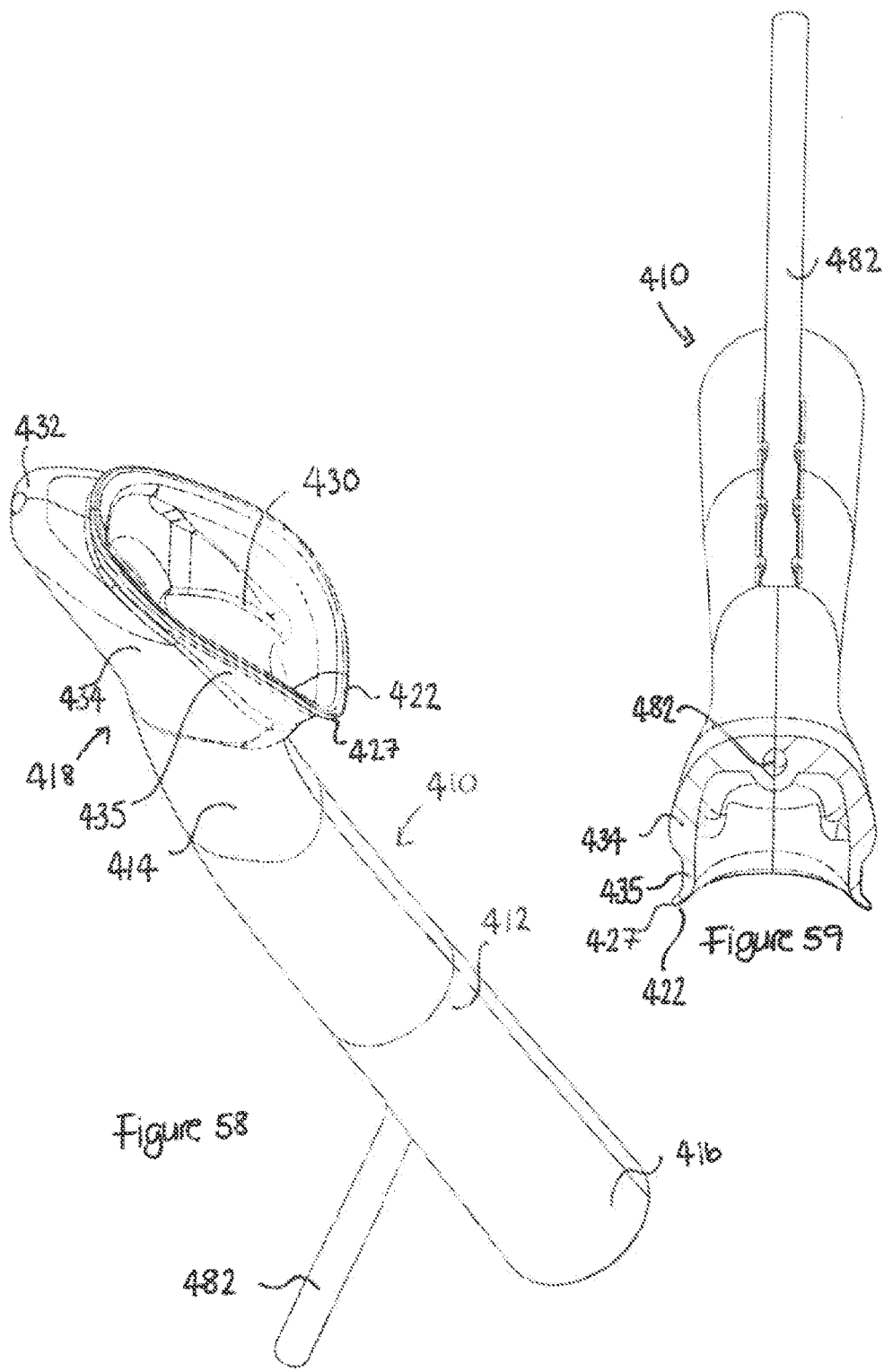

AIRWAY DEVICE

FIELD OF THE INVENTION

The present invention relates to medical devices, namely airway devices. It is applicable to supraglottic devices including laryngeal airway devices and to their methods of manufacture. The present invention is particularly applicable to laryngeal airway devices for human and veterinary use.

BACKGROUND OF THE INVENTION

Various Supraglottic, Periglottic, Intraglottic and Extraglottic airway devices are known and are currently used in establishing and/or maintaining a clear airway for the provision of Oxygen and/or anaesthetic gases during spontaneous breathing or IPPV in anaesthetised patients, or for resuscitation applications. The main focus of developments in such devices has heavily leaned towards ensuring the best shape and material combination to make such devices easy to insert and to improve sealing pressures once the device is in situ within the patient.

A problem that still exists in present supraglottic devices, and in particular in laryngeal airway devices, is the possibility of the epiglottis of the human or animal patient down folding and partially or completely occluding the airway within the device, thus blocking off the gas flow to and from the patient. The problem associated with down folding epiglottis is most applicable to paediatric and animal patients who have a large range in both the flexibility and size of the epiglotti.

In addition, in the case of inflatable devices when the device is inflated it inflates to fill the available space, which can also include filling the space around the laryngeal inlet thus squashing the laryngeal inlet inwards and occluding the airway it is aiming to maintain, especially in the case of paediatric humans, female humans and in small animal patients.

Also in case of inflatable devices when the device is inflated and also in the case of some non-inflatable supraglottic airway devices, the device may buckle in front of the region of the glottis and the laryngeal inlet which may partially or completely obstruct the flow of oxygen and other gases to and from the breathing apparatus.

The main focus of recent developments in such devices has moved away from inflatable devices and instead heavily leaned towards the formation of the cuff from a soft pad from a material with a very low Shore Hardness on the A scale.

US2016/0317768 (NASIR), GB2413963 (NASIR) and US2015/0000672 (JASSELL, NASIR) each describe airway devices with a non-inflatable cuff which is pre-formed to fit over and with the laryngeal frame work of a patient. This means that there is contact between the cuff and the laryngeal frame work of a patient. The cuff is formed from a pad of soft material which provides for a soft deformable pad with a shaped surface to engage over and with the anatomy of the larynx inlet region. The engaging surface of the pad is essentially a mirror image of the structure of and around the larynx such that a face to face constant pressure compression seal is formed between the surface of the pad and the structures of the larynx.

US2018/0177964 (ZHU) describes another airway device with a non-inflatable cuff which is pre-formed to fit over and with the laryngeal frame work of a patient. This means that there is contact between the cuff and the laryngeal frame work of a patient. The cuff is formed from a pad of soft material which provides for a soft deformable pad with a shaped surface to engage over and with the anatomy of the larynx inlet region. The engaging surface of the pad is essentially a mirror image of the structure of and around the larynx such that a face to face constant pressure compression seal is formed between the surface of the pad and the structures of the larynx.

US2011/0023890 (BASKA) describes an airway device with a non-inflatable cuff, which again is designed to fit over and with the laryngeal frame work of a patient. This time instead of having a shaped surface formed from a pad of soft material, a hollow pad (or chamber) is provided which is formed from a resilient material. The surface of the hollow pad (or chamber) is able to deform to form a seal with the larynx. In this airway device the hollow pad (or chamber) is in fluid communication with the airway tube and is able to "inflate" and "deflate" with a bellows action when gas moves through the airway tube when intermittent positive-pressure ventilation (IPPV) is employed. This means that a face to face dynamic compression seal is formed between the resilient surface of the hollow pad and the structures of the larynx.

US2008/0099026 (CHANG) describes an airway device with a non-inflatable cuff which is also designed to fit over and with the laryngeal frame work of a patient. This time instead of a hollow pad (or chamber) a resilient web is provided with a planer sealing surface. The planer surface of the resilient web is able to deform to form a seal with the larynx. This means that a face to face compression seal is formed between the planar sealing surface of the resilient web and the structures of the larynx.

WO2012/127436 (MILLER) describes an airway device with a non-inflatable cuff, which again is designed to fit over and with the laryngeal frame work of a patient. This time instead of having a shaped surface formed from a pad of soft material, a hollow pad (or chamber) is provided which is formed from a resilient material. The surface of the hollow pad (or chamber) is able to deform to form a seal with the larynx. In this airway device the hollow pad (or chamber) is in fluid communication with the airway tube and is able to "inflate" and "deflate" when gas moves through the airway tube when intermittent positive-pressure ventilation (IPPV) is employed. This means that a face to face dynamic compression seal is formed between the resilient surface of the hollow pad and the structures of the larynx.

The problem with using such pads of soft material (whether they are solid pads of material, or foam pads of material, or hollow pads of material, or resilient webs with planar sealing surfaces) is that in order to create a good seal the pad of material needs to be compressed. No matter how soft the material is used, the more the pad is compressed the harder the material will become in the confined space naturally available around the larynx in the pharynx of the human or animal patient. In addition, there is also a maximum amount that the material can be compressed before it can no longer be compressed without a substantial force being exerted upon it.

Furthermore, all of these prior art devices form a seal with structures of the larynx such as the laryngeal inlet of a patient, and the inflation and compression forces exerted by all of these prior art devices risk damaging the delicate structures of the larynx and the peri-larynx that they are forming their compression seals with and also risks displacing airway structures such as the epiglottis which may result in a blocking of the airway of the human or animal patient.

This problem is set out and discussed in "Airway Management Evolution—In a Search for an Ideal Extraglottic Airway Device, Pavel Michalek, Donald M. Miller, Prague Medical Report/Vol. 115 (2014) No. 3-4, p. 87-103". This report sets out that in traditional airway devices as airway pressure rises, a pressure gradient is generated from inside to outside. This may constitute a force for expelling the device. Dislodgement of the device is likely to occur at the peak of inspiration. Factors that prevent that dislodgement are two-fold: Frictional forces and the direction of forces generated by the sealing mechanism in relation to the expulsive force. In the case of the inflatable devices, the frictional force of the device being hooked around the base of the tongue is the main means of preventing it being expelled. The sealing forces related to the cuff are not perpendicular to the expulsive force as is the case with base of-tongue sealing devices, which is mechanically advantageous. In the case of the inflatable devices which as well as the main inflatable cuff have the addition of a cuff on the back of the peri-laryngeal seal to assist in correcting this imbalance to make a more effective seal, where the expulsive forces are perpendicular to the sealing force. The publication goes on to say that base-of-tongue sealers such as SLIPA, which is described in WO0232490, seal with forces that are perpendicular to the expulsive force and hence they seal at higher inflation pressures.

Therefore, all of these traditional prior art airway devices create pressures in and around the delicate structures of the larynx and the peri-larynx that they are forming their compression seals with, and which they are at risk of damaging.

SUMMARY OF THE INVENTION

According to a first aspect of the present invention there is provided an airway device for human or animal use, the device comprising an airway tube having a distal end and a proximal end, the distal end of the airway tube is provided with a pre-formed and non-inflatable peri-pharyngeal bowl, the peri-pharyngeal bowl comprising a posterior bowl portion having a back dorsal portion and a side wall extending around and depending from the periphery of the back dorsal portion to define an internal space, the peri-pharyngeal bowl further comprising a resiliently deformable flange extending laterally from the side wall of the back dorsal portion which defines an extended internal space, the resiliently deformable flange having inner and outer surfaces that extend to a circumferential edge.

Preferably the circumferential edge is provided with a circumferential lip.

Preferably the circumferential edge is rounded or curved such that it is blunt and does not have any square edges.

Preferably the circumferential lip is rounded or curved such that it is blunt and does not have any square edges.

Preferably the resiliently deformable flange forms a generally ovoid shape, preferably the circumferential edge forms a generally ovoid shape, preferably the circumferential lip forms a generally ovoid shape.

Preferably the circumferential lip is formed by providing the circumferential edge with a bend towards to the outer surface of the circumferential edge, preferably the bend is 70° to 90°. Alternatively, the circumferential lip is a separate component connected to the outer surface of the circumferential edge.

Alternatively the circumferential lip is formed by providing the circumferential edge with a bend towards to the inner surface of the circumferential edge, preferably the bend is 70° to 90°. Alternatively, the circumferential lip is a separate component connected to the inner surface of the circumferential edge.

Alternatively the circumferential lip is formed on both sides of the circumferential edge to create a combined circumferential edge and circumferential lip with a larger overall width or footprint than the thickness of the resiliently deformable flange.

Preferably the circumferential lip is the same depth and thickness as the thickness of the resiliently deformable flange.

Preferably the resiliently deformable flange splays outwardly upon application of a force.

Preferably the resiliently deformable flange splays outwardly upon application of a force when in situ in a human or animal patient.

Preferably the resiliently deformable flange forms an impaction seal when in situ in a human or animal patient.

In the case of the present invention an impaction seal is created when pressure is transmitted from contact of the back dorsal portion of the airway device with the posterior pharyngeal wall of the human or animal patient when the device is in situ in the human or animal patient, the pressure is then transmitted first through the side wall, and then through the resiliently deformable flange such that the resiliently deformable flange, circumferential edge and circumferential lip if present, impact against the tissues with which the resiliently deformable flange forms the seal.

Preferably in the case where the resiliently deformable flange splays outwardly upon application of a force a portion of the internal surface of the resiliently deformable flange forms the seal when in situ in a human or animal patient.

Preferably the resiliently deformable flange forms a seal with the peri-larynx in the hypopharynx also known as laryngopharynx of the human or animal patient, preferably by enveloping the glottis in particular within the peri-pharyngeal bowl, more preferably the body of the larynx in general when in situ in a human or animal patient. The peri-larynx is the area around the larynx. Preferably the seal is an impaction seal, preferably the seal is created by a constant impaction seal, preferably the seal is not dynamic. In one alternative a portion of the internal surface of the resiliently deformable flange forms a seal with the peri-larynx in the hypopharynx.

The body of the larynx of the human or animal patient connects the inferior part of the pharynx (hypopharynx) with the trachea and is generally in the shape of a hollow tube. An exemplary illustration of the body of the larynx of the human or animal patient is illustrated in FIGS. 50 to 52. The body of the larynx of the human or animal patient comprises six cartilages, three unpaired and three paired. The unpaired cartilages comprise the thyroid cartilage 1 (which forms the Adam's apple), the cricoid cartilage 2 which forms the inferior wall of the larynx and the epiglottis 3 which varies in shape depending on the species, which forms a lid over the glottis (the opening running through the centre of the body of the larynx). The paired cartilages comprise the arytenoid cartilages 4 which influence the tension and position of the vocal cords, the corniculate cartilages 5 which are located at the apex of each arytenoid cartilage and the cuneiform cartilages 6 which are located anterior to the corniculate cartilages 5.

Preferably the circumferential edge of the resiliently deformable flange forms a seal with the peri-larynx of the human or animal patient when in situ in a human or animal patient. The peri-larynx is the area around the larynx. Preferably the seal is an impaction seal, preferably the seal is a constant impaction seal, preferably the seal is not dynamic. In one alternative a portion of the internal surface of the resiliently deformable flange forms a seal with the peri-larynx of the human or animal patient when in situ in a human or animal patient.

Preferably when the device is in situ in a human or animal patient the circumferential edge has a very small area of contact with the mucosae of base of the tongue, peri-larynx, piriform fossae and upper oesophagus which causes the least amount of pressure trauma, and also maintains blood supply to the mucosae.

Preferably the circumferential lip of the circumferential edge forms a seal with the peri-larynx of the human or animal patient when in situ in a human or animal patient. The peri-larynx is the area around the larynx. Preferably the seal is an impaction seal, preferably the seal is a constant impaction seal, preferably the seal is not dynamic.

Preferably when the device is in situ in a human or animal patient the circumferential lip has a very small area of contact with the mucosae of base of the tongue, peri-larynx, piriform fossae and upper oesophagus which causes the least amount of pressure trauma, and also maintains blood supply to the mucosae.

Preferably the resiliently deformable flange forms a seal within the pharynx and the hypo-pharynx of the human or animal patient when in situ in a human or animal patient by enveloping the glottis in particular and the whole body of the larynx in general. The pharynx is the area of the throat behind the mouth and nasal cavity and above the oesophagus and larynx and the hypo-pharynx is the part of the throat that lies beside and around the larynx. Preferably the seal is an impaction seal, preferably the seal is a constant impaction seal, preferably the seal is not dynamic. In one alternative a portion of the internal surface of the resiliently deformable flange forms a seal within the pharynx and the hypo-pharynx of the human or animal patient when in situ in a human or animal patient by enveloping the glottis in particular and the whole body of the larynx in general.

Preferably the circumferential edge of the resiliently deformable flange forms a seal with the pharynx and the hypo-pharynx of the human or animal patient when in situ in a human or animal patient. The pharynx is the area of the throat behind the mouth and nasal cavity and above the oesophagus and larynx and the hypo-pharynx is the part of the throat that lies beside and around the larynx. Preferably the seal is an impaction seal, preferably the seal is a constant impaction seal, preferably the seal is not dynamic.

Preferably the circumferential lip of the circumferential edge forms a seal with the pharynx and the hypo-pharynx of the human or animal patient when in situ in a human or animal patient. The pharynx is the area of the throat behind the mouth and nasal cavity and above the oesophagus and larynx and the hypo-pharynx is the part of the throat that lies beside and around the larynx. Preferably the seal is an impaction seal, preferably the seal is a constant impaction seal, preferably the seal is not dynamic.

Preferably the resiliently deformable flange forms a seal within and against the mucosa of the pharyngeal and hypo-pharyngeal walls of the human or animal patient when in situ in a human or animal patient. The pharyngeal wall is a wall of the pharynx, the pharynx is the area of the throat behind the mouth and nasal cavity and above the oesophagus and larynx and the hypo-pharyngeal wall is a wall of the hypo-pharynx, the hypo-pharynx is the part of the throat that lies beside and behind the larynx. Preferably the seal is a impaction seal, preferably the seal is a constant impaction seal, preferably the seal is not dynamic. The mucosa is a mucous membrane that lines the various cavities in the body and covers the surface of internal organs. It consists of one or more layers of epithelial cells overlying a layer of loose connective tissue, contained within are small bore, thin walled blood capillaries (which are easily collapsible with only a little compression) that supply the blood to the delicate and easily compressible mucosa. In one alternative a portion of the internal surface of the resiliently deformable flange forms a seal within and against the mucosa of the pharyngeal and hypo-pharyngeal walls of the human or animal patient when in situ in a human or animal patient.

Preferably the resiliently deformable flange forms a substantially continuous ovoid seal with the flattest areas of the mucosa to the front, back and sides of the body of the larynx.

Preferably the circumferential edge of the resiliently deformable flange forms a seal within and against the mucosa of the pharyngeal and hypo-pharyngeal walls of the human or animal patient preferably without compromising the blood supply when in situ in a human or animal patient. This is advantageous over the excessive pressures and vector forces applied and exerted by inflatable and padded devices which may compromise the blood supply to the mucosa by causing exsanguination and compression trauma leading to hypoxic tissue damage leading to inflammation, oedema, swelling, infection, sore throat, dysphagia and desloughing of the damaged mucosa. The pharyngeal wall is a wall of the pharynx, the pharynx is the area of the throat behind the mouth and nasal cavity and above the oesophagus and larynx and the hypo-pharyngeal wall is a wall of the hypo-pharynx, the hypo-pharynx is the part of the throat that lies beside and behind the larynx. Preferably the seal is an impaction seal, preferably the seal is a constant impaction seal, preferably the seal is not dynamic. The mucosa is a mucous membrane that lines the various surfaces of the pharynx, larynx, hypopharynx and laryngopharynx. It consists of one or more layers of epithelial cells overlying a layer of loose connective tissue that have intertwined within thin walled, easily collapsible network of blood capillaries of arterial and venous webbing to supply and drain away blood.

Preferably the circumferential edge of the resiliently deformable flange forms a substantially continuous ovoid seal with the flattest areas of the mucosa to the front, back and sides of the body of the larynx.

Preferably the circumferential lip of the circumferential edge forms a seal within and against the mucosa of the pharyngeal and hypo-pharyngeal walls of the human or animal patient preferably without compromising the blood supply when in situ in a human or animal patient. This is advantageous over the excessive pressures and vector forces applied and exerted by inflatable and padded devices which may compromise the blood supply to the mucosa by causing exsanguination and compression trauma leading to hypoxic tissue damage leading to inflammation, oedema, swelling, infection, sore throat, dysphagia and desloughing of the damaged mucosa. The pharyngeal wall is a wall of the pharynx, the pharynx is the area of the throat behind the mouth and nasal cavity and above the oesophagus and larynx and the hypo-pharyngeal wall is a wall of the hypo-pharynx, the hypo-pharynx is the part of the throat that lies beside and behind the larynx. Preferably the seal is an impaction seal, preferably the seal is a constant impaction seal, preferably the seal is not dynamic. The mucosa is a mucous membrane that lines the various surfaces of the pharynx, larynx, hypopharynx and laryngopharynx. It consists of one or more layers of epithelial cells overlying a layer of loose connective tissue that have intertwined within thin walled, easily collapsible network of blood capillaries of arterial and venous webbing to supply and drain away blood.

Preferably the circumferential lip of the circumferential edge forms a substantially continuous ovoid seal with the flattest areas of the mucosa to the front, back and sides of the body of the larynx.

Preferably the combined internal space, being the internal space and the extended internal space, contains and envelopes 50% to 100% of the body of the larynx of the human or animal patient, preferably without making contact therewith once the airway device is in situ in a human or animal patient.

Preferably the combined internal space, being the internal space and the extended internal space, contains and envelopes 70% to 90% of the body of the larynx of the human or animal patient once the airway device is in situ in a human or animal patient.

Preferably the combined internal space is configured to not only contain the glottis and the body of the larynx, but also to be sufficiently sized such that once the body of the larynx has been contained, preferably without narrowing the natural size and shape of the glottis, laryngeal inlet and overall body of the larynx, that there is still sufficient space in the combined internal space which is enveloping the body of the larynx for gases to freely flow to and from the glottis of the patient without being impeded by the body of the larynx. Preferably in this case the whole of the body of the larynx is contained within the combined internal space.

Preferably the internal space defined by the side walls of the of the back dorsal portion of the peri-pharyngeal bowl contains 50% to 100% of the body of the larynx of the human or animal patient, preferably without making contact therewith once the airway device is in situ in a human or animal patient. This means that even if the resiliently deformable flange is completely deformed such that the extended internal space defined by the resiliently deformable flange is no longer present the internal space defined by the side walls of the back dorsal portion of the peri-pharyngeal bowl is sufficiently sized itself to contain 50% to 100% of the body of the larynx of the human or animal patient, preferably without making contact therewith once the airway device is in situ in a human or animal patient.

Preferably the resiliently deformable flange is configured to extend substantially around the entire circumference of the peri-pharyngeal bowl. Preferably the depth of the resiliently deformable flange is configured to vary around the circumference of the peri-pharyngeal bowl. In one alternative the depth of the resiliently deformable flange is greatest at the proximal end of the peri-pharyngeal bowl and gradually reduces as it moves towards the distal end of the peri-pharyngeal bowl. Preferably the depth of the resiliently deformable flange at the middle of the peri-pharyngeal bowl is about half to about two thirds that of the proximal end of the peri-pharyngeal bowl. Preferably the depth of the resiliently deformable flange at the proximal end of the peri-pharyngeal bowl is about a quarter to about a third that of the distal end of the peri-pharyngeal bowl.

Preferably the thickness of the resiliently deformable flange is uniform, alternatively the resiliently deformable flange is of predetermined variable thickness.

Preferably the thickness of the resiliently deformable flange of the peri-pharyngeal bowl is about 1% to 15% of the external width of the peri-pharyngeal bowl at its widest point. The fact that the resiliently deformable flange is much thinner than the cuffs in prior art non-inflatable devices means that they are more flexible and can be readily deformed when required. In particular, the fact that the resiliently deformable flange of the peri-pharyngeal bowl is readily deformable means that the peri-pharyngeal bowl can be made to be larger overall than the non-inflatable cuffs of prior art airway devices as the resiliently deformable flange of the peri-pharyngeal bowl can be readily deformed to pass through structures, such as the faucial pillars (also known as pharyngoepiglottic folds and ostium in Guinea pigs), which in the past have led to a reduced size of laryngeal cuff in other devices. As the airway device is inserted into the human or animal patient, the peri-pharyngeal bowl comes into contact with the faucial pillars; the resiliently deformable flange of the peri-pharyngeal bowl then deforms allowing the peri-pharyngeal bowl to pass through and beyond the faucial pillars. After the peri-pharyngeal bowl has passed beyond the faucial pillars, the resiliently deformable flange of the peri-pharyngeal bowl and thus the peri-pharyngeal bowl itself regain their original shapes. As the dimensions of the peri-pharyngeal bowl are larger than seen in the cuffs of non-inflatable prior arts devices a more effective seal is created, which allows for higher sealing pressures which are required for IPPV without causing or exerting any excessive pressures to the mucosae of the human or animal patient's pharynx or peri-larynx. The seal that is created is a combination of a compression seal and an impaction seal rather than a suction seal like the seal that is created by a plunger used in plumbing and denture manufacturing.

Preferably in a device for a guinea pig the thickness of the resiliently deformable flange of the peri-pharyngeal bowl is about 10% to 13% of the external width of the peri-pharyngeal bowl at its widest point.

Preferably in a device for a rabbit the thickness of the resiliently deformable flange of the peri-pharyngeal bowl is about 5% to 10% of the external width of the peri-pharyngeal bowl at its widest point.

Preferably in a device for a cat the thickness of the resiliently deformable flange of the peri-pharyngeal bowl is about 5% to 10% of the external width of the peri-pharyngeal bowl at its widest point.

Preferably in a device for a dog the thickness of the resiliently deformable flange of the peri-pharyngeal bowl is about 5% to 10% of the external width of the peri-pharyngeal bowl at its widest point.

Preferably in a device for a horse the thickness of the resiliently deformable flange of the peri-pharyngeal bowl is about 5% to 10% of the external width of the peri-pharyngeal bowl at its widest point.

Preferably in a device for a human the thickness of the resiliently deformable flange of the peri-pharyngeal bowl is about 1% to 5% of the external width of the peri-pharyngeal bowl at its widest point.

Preferably the thickness of the back dorsal portion of the peri-pharyngeal bowl is between about 1 mm to about 15 mm, preferably thickness of the side wall varies between about 0.5 mm to about 12 mm, preferably the thickness of the resiliently deformable flange is between about 0.5 mm to about 5 mm.

Preferably in a device for a guinea pig the thickness of the back dorsal portion of the peri-pharyngeal bowl is between about 1 mm to about 3 mm, preferably thickness of the side wall varies between about 0.5 mm to about 1.5 mm, preferably the thickness of the resiliently deformable flange is between about 0.5 mm to about 1.5 mm.

Preferably in a device for a rabbit the thickness of the back dorsal portion of the peri-pharyngeal bowl is between about 1.5 mm to about 3 mm, preferably thickness of the side wall varies between about 0.5 mm to about 1.5 mm, preferably the thickness of the resiliently deformable flange is between about 0.5 mm to about 1 mm.

Preferably in a device for a cat the thickness of the back dorsal portion of the peri-pharyngeal bowl is between about 2 mm to about 4 mm, preferably thickness of the side wall varies between about 2 mm to about 4 mm, preferably the thickness of the resiliently deformable flange is between about 1 mm to about 2.5 mm.

Preferably in a device for a dog the thickness of the back dorsal portion of the peri-pharyngeal bowl is between about 6 mm to about 10 mm, preferably thickness of the side wall varies between about 3 mm to about 6 mm, preferably the thickness of the resiliently deformable flange is between about 1 mm to about 3 mm.

Preferably in a device for a horse the thickness of the back dorsal portion of the peri-pharyngeal bowl is between about 8 mm to about 15 mm, preferably thickness of the side wall varies between about 8 mm to about 12 mm, preferably the thickness of the resiliently deformable flange is between about 2 mm to about 5 mm.

Preferably in a device for a human the thickness of the back dorsal portion of the peri-pharyngeal bowl is between about 2.5 mm to about 15 mm, preferably thickness of the side wall varies between about 5 mm to about 10 mm, preferably the thickness of the resiliently deformable flange is between about 1 mm to about 4 mm.

In essence the thickness of the walls of the resiliently deformable flange are thinner than the side walls of the posterior bowl portion of the peri-laryngeal bowl.

The transition in the thickness between the side wall and the resiliently deformable flange may be graduated or it may be stepped.

The fact that the resiliently deformable flange is much thinner than the cuffs in prior art non-inflatable devices means that they are more flexible and can be readily deformed when required. In particular, the fact that the resiliently deformable flange of the peri-pharyngeal bowl is readily deformable means that the peri-pharyngeal bowl can be made to be larger overall than the non-inflatable cuffs of prior art airway devices as the resiliently deformable flange of the peri-pharyngeal bowl can be readily deformed to pass through structures, such as the faucial pillars (also known as pharyngoepiglottic folds and ostium in Guinea pigs), which in the past have led to a reduced size of laryngeal cuff in other devices. As the airway device is inserted into the human or animal patient, the peri-pharyngeal bowl comes into contact with the faucial pillars; the resiliently deformable flange of the peri-pharyngeal bowl then deforms allowing the peri-pharyngeal bowl to pass through and beyond the faucial pillars. After the peri-pharyngeal bowl has passed beyond the faucial pillars, the resiliently deformable flange of the peri-pharyngeal bowl and thus the peri-pharyngeal bowl itself regain and bounce/spring back into their original shapes. As the dimensions of the peri-pharyngeal bowl are larger than seen in the cuffs of non-inflatable prior arts devices a more effective seal is created, which allows for higher sealing pressures which are required for IPPV without causing or exerting any excessive pressures to the mucosae of the human or animal patient's pharynx or peri-larynx. The seal that is created is a combination of a compression seal and an impaction seal rather than a suction seal like the seal that is created by a plunger used in plumbing and denture manufacturing.

Preferably the peri-pharyngeal bowl is provided with a tip at the distal end of the peri-pharyngeal bowl. Preferably the tip of the peri-pharyngeal bowl is configured to wedge anatomically correctly into the upper oesophagus region of the human or animal patient to provide a secondary seal to reduce/prevent regurgitation which in turn reduces/eliminates the risk of aspiration pneumonia.

Preferably the exterior of the posterior bowl portion is provided with rounded square corners between the exterior of the back dorsal portion and the side walls of the posterior bowl portion. The rounded square corners provide support and stability to prevent peri-pharyngeal bowl from rocking side to side when in situ in the human or animal patient.

Preferably the exterior of the posterior bowl portion is provided with a flattened back dorsal portion. The flattened back dorsal portion provides support and stability to prevent peri-pharyngeal bowl from rocking side to side when in situ in the human or animal patient. It does this by resting against the domed roof of the pharynx to resist rotation about the longitudinal axis thus stabilising the device.

Preferably the airway device is further provided with a gastric tube passageway, preferably the gastric tube passageway extends along the length of the device exiting through tip of peri-pharyngeal bowl. Preferably the posterior bowl portion houses the gastric tube passage way as it passes through the peri-pharyngeal bowl. Preferably the back dorsal portion of the posterior bowl portion houses the gastric tube passage way as it passes through the peri-pharyngeal bowl.

Preferably the device is further provided with a connector for connecting the device to a gas supply. The gas supply may be oxygen, air, anaesthetic gas etc.

Preferably the device is formed from a single shot of plastics material over moulded around the connector. Preferably the plastics material is of 10 to 90 Shore Hardness on the A scale. In the case of a device for guinea pigs for example the device will be formed from a plastics material of typically 20 to 70 Shore Hardness on the A scale. In the case of a device for rabbits for example the device will be formed from a plastics material of typically 35 to 70 Shore Hardness on the A scale. In the case of a device for cats and/or dogs for example the device will be formed from a plastics material of typically 20 to 60 Shore Hardness on the A scale. In the case of a device for horses for example the device will be formed from a plastics material of typically 20 to 60 Shore Hardness on the A scale. In the case of a device for humans the device will be formed from a plastics material of typically 20 to 50 Shore Hardness on the A scale, preferably less than 50 Shore Hardness on the A scale, preferably less than 40 Shore Hardness on the A scale, preferably 30 to 35 Shore Hardness on the A scale.

In one alternative the connector is formed from a material which loses its structure and/or rigidity when exposed to water. In one alternative the connector is formed from a material that swells when exposed to water such as starch or cellulose. In another alternative the connector is formed from a material that becomes flexible or collapses or dissolves when exposed to water such as polyvinyl alcohol.

In another alternative the connector is formed from a standard plastics material whose structure is not impacted on exposure to water such as polycarbonate, polyurethane, polypropylene or polyvinylchloride.

Preferably the connector is provided with a loop, ring or other member which when over moulded prevents the removal of the connector from the airway tube of the device without also destroying the airway tube of the device. In one alternative the connector is a reduced or low dead space connector.

Essentially the invention provides for a thin walled flexible bowl structure that sits over the top of the larynx and seats on either side of the larynx forming a seal. The airway device comprises a relatively strong bowl that stays open to maintain the airway with a deformable flange structure that is able to flex to pass through the oral and pharyngeal structures and then seal on the floor of the pharynx. By using a bowl formed from a thin material means that a device can be formed of a single material wherein the wall thickness can be varied to provide strong areas and flexible areas. Using a single material eliminates the risk of glue or other bonding failure.

Existing supraglottic airway devices function by pressing the structure directly onto the larynx or both the larynx and epiglottis as described in the background of the invention above. This technique does not recognise that the larynx is a structure that rises up (dorsally) into the pharynx with a strip of pharyngeal mucosa to either side of the larynx rather than the larynx being an integral part of the pharynx.

The distinction between the airway device of the present invention and the supraglottic airway devices of the prior art is the location where the seal is formed. The present invention uses the strips of mucosa in front of, behind and to either side of the larynx/epiglottis to press the seal edge down onto. This is marked by the dots indicated in FIG. 49.

The existing supraglottic airway devices do not take account of the complex three-dimensional structure of the larynx, instead, they rely on compressing these structures flat against the floor of the pharynx until a relatively flat surface is achieved that they can seal against.

The present invention does not attempt to form a seal against the laryngeal structures, instead it uses the existing flat surfaces in front and behind the larynx and the sloped pharyngeal surfaces to either side to seal against. The larynx then extends into the combined internal space in the peri-pharyngeal bowl of the airway device which has been made large enough to completely encompass the body of the larynx, leaving space above (dorsal) and to the side (lateral) for airflow.

The walls of the resiliently deformable flange that form the seal have to be thin for this to work, as the space between the lateral pharyngeal wall and the larynx is slim (of varying width in different species). The thicker walls and pads of the prior art airway devices cannot fit into this space.

BRIEF DESCRIPTION OF THE DRAWINGS

Other aspects and features of the present invention will become apparent to those ordinarily skilled in the art upon review of the following description of specific embodiments of the invention in conjunction with the accompanying figures.

The invention will now be described, by way of example only, with reference the accompanying drawings in which:

FIG. 1 is a top (dorsal) view of an airway device according to a first embodiment of the present invention;

FIG. 2a is a cross-sectional view through A-A of FIG. 2;

FIG. 2b is a cross-sectional view through A-A of FIG. 2 illustrating the position of the thickness of the back dorsal portion of the peri-pharyngeal bowl (a) the thickness of the side wall (b) and the thickness of the resiliently deformable flange (c);

FIG. 3 is a side view of an airway device according to a first embodiment of the present invention;

FIG. 5 is a perspective bottom (ventral) view of an airway device according to a first embodiment of the present invention;

FIG. 11a is a cross-sectional view through A-A of FIG. 11;

FIG. 11b is a cross-sectional view through A-A of FIG. 11 illustrating the position of the thickness of the back dorsal portion of the peri-pharyngeal bowl (a) the thickness of the side wall (b), the thickness of the resiliently deformable flange (c) and the footprint of the circumferential lip and resiliently deformable flange (d);

FIG. 12 is a side view of an airway device according to a second embodiment of the present invention;

FIG. 13 is a cross-sectional view through B-B of FIG. 11;

FIG. 14 is a bottom (ventral) perspective view of an airway device according to a second embodiment of the present invention;

FIG. 19 is a top (dorsal) view of an airway device according to a third embodiment of the present invention;

FIG. 20 is a bottom (ventral) view of an airway device according to a third embodiment of the present invention;

FIG. 24 is a top/bottom (dorsal/ventral) view of the connector of an airway device according to the third embodiment of the present invention;

FIG. 24a is a cross-sectional view through C-C of FIG. 24;

FIG. 25 is a side view of the connector of an airway device according to the third embodiment of the present invention;

FIG. 25a is a cross-sectional view through D-D of FIG. 25;

FIG. 26 is a perspective view of the connector of an airway device according to the third embodiment of the present invention;

FIG. 27 is a front-end view of the connector of an airway device according to the third embodiment of the present invention;

FIG. 28 is a top (dorsal) view of an airway device according to a fourth embodiment of the present invention;

FIG. 29 is a bottom (ventral) view of an airway device according to a fourth embodiment of the present invention;

FIG. 29a is cross-sectional view through A-A of FIG. 29 illustrating the position of the thickness of the back dorsal portion of the peri-pharyngeal bowl (a) the thickness of the side wall (b), the thickness of the resiliently deformable flange (c) and the footprint of the circumferential lip and resiliently deformable flange (d);

FIG. 32 is a bottom (ventral) perspective view of an airway device according to a fourth embodiment of the present invention;

FIG. 34 is a top/bottom (dorsal/ventral) exploded view of the connector of an airway device according to the fourth embodiment of the present invention;

FIG. 35 is an exploded side view of the connector of an airway device according to the fourth embodiment of the present invention;

FIG. 36 is a cross-sectional view through B-B of FIG. 34;

FIG. 37 is a cross-sectional view through C-C of FIG. 35;

FIG. 38 is an exploded perspective view of the connector of an airway device according to the fourth embodiment of the present invention;

FIGS. 42 and 43 are perspective views of the trachea and larynx of a dog; and

FIG. 53 is a top (dorsal) view of an airway device according to a fourth embodiment of the present invention;

FIG. 54 is a bottom (ventral) view of an airway device according to a fifth embodiment of the present invention;

FIG. 57 is a top (dorsal) perspective view of an airway device according to a fifth embodiment of the present invention;

FIG. 58 is a bottom (ventral) perspective view of an airway device according to a fifth embodiment of the present invention;

FIG. 59 is a cross-sectional view through A-A of FIG. 54; and

FIG. 59a is a cross-sectional view through A-A of FIG. 54 illustrating the position of the thickness of the back dorsal portion of the peri-pharyngeal bowl (a) the thickness of the side wall (b), the thickness of the resiliently deformable flange (c) and the footprint of the circumferential lip and resiliently deformable flange (d).

DETAILED DESCRIPTION OF THE PREFERRED EMBODIMENTS

Figure 6:
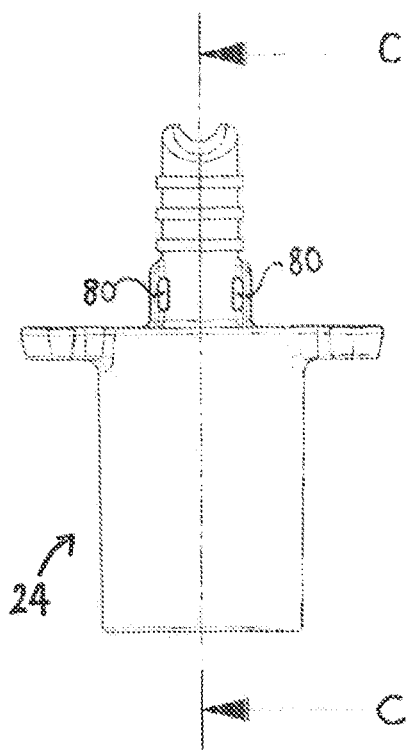
FIG. 6 is a top/bottom (dorsal/ventral) view of the connector of an airway device according to the first embodiment of the present invention.
Figure 7:
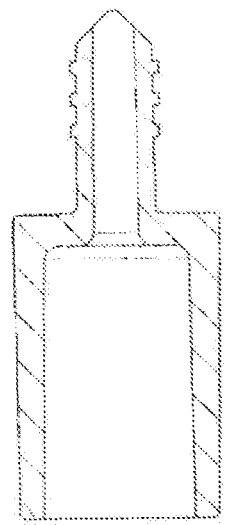
FIG. 7 is a cross-sectional view of the connector through C-C of FIG. 6.
Figure 8:
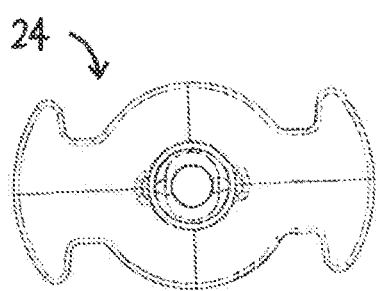
FIG. 8 is a front-end view of the connector of an airway device according to the first embodiment of the present invention.
Figure 9:
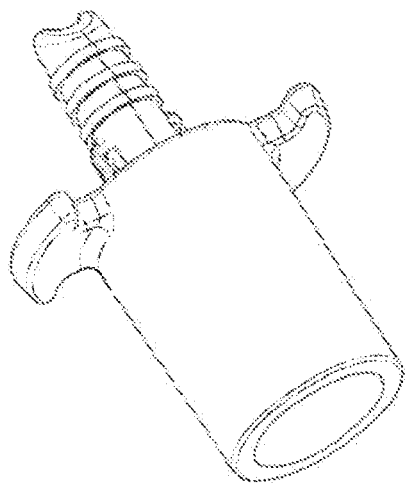
FIG. 9 is a perspective view of the connector of an airway device according to the first embodiment of the present invention.
Figure 10:
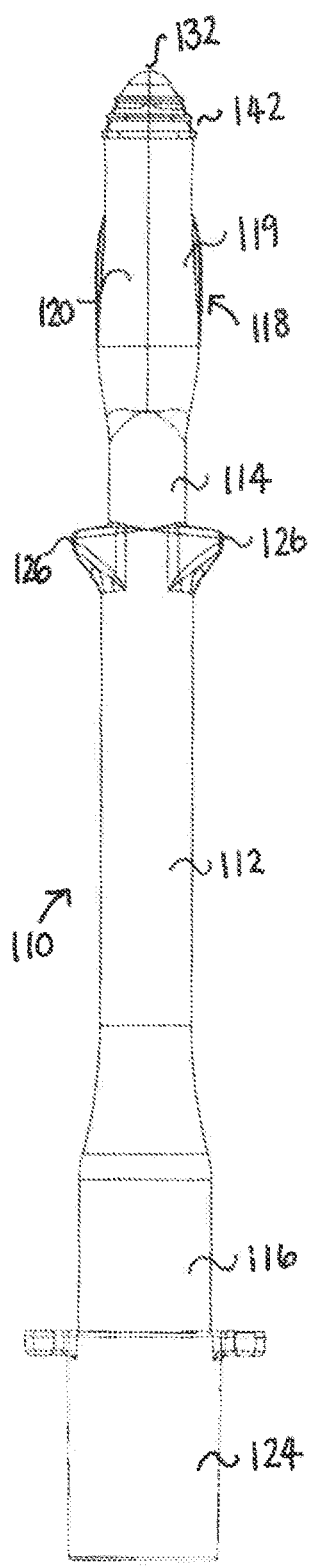
FIG. 10 is a top (dorsal) view of an airway device according to a second embodiment of the present invention.
Figure 11:
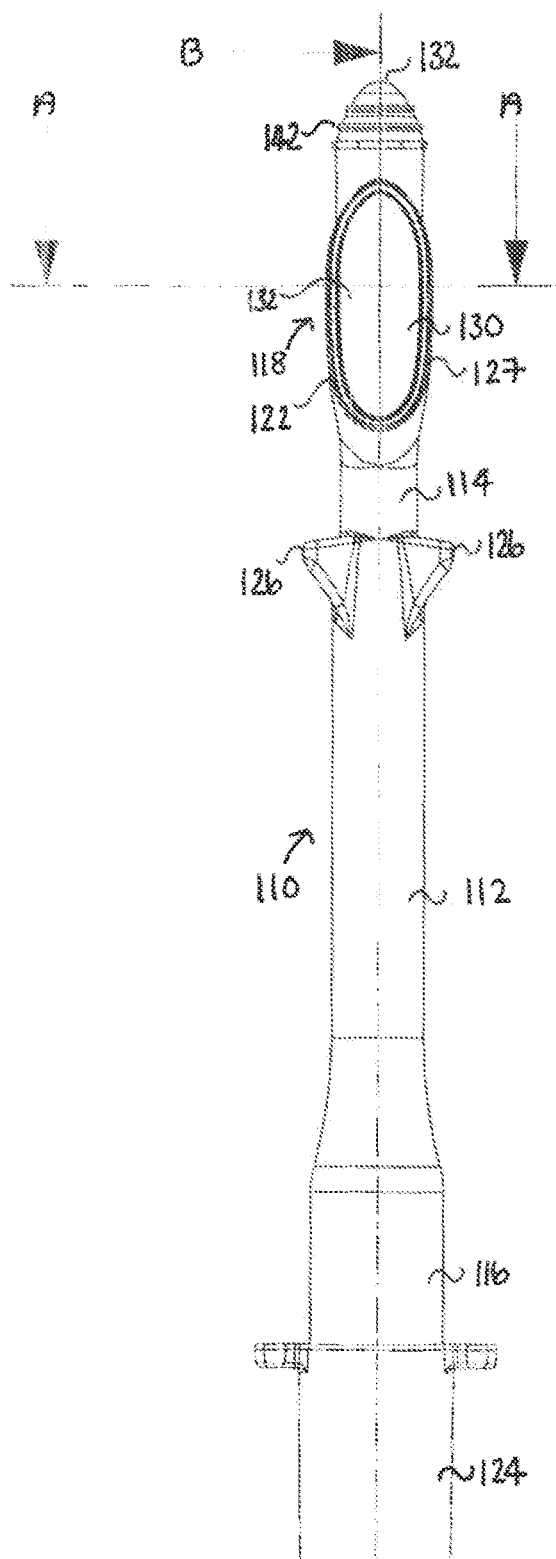
FIG. 11 is a bottom (ventral) view of an airway device according to a second embodiment of the present invention.
Figure 15:
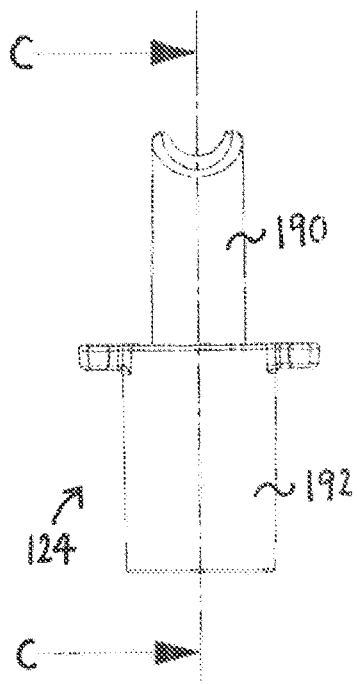
FIG. 15 is a top/bottom (dorsal/ventral) view of the connector of an airway device according to the second embodiment of the present invention.
Figure 15A:
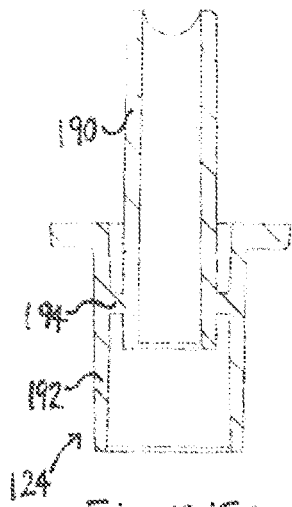
FIG. 15a is a cross-sectional view through C-C of FIG. 16.
Figure 17:
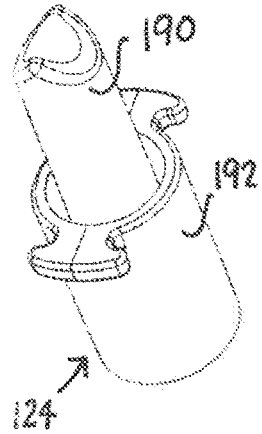
FIG. 17 is a perspective view of the connector of an airway device according to the second embodiment of the present invention.
Figure 16:
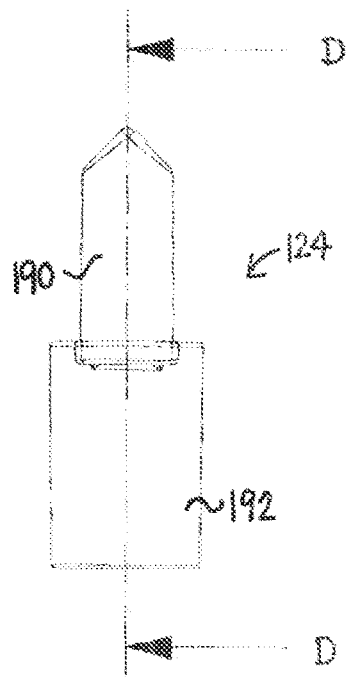
FIG. 16 is a side view of the connector of an airway device according to the second embodiment of the present invention.
Figure 16A:
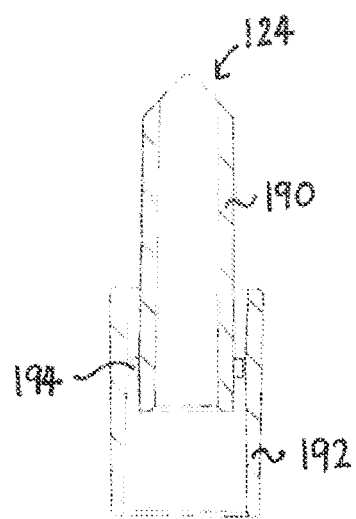
FIG. 16a is a cross-sectional view through D-D of FIG. 16.
Figure 18:
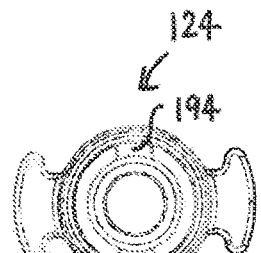
FIG. 18 is a front-end view of the connector of an airway device according to the second embodiment of the present invention.
Figure 20A:
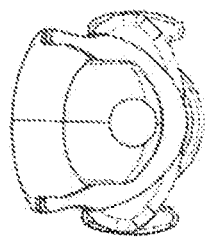
FIG. 20a is a cross-sectional view through A-A of FIG. 20.
Figure 23:
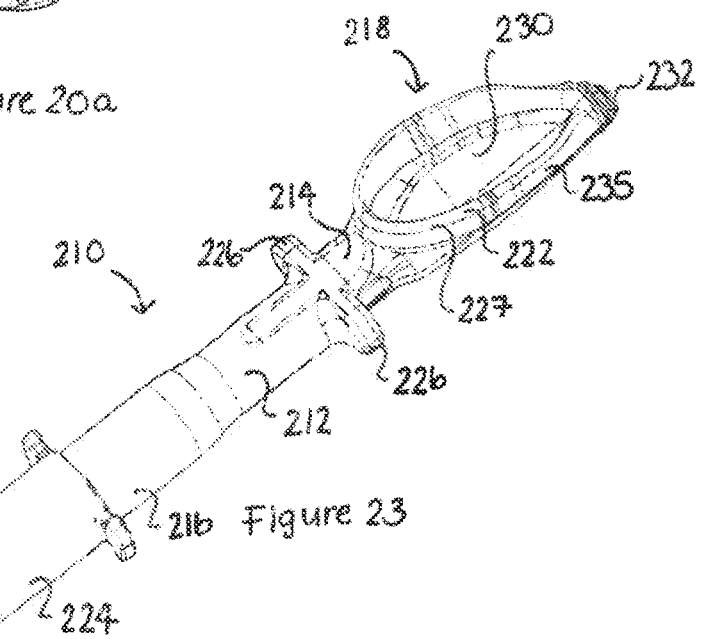
FIG. 23 is a bottom (ventral) perspective view of an airway device according to a third embodiment of the present invention.
Figure 20B:
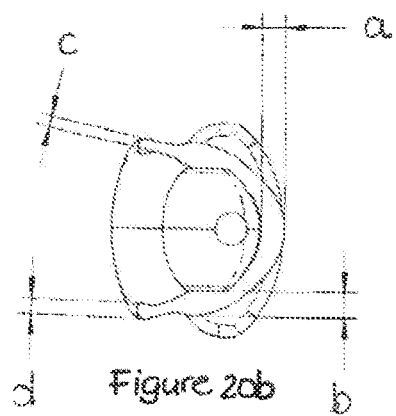
FIG. 20b is a cross-sectional view through A-A of FIG. 20 illustrating the position of the thickness of the back dorsal portion of the peri-pharyngeal bowl (a) the thickness of the side wall (b), the thickness of the resiliently deformable flange (c) and the footprint of the circumferential lip and resiliently deformable flange (d)
Figure 21:
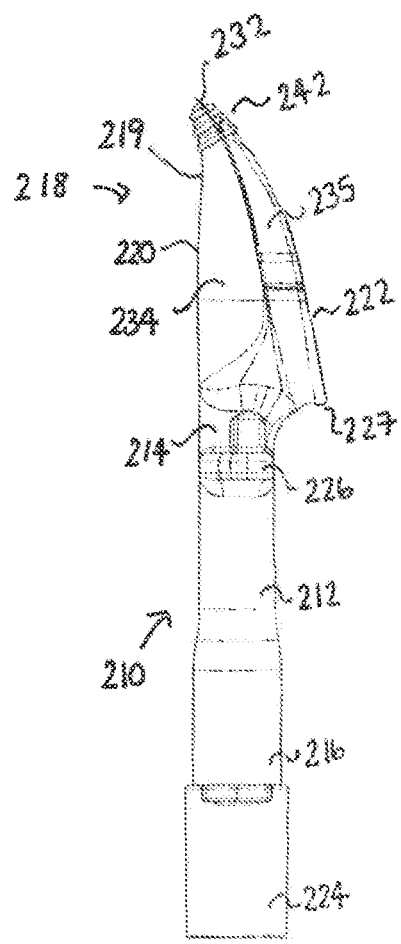
FIG. 21 is a side view of an airway device according to a third embodiment of the present invention.
Figure 22:
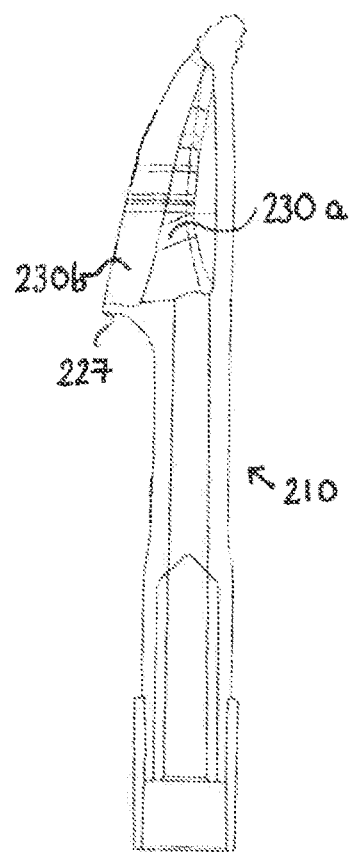
FIG. 22 is a cross-sectional view is a cross-sectional view through B-B of FIG. 20.
Figure 30:
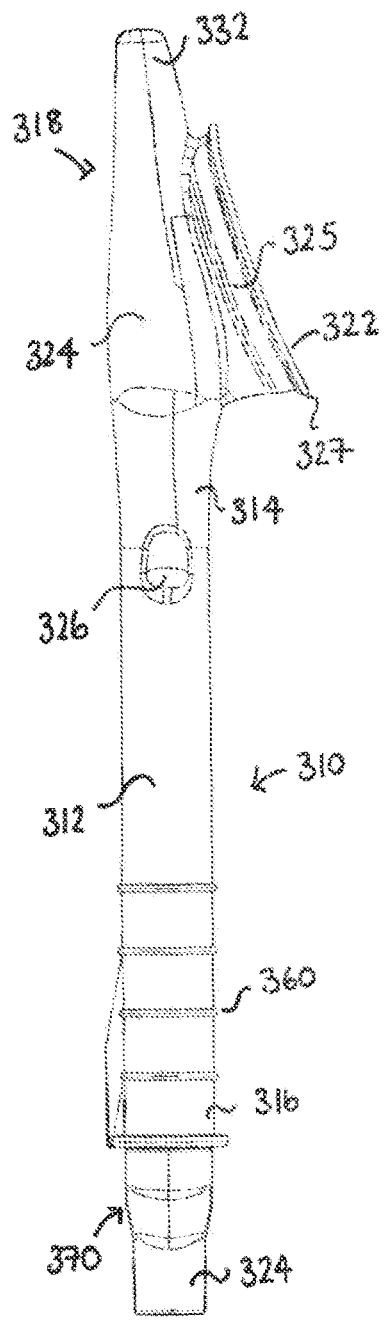
FIG. 30 is a side view of an airway device according to a fourth embodiment of the present invention.
Figure 31:
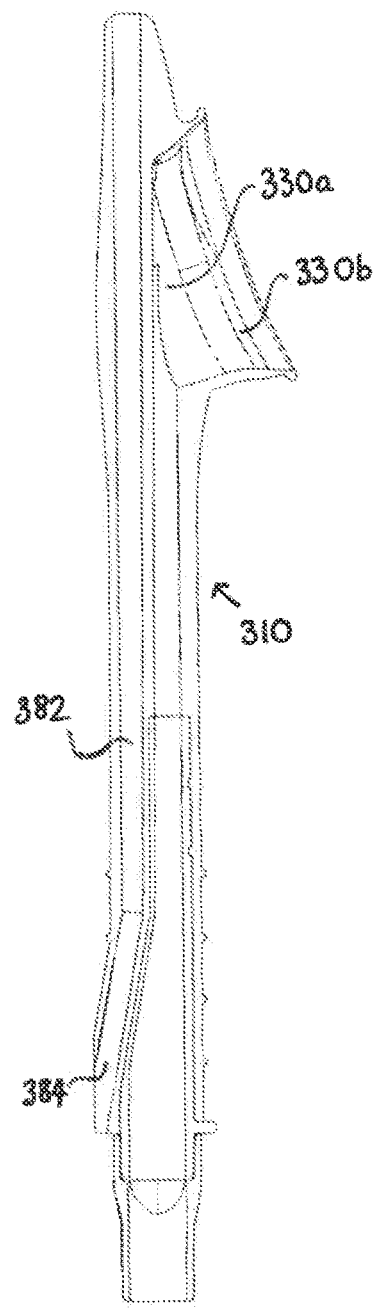
FIG. 31 is a side cross-sectional view through B-B of FIG. 29.
Figure 33:
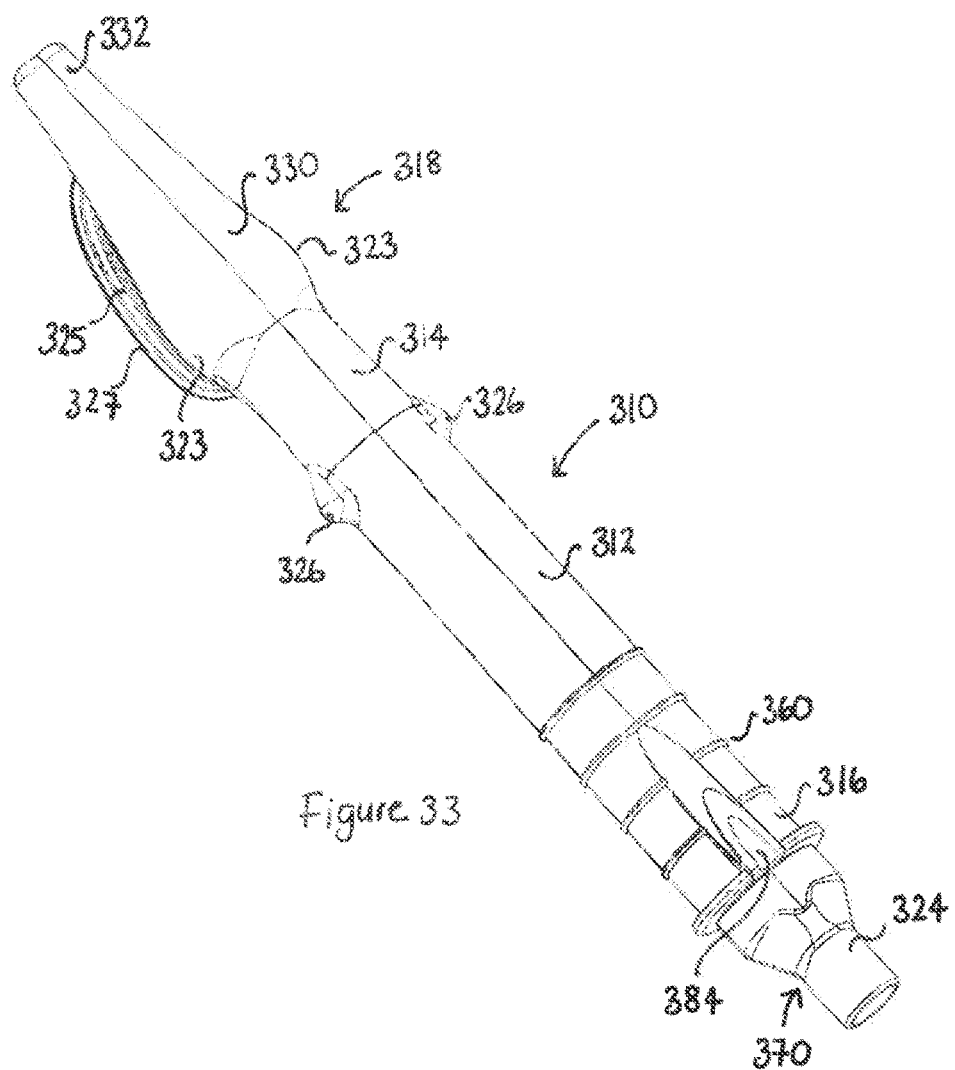
FIG. 33 is a top (dorsal) perspective view of an airway device according to a fourth embodiment of the present invention.

FIGS. 1 to 5 illustrate a first embodiment of an airway device 10 according to the present invention. The airway device 10 has an airway tube 12 with a distal end 14 and a proximal end 16. The distal end 14 of the airway tube 12 is provided with a peri-pharyngeal bowl 18. The peri-pharyngeal bowl is pre-formed in shape and is non-inflatable. The peri-pharyngeal bowl 18 has a posterior bowl portion 19 having a back dorsal portion 20 and a side wall 34 extending around and depending from the periphery of the back dorsal portion 20 which creates an internal space 30a. The peri-pharyngeal bowl 18 also has a resiliently deformable flange 35 which extends laterally from the side wall 34 of the back dorsal portion 20 which creates an extended internal space 30b. The resiliently deformable flange 35 has an inner and an outer surface that extend to a circumferential edge 22 which may be provided with a circumferential lip (not shown in this embodiment). The peri-pharyngeal bowl 18 is generally ovoid in shape.

The proximal end 16 of the airway tube 12 is fitted with a connector 24 such that the proximal end 16 of the airway tube 12 can be connected to the relevant gas supply.

The airway device 10 also optionally has a shoulder 26. The shoulder 26 is used to prevent over-insertion of the airway device 10, and to provide a visual confirmation of insertion depth. The shoulder 26 if present is located laterally or perpendicular to the direction of the airflow, and thus the airway tube 12. The shoulder 26 is used to create a point of contact between the airway device 10 and the faucial pillars located at the back of the mouth of a human or animal patient. This creates a positive stopping feature that in use prevents the shoulder 26 going forward beyond the faucial pillars of the patient to prevent over-insertion of the airway device 10.

The internal volume and depth of the peri-pharyngeal bowl 18, i.e. combination of the internal space 30a and extended internal space 30b together referred to as the combined internal space 30, has been increased compared to that found in the laryngeal cuffs of prior art devices. Previously it was thought that the best way to prevent the epiglottis from occluding the airway was to provide a location external to the laryngeal cuff upon which the epiglottis could rest. This may have been through the use of something extending above and across the opening of the airway in the form of an epiglottic rest for example. It has now been discovered, in particular in devices for use particularly in small animals and paediatric humans, that contrary to the teaching of prior art devices, it is better instead to provide a peri-pharyngeal bowl 18 with a large combined internal space 30, which is configured to contain the body of the larynx of the patient. The combined internal space 30 is configured to not only contain the body of the larynx, but also to be sufficiently sized such that once the body of the larynx has been contained therein that there is still sufficient space in the combined internal space 30 for gases to freely flow to and from the patient without being impeded by the body of the larynx. Preferably the combined internal space 30 contains 50% to 100% of the body of the larynx of the human or animal patient, and more typically 70% to 90% of the body of the larynx of the human or animal patient. In addition, the combined internal space 30 is also configured to contain the body of the larynx of the patient, the body of the larynx should be able to be contained within the combined internal space 30 without any contact being made with any part of the peri-pharyngeal bowl 18 once the airway device 10 is in situ, in particular no contact should be made with the circumferential edge 22, resiliently deformable flange 35 or side wall 34 of the posterior bowl portion of peri-pharyngeal bowl 18. Preferably in this case the whole of the body of the larynx is contained within the combined internal space 30.

In order to achieve a sufficiently large enough combined internal space 30 to accomplish the above, not only has the depth of the peri-pharyngeal bowl been increased, but the sides of the peri-pharyngeal bowl 18 in the form of the resiliently deformable flange 35 extending from the side wall 34 posterior bowl portion 19 has also been reduced in thickness compared to the teaching of prior art laryngeal cuff devices, which taught that thick padded walls were required in order to provide the required sealing levels. Ideally the thickness of the resiliently deformable flange 35 is about 1% to 15% of the external width of the peri-pharyngeal bowl at its widest point.

In addition to creating a large combined internal space 30, the fact that the resiliently deformable flange 35 is much thinner means that it is more flexible and can be readily deformed when required. In particular, the fact that the peri-pharyngeal bowl 18 is readily deformable means that the peri-pharyngeal bowl 18 can be made larger overall than other pre-formed non-inflatable laryngeal cuff prior art devices as the peri-pharyngeal bowl 18 can be readily deformed to pass through structures, such as the faucial pillars, which in the past have led to a reduced size laryngeal cuff in prior art devices. As the peri-pharyngeal bowl 18 comes into contact with the faucial pillars, the resiliently deformable flange 35 deforms inwards allowing the peri-pharyngeal bowl to pass through and beyond the faucial pillars. After the peri-pharyngeal bowl 18 has passed beyond the faucial pillars, the resiliently deformable flange 35, and thus the peri-pharyngeal bowl 18 regain their original shapes. As the dimensions of the peri-pharyngeal bowl 18 are larger than seen in non-inflatable laryngeal cuff prior arts devices a more effective seal is created, which allows for higher sealing pressures which are required for IPPV especially in larger human or animal patients. The seal that is created is an impaction seal.

When pressure is applied to the peri-pharyngeal bowl 18 either from the direction of the back dorsal portion 20 or the circumferential edge 22 of resiliently deformable flange 35, the force is directed through the peri-pharyngeal bowl 18 to the resiliently deformable flange 35, wherein the resiliently deformable flange 35 is configured to bend with the force in order to create a seal between the circumferential edge 22 thereof and the peri-larynx, i.e. the area around the larynx and not the larynx itself as was the case in prior art devices. Given that the circumferential edge 22 of the resiliently deformable flange 35 has a small contact area to form a seal in comparison to the prior art pad style airway devices, less force is required to be applied to the airway device 10 in order for the seal to form.

The thickness of the sides of the peri-pharyngeal bowl 18 in general may be uniform, however, in the embodiment illustrated the thickness is configured to vary from the side walls 34 of the posterior bowl portion 19 of the peri-pharyngeal bowl 18 to the circumferential edge 22 of the resiliently deformable flange 35 of the peri-pharyngeal bowl 18. In the embodiment illustrated the thickness of the sides is greatest in the side walls 34 of the posterior bowl portion 19 of the peri-pharyngeal bowl 18 and gradually reduces as it moves towards the start of the resiliently deformable flange 35 wherein the thickness is then generally uniform up to the circumferential edge 22. The thickness of the sides may be graduated, or it may be stepped.

The peri-pharyngeal bowl 18 is provided with a tip 32 at the distal end of the peri-pharyngeal bowl 18. The tip 32 of the peri-pharyngeal bowl 18 is configured to wedge anatomically correctly into the upper oesophagus region of the human or animal patient. In addition, tip 32 is optionally provided with an annular sealing ring 42 for improved sealing of the tip 32 of the peri-pharyngeal bowl 18 in the upper oesophagus region of the patient. The tip 32 is configured in such a way to optimize the secondary seal at the upper oesophagus such that excess ventilation does not pass beyond which could otherwise result in gastric insufflation and distension; which could otherwise lead to reflux of the gastric contents into the peri-laryngeal bowl 18 of the device.

The side wall 34 is configured to extend substantially around the entire circumference of the peri-pharyngeal bowl 18. The depth of the side wall 34 may be configured to vary around the circumference of the peri-pharyngeal bowl. In one alternative the depth of the side wall 34 is greatest at the proximal end of the peri-pharyngeal bowl 18 and gradually reduces as it moves towards the distal end of the peri-pharyngeal bowl 18. In another alternative the depth of the side wall 34 may be substantially uniform around the circumference of the peri-pharyngeal bowl 18.

The resiliently deformable flange 35 is configured to extend substantially around the entire circumference of the peri-pharyngeal bowl 18. The depth of the resiliently deformable flange 35 may be configured to vary around the circumference of the peri-pharyngeal bowl. In one alternative the depth of the resiliently deformable flange 35 is greatest at the proximal end of the peri-pharyngeal bowl 18 and gradually reduces as it moves towards the distal end of the peri-pharyngeal bowl 18. In another alternative the depth of the resiliently deformable flange 35 may be substantially uniform around the circumference of the peri-pharyngeal bowl 18.

The circumferential edge 22 of the peri-pharyngeal bowl 18 is preferably rounded or curved such that is it blunt and does not have any squared edges in such a way that whilst it is able to maintain the seal, the circumferential edge 22 does not cause excessive mucosal pressures thus avoiding any trauma to the delicate structures. If a circumferential lip is provided it too is preferably rounded or curved such that is it blunt and does not have any squared edges in such a way that it does not cause excessive mucosal pressures thus avoiding any trauma to the delicate structures The airway device 10 is formed from a single shot of plastics material over moulded around the connector 24. Preferably the plastics material is of 10 to 90 Shore Hardness on the A scale. In the case of a device for guinea pigs for example the device will be formed from a plastics material of typically 20 to 70 Shore Hardness on the A scale. In the case of a device for rabbits for example the device will be formed from a plastics material of typically 35 to 70 Shore Hardness on the A scale. In the case of a device for cats and/or dogs for example the device will be formed from a plastics material of typically 20 to 60 Shore Hardness on the A scale. In the case of a device for horses for example the device will be formed from a plastics material of typically 20 to 60 Shore Hardness on the A scale. In the case of a device for humans the device will be formed from a plastics material of typically 20 to 50 Shore Hardness on the A scale, preferably less than 50 Shore Hardness on the A scale, preferably less than 40 Shore Hardness on the A scale, preferably 30 to 35 Shore Hardness on the A scale.

The connector 24 may be formed from a material which loses its structure and/or rigidity when exposed to water. In one alternative the connector 24 may be formed from a material that swells when exposed to water such as starch or cellulose. In another alternative the connector 24 may be formed from a material that becomes flexible or collapses or dissolves when exposed to water such as polyvinyl alcohol.

In an alternative the connector 24 may be formed from a standard plastics material whose structure is not impacted on exposure to water such as polycarbonate, polyurethane, polypropylene or polyvinylchloride.

In addition, as illustrated in FIGS. 6 to 9 the connector 24 is optionally provided with loops or rings 80 which when over moulded prevents the removal of the connector 24 from the airway tube 12 of the airway device 10 without also destroying the airway tube 12 of the airway device 10. In an alternative not illustrated the connector 24 is optionally provided with a tube within a tube arrangement wherein the inner tube corresponds to the diameter of the airway tube 12 and the outer tube corresponds with the diameter required to connect to the to the relevant gas supply wherein one or more spigots are provided to connect the inner tube to the outer tube. In this arrangement when the connector 24 is over moulded the plastics material fills the void between the inner and outer tubes and over and around the one of more spigots which prevents the removal of the connector 24 from the airway tube 12 of the airway device 10 without also destroying the airway tube 12 of the airway device 10. In one alternative the connector is a reduced or low dead space connector.

The airway device 10 is optionally also further provided with a plurality of ribs (not shown) near the proximal end 16 of the airway tube 12 near to the connector 24. The ribs provide a friction point for tying the device around an animal's head as it is generally not possible to use tape as in humans due to the animal's fur.

FIGS. 10 to 14 illustrate a second embodiment of an airway device 110 according to the present invention. The airway device 110 has an airway tube 112 with a distal end 114 and a proximal end 116. The distal end 114 of the airway tube 112 is provided with a peri-pharyngeal bowl 118. The peri-pharyngeal bowl is pre-formed in shape and is non-inflatable. The peri-pharyngeal bowl 118 has a posterior bowl portion 119 having a back dorsal portion 120 and a side wall 134 extending around and depending from the periphery of the back dorsal portion 120 which creates an internal space 130a. The peri-pharyngeal bowl 118 also has a resiliently deformable flange 135 which extends laterally from the side wall 134 of the back dorsal portion 120 which creates an extended internal space 130b. The resiliently deformable flange 135 has an inner and an outer surface that extend to a circumferential edge 122 which may be provided with a circumferential lip 127. The peri-pharyngeal bowl 18 is generally ovoid in shape.

In the embodiment illustrated the circumferential lip 127 is formed by providing the circumferential edge 122 with a bend towards to the outer surface of the circumferential edge 122, preferably the bend is 70° to 90°. Alternatively, the circumferential lip 127 may be a separate component connected to the outer surface of the circumferential edge 122.

The proximal end 116 of the airway tube 112 is fitted with a connector 124 such that the proximal end 116 of the airway tube 112 can be connected to the relevant gas supply.

The airway device 110 also optionally has a shoulder 126. The shoulder 126 is used to prevent over-insertion of the airway device 110, and to provide a visual confirmation of insertion depth. The shoulder 26 is located laterally or perpendicular to the direction of the airflow, and thus the airway tube 112. The shoulder 126 is used to create a point of contact between the airway device 110 and the faucial pillars located at the back of the mouth of a human or animal patient. This creates a positive stopping feature that in use prevents the shoulder 126 going forward beyond the faucial pillars of the patient to prevent over-insertion of the airway device 110.

The internal volume and depth of the peri-pharyngeal bowl 118, i.e. combination of the internal space 130a and extended internal space 130b together referred to as the combined internal space 130, has been increased compared to that found in the laryngeal cuffs of prior art devices. Previously it was thought that the best way to prevent the epiglottis from occluding the airway was to provide a location external to the laryngeal cuff upon which the epiglottis could rest. This may have been through the use of something extending above and across the opening of the airway in the form of an epiglottic rest for example. It has now been discovered, in particular in devices for use particularly in small animals and paediatric humans, that contrary to the teaching of prior art devices, it is better instead to provide a peri-pharyngeal bowl 118 with a large combined internal space 130, which is configured to contain the body of the larynx of the patient. The combined internal space 130 is configured to not only contain the body of the larynx, but also to be sufficiently sized such that once the body of the larynx has been contained therein that there is still sufficient space in the combined internal space 130 for gases to freely flow to and from the patient without being impeded by the body of the larynx. Preferably the combined internal space 130 contains 50% to 100% of the body of the larynx of the human or animal patient, and more typically 70% to 90% of the body of the larynx of the human or animal patient. In addition, the combined internal space 130 is also configured to contain the body of the larynx of the patient, the body of the larynx should be able to be contained within the combined internal space 130 without any contact being made with any part of the peri-pharyngeal bowl 118 once the airway device 110 is in situ, in particular no contact should be made with the circumferential edge 122, resiliently deformable flange 135 or side wall 134 of the posterior bowl portion 119 of peri-pharyngeal bowl 118. Preferably in this case the whole of the body of the larynx is contained within the combined internal space 130.

In order to achieve a sufficiently large enough combined internal space 130 to accomplish the above, not only has the depth of the peri-pharyngeal bowl been increased, but the sides of the peri-pharyngeal bowl 118 in the form of the resiliently deformable flange 135 extending from the side wall 134 posterior bowl portion 119 has also been reduced in thickness compared to the teaching of prior art laryngeal cuff devices, which taught that thick padded walls were required in order to provide the required sealing levels. Ideally the thickness of the resiliently deformable flange 135 is about 1% to 15% of the external width of the peri-pharyngeal bowl at its widest point In addition to creating a large combined internal space 130, the fact that the resiliently deformable flange 135 is much thinner means that it is more flexible and can be readily deformed when required. In particular, the fact that the peri-pharyngeal bowl 118 is readily deformable means that the peri-pharyngeal bowl 118 can be made larger overall than other pre-formed non-inflatable laryngeal cuff prior art devices as the peri-pharyngeal bowl 118 can be readily deformed to pass through structures, such as the faucial pillars, which in the past have led to a reduced size laryngeal cuff in prior art devices. As the peri-pharyngeal bowl 118 comes into contact with the faucial pillars, the resiliently deformable flange 135 deforms inwards allowing the peri-pharyngeal bowl to pass through and beyond the faucial pillars. After the peri-pharyngeal bowl 118 has passed beyond the faucial pillars, the resiliently deformable flange 135, and thus the peri-pharyngeal bowl 118 regain their original shapes. As the dimensions of the peri-pharyngeal bowl 118 are larger than seen in non-inflatable laryngeal cuff prior arts devices a more effective seal is created, which allows for higher sealing pressures which are required for IPPV especially in larger human or animal patients. The seal that is created is an impaction seal.

When pressure is applied to the peri-pharyngeal bowl 118 either from the direction of the back dorsal portion 120 or the circumferential edge 122 of resiliently deformable flange 135, the force is directed through the peri-pharyngeal bowl 118 to the resiliently deformable flange 135, wherein the resiliently deformable flange 135 is configured to bend with the force in order to create a seal between the circumferential edge 122 thereof and the peri-larynx, i.e. the area around the larynx and not the larynx itself as was the case in prior art devices. Given that the circumferential edge 122 of the resiliently deformable flange 135 has a small contact area to form a seal in comparison to the prior art pad style airway devices, less force is required to be applied to the airway device 110 in order for the seal to form.

The thickness of the sides of the peri-pharyngeal bowl 118 in general may be uniform, however, in the embodiment illustrated the thickness is configured to vary from the side walls 134 of the posterior bowl portion 119 of the peri-pharyngeal bowl 118 to the circumferential edge 122 of the resiliently deformable flange 135 of the peri-pharyngeal bowl 118. In the embodiment illustrated the thickness of the sides is greatest in the side walls 134 of the posterior bowl portion 119 of the peri-pharyngeal bowl 118 and gradually reduces as it moves towards the start of the resiliently deformable flange 135 wherein the thickness is then generally uniform up to the circumferential edge 122. The thickness of the sides may be graduated, or it may be stepped.

The side wall 134 is configured to extend substantially around the entire circumference of the peri-pharyngeal bowl 118. The depth of the side wall 134 may be configured to vary around the circumference of the peri-pharyngeal bowl. In one alternative the depth of the side wall 134 is greatest at the proximal end of the peri-pharyngeal bowl 18 and gradually reduces as it moves towards the distal end of the peri-pharyngeal bowl 118. In another alternative the depth of the side wall 134 may be substantially uniform around the circumference of the peri-pharyngeal bowl 118.

The peri-pharyngeal bowl 18 is provided with a tip 132 at the distal end of the peri-pharyngeal bowl 118. The tip 132 of the peri-pharyngeal bowl 118 is configured to wedge anatomically correctly into the upper oesophagus region of the human or animal patient. In addition, tip 132 is optionally provided with one or more annular sealing rings 142 for improved sealing of the tip 132 of the peri-pharyngeal bowl 118 in the upper oesophagus region of the patient. The tip 132 is configured in such a way to optimize the secondary seal at the upper oesophagus such that excess ventilation does not pass beyond which could otherwise result in gastric insufflation and distension; which could otherwise lead to reflux of the gastric contents into the peri-laryngeal bowl 118 of the device.

The resiliently deformable flange 135 is configured to extend substantially around the entire circumference of the peri-pharyngeal bowl 118. The depth of the resiliently deformable flange 135 may be configured to vary around the circumference of the peri-pharyngeal bowl. In one alternative the depth of the resiliently deformable flange 135 is greatest at the proximal end of the peri-pharyngeal bowl 118 and gradually reduces as it moves towards the distal end of the peri-pharyngeal bowl 118. In another alternative the depth of the resiliently deformable flange 135 may be substantially uniform around the circumference of the peri-pharyngeal bowl 118.

The circumferential edge 122 of the peri-pharyngeal bowl 118 is preferably rounded or curved such that is it blunt and does not have any squared edges in such a way that whilst it is able to maintain the seal, the circumferential edge 122 does not cause excessive mucosal pressures thus avoiding any trauma to the delicate structures. If a circumferential lip is provided it too is preferably rounded or curved such that is it blunt and does not have any squared edges in such a way that it does not cause excessive mucosal pressures thus avoiding any trauma to the delicate structures.

The airway device 110 is formed from a single shot of plastics material over moulded around the connector 124. Preferably the plastics material is of 10 to 90 Shore Hardness on the A scale. In the case of a device for guinea pigs for example the device will be formed from a plastics material of typically 20 to 70 Shore Hardness on the A scale. In the case of a device for rabbits for example the device will be formed from a plastics material of typically 35 to 70 Shore Hardness on the A scale. In the case of a device for cats and/or dogs for example the device will be formed from a plastics material of typically 20 to 60 Shore Hardness on the A scale. In the case of a device for horses for example the device will be formed from a plastics material of typically 20 to 60 Shore Hardness on the A scale. In the case of a device for humans the device will be formed from a plastics material of typically 20 to 50 Shore Hardness on the A scale, preferably less than 50 Shore Hardness on the A scale, preferably less than 40 Shore Hardness on the A scale, preferably 30 to 35 Shore Hardness on the A scale.

The connector 124 may be formed from a material which loses its structure and/or rigidity when exposed to water. In one alternative the connector 124 may be formed from a material that swells when exposed to water such as starch or cellulose. In another alternative the connector 214 may be formed from a material that becomes flexible or collapses or dissolves when exposed to water such as polyvinyl alcohol.

In an alternative the connector 124 may be formed from a standard plastics material whose structure is not impacted on exposure to water such as polycarbonate, polyurethane, polypropylene or polyvinylchloride.

In addition, as illustrated in FIGS. 15 to 18 the connector 124 is provided with a tube within a tube arrangement wherein the inner tube 190 corresponds to the diameter of the airway tube 112 and the outer tube 192 corresponds with the diameter required to connect to the to the relevant gas supply wherein one or more spigots 194 are provided to connect the inner tube 190 to the outer tube 192. In this arrangement when the connector 124 is over moulded the plastics material fills the void between the inner and outer tubes 190, 192 and over and around the one of more spigots 194 which prevents the removal of the connector 124 from the airway tube 112 of the airway device 110 without also destroying the airway tube 112 of the airway device 110. In an alternative loops or rings may be provided on the external surface of the connector as illustrated in respect of the first embodiment of the invention which when over moulded prevents the removal of the connector 124 from the airway tube 112 of the airway device 110 without also destroying the airway tube 112 of the airway device 110. In one alternative the connector is a reduced or low dead space connector.

The airway device 110 is optionally also further provided with a plurality of ribs (not shown) near the proximal end 116 of the airway tube 112 near to the connector 124. The ribs provide a friction point for tying the device around an animal's head as it is generally not possible to use tape as in humans due to the animal's fur.

FIGS. 19 to 23 illustrate a third embodiment of an airway device 210 according to the present invention. The airway device 210 has an airway tube 212 with a distal end 214 and a proximal end 216. The distal end 214 of the airway tube 212 is provided with a peri-pharyngeal bowl 218. The peri-pharyngeal bowl is pre-formed in shape and is non-inflatable. The peri-pharyngeal bowl 218 has a posterior bowl portion 219 having a back dorsal portion 220 and a side wall 234 extending around and depending from the periphery of the back dorsal portion 220 which creates an internal space 230a. The peri-pharyngeal bowl 218 also has a resiliently deformable flange 235 which extends laterally from the side wall 234 of the back dorsal portion 220 which creates an extended internal space 230b. The resiliently deformable flange 235 has an inner and an outer surface that extend to a circumferential edge 222 which may be provided with a circumferential lip 227. The peri-pharyngeal bowl 218 is generally ovoid in shape.

In the embodiment illustrated the circumferential lip 227 is formed by providing the circumferential edge 222 with a bend towards to the both the outer and inner surfaces of the circumferential edge 222, preferably the bend is 70° to 90°. Alternatively, the circumferential lip 227 may be a separate component connected to the outer surface of the circumferential edge 222.

The proximal end 216 of the airway tube 212 is fitted with a connector 224 such that the proximal end 216 of the airway tube 212 can be connected to the relevant gas supply.

The airway device 210 also optionally has a shoulder 226. The shoulder 226 is used to prevent over-insertion of the airway device 210, and to provide a visual confirmation of insertion depth. The shoulder 226 if present is located laterally or perpendicular to the direction of the airflow, and thus the airway tube 212. The shoulder 226 is used to create a point of contact between the airway device 210 and the faucial pillars located at the back of the mouth of a human or animal patient. This creates a positive stopping feature that in use prevents the shoulder 226 going forward beyond the faucial pillars of the patient to prevent over-insertion of the airway device 210.

The internal volume and depth of the peri-pharyngeal bowl 218, i.e. combination of the internal space 230a and extended internal space 230b together referred to as the combined internal space 230, has been increased compared to that found in the laryngeal cuffs of prior art devices. Previously it was thought that the best way to prevent the epiglottis from occluding the airway was to provide a location external to the laryngeal cuff upon which the epiglottis could rest. This may have been through the use of something extending above and across the opening of the airway in the form of an epiglottic rest for example. It has now been discovered, in particular in devices for use particularly in small animals and paediatric humans, that contrary to the teaching of prior art devices, it is better instead to provide a peri-pharyngeal bowl 218 with a large combined internal space 230, which is configured to contain the body of the larynx of the patient. The combined internal space 230 is configured to not only contain the body of the larynx, but also to be sufficiently sized such that once the body of the larynx has been contained therein that there is still sufficient space in the combined internal space 230 for gases to freely flow to and from the patient without being impeded by the body of the larynx. Preferably the combined internal space 230 contains 50% to 100% of the body of the larynx of the human or animal patient, and more typically 70% to 90% of the body of the larynx of the human or animal patient. In addition, the combined internal space 230 is also configured to contain the body of the larynx of the patient, the body of the larynx should be able to be contained within the combined internal space 230 without any contact being made with any part of the peri-pharyngeal bowl 218 once the airway device 210 is in situ, in particular no contact should be made with the circumferential edge 222, resiliently deformable flange 235 or side wall 234 of the posterior bowl portion 219 of peri-pharyngeal bowl 218. Preferably in this case the whole of the body of the larynx is contained within the combined internal space 230.

In order to achieve a sufficiently large enough combined internal space 230 to accomplish the above, not only has the depth of the peri-pharyngeal bowl been increased, but the sides of the peri-pharyngeal bowl 218 in the form of the resiliently deformable flange 235 extending from the side wall 234 posterior bowl portion 219 has also been reduced in thickness compared to the teaching of prior art laryngeal cuff devices, which taught that thick padded walls were required in order to provide the required sealing levels. Ideally the thickness of the resiliently deformable flange 235 is about 1% to 15% of the external width of the peri-pharyngeal bowl at its widest point In addition to creating a large combined internal space 230, the fact that the resiliently deformable flange 235 is much thinner means that it is more flexible and can be readily deformed when required. In particular, the fact that the peri-pharyngeal bowl 218 is readily deformable means that the peri-pharyngeal bowl 218 can be made larger overall than other pre-formed non-inflatable laryngeal cuff prior art devices as the peri-pharyngeal bowl 218 can be readily deformed to pass through structures, such as the faucial pillars, which in the past have led to a reduced size laryngeal cuff in prior art devices. As the peri-pharyngeal bowl 218 comes into contact with the faucial pillars, the resiliently deformable flange 235 deforms inwards allowing the peri-pharyngeal bowl to pass through and beyond the faucial pillars. After the peri-pharyngeal bowl 218 has passed beyond the faucial pillars, the resiliently deformable flange 235, and thus the peri-pharyngeal bowl 218 regain their original shapes. As the dimensions of the peri-pharyngeal bowl 218 are larger than seen in non-inflatable laryngeal cuff prior arts devices a more effective seal is created, which allows for higher sealing pressures which are required for IPPV especially in larger human or animal patients. The seal that is created is an impaction seal.

When pressure is applied to the peri-pharyngeal bowl 218 either from the direction of the back dorsal portion 220 or the circumferential edge 222 of resiliently deformable flange 235, the force is directed through the peri-pharyngeal bowl 218 to the resiliently deformable flange 235, wherein the resiliently deformable flange 235 is configured to bend with the force in order to create a seal between the circumferential edge 222 thereof and the peri-larynx, i.e. the area around the larynx and not the larynx itself as was the case in prior art devices. Given that the circumferential edge 222 of the resiliently deformable flange 235 has a small contact area to form a seal in comparison to the prior art pad style airway devices, less force is required to be applied to the airway device 210 in order for the seal to form.

The thickness of the sides of the peri-pharyngeal bowl 218 in general may be uniform, however, in the embodiment illustrated the thickness is configured to vary from the side walls 234 of the posterior bowl portion 219 of the peri-pharyngeal bowl 218 to the circumferential edge 222 of the resiliently deformable flange 235 of the peri-pharyngeal bowl 218. In the embodiment illustrated the thickness of the sides is greatest in the side walls 234 of the posterior bowl portion 219 of the peri-pharyngeal bowl 218 and gradually reduces as it moves towards the start of the resiliently deformable flange 235 wherein the thickness is then generally uniform up to the circumferential edge 222. The thickness of the sides may be graduated, or it may be stepped.

The side wall 234 is configured to extend substantially around the entire circumference of the peri-pharyngeal bowl 218. The depth of the side wall 234 may be configured to vary around the circumference of the peri-pharyngeal bowl. In one alternative the depth of the side wall 234 is greatest at the proximal end of the peri-pharyngeal bowl 218 and gradually reduces as it moves towards the distal end of the peri-pharyngeal bowl 218. In another alternative the depth of the side wall 234 may be substantially uniform around the circumference of the peri-pharyngeal bowl 218.

The peri-pharyngeal bowl 218 is provided with a tip 232 at the distal end of the peri-pharyngeal bowl 218. The tip 232 of the peri-pharyngeal bowl 218 is configured to wedge anatomically correctly into the upper oesophagus region of the human or animal patient. In addition, tip 232 is optionally provided with one or more annular sealing rings 242 for improved sealing of the tip 232 of the peri-pharyngeal bowl 218 in the upper oesophagus region of the patient. The tip 232 is configured in such a way to optimize the secondary seal at the upper oesophagus such that excess ventilation does not pass beyond which could otherwise result in gastric insufflation and distension; which could otherwise lead to reflux of the gastric contents into the peri-laryngeal bowl 218 of the device.

The resiliently deformable flange 235 is configured to extend substantially around the entire circumference of the peri-pharyngeal bowl 218. The depth of the resiliently deformable flange 235 may be configured to vary around the circumference of the peri-pharyngeal bowl. In one alternative as in the embodiment illustrated the depth of the resiliently deformable flange 235 is greatest at the proximal end of the peri-pharyngeal bowl 218 and gradually reduces as it moves towards the distal end of the peri-pharyngeal bowl 218. In another alternative the depth of the resiliently deformable flange 235 may be substantially uniform around the circumference of the peri-pharyngeal bowl 218.

The circumferential edge 222 of the peri-pharyngeal bowl 218 is preferably rounded or curved such that is it blunt and does not have any squared edges in such a way that whilst it is able to maintain the seal, the circumferential edge 222 does not cause excessive mucosal pressures thus avoiding any trauma to the delicate structures. The circumferential lip 227 is also preferably rounded or curved such that is it blunt and does not have any squared edges in such a way that it does not cause excessive mucosal pressures thus avoiding any trauma to the delicate structures The airway device 210 is formed from a single shot of plastics material over moulded around the connector 224. Preferably the plastics material is of 10 to 90 Shore Hardness on the A scale. In the case of a device for guinea pigs for example the device will be formed from a plastics material of typically 20 to 70 Shore Hardness on the A scale. In the case of a device for rabbits for example the device will be formed from a plastics material of typically 35 to 70 Shore Hardness on the A scale. In the case of a device for cats and/or dogs for example the device will be formed from a plastics material of typically 20 to 60 Shore Hardness on the A scale. In the case of a device for horses for example the device will be formed from a plastics material of typically 20 to 60 Shore Hardness on the A scale. In the case of a device for humans the device will be formed from a plastics material of typically 20 to 50 Shore Hardness on the A scale, preferably less than 50 Shore Hardness on the A scale, preferably less than 40 Shore Hardness on the A scale, preferably 30 to 35 Shore Hardness on the A scale.

The connector 224 may be formed from a material which loses its structure and/or rigidity when exposed to water. In one alternative the connector 224 may be formed from a material that swells when exposed to water such as starch or cellulose. In another alternative the connector 224 may be formed from a material that becomes flexible or collapses or dissolves when exposed to water such as polyvinyl alcohol.

In an alternative the connector 224 may be formed from a standard plastics material whose structure is not impacted on exposure to water such as polycarbonate, polyurethane, polypropylene or polyvinylchloride.

In addition, as illustrated in FIGS. 24 to 27 the connector 224 is provided with a tube within a tube arrangement wherein the inner tube 290 corresponds to the diameter of the airway tube 212 and the outer tube 292 corresponds with the diameter required to connect to the to the relevant gas supply wherein one or more spigots 294 are provided to connect the inner tube 290 to the outer tube 292. In this arrangement when the connector 224 is over moulded the plastics material fills the void between the inner and outer tubes 290, 292 and over and around the one of more spigots 294 which prevents the removal of the connector 224 from the airway tube 212 of the airway device 210 without also destroying the airway tube 212 of the airway device 210. In an alternative loops or rings may be provided on the external surface of the connector as illustrated in respect of the first embodiment of the invention which when over moulded prevents the removal of the connector 224 from the airway tube 212 of the airway device 210 without also destroying the airway tube 212 of the airway device 210. In one alternative the connector is a reduced or low dead space connector.

The airway device 210 is optionally also further provided with a plurality of ribs (not shown) near the proximal end 216 of the airway tube 212 near to the connector 224. The ribs provide a friction point for tying the device around an animal's head as it is generally not possible to use tape as in humans due to the animal's fur.

FIGS. 29 to 33 illustrate a fourth embodiment of an airway device 310 according to the present invention. The airway device 310 has an airway tube 312 with a distal end 314 and a proximal end 316. The distal end 314 of the airway tube 312 is provided with a peri-pharyngeal bowl 318. The peri-pharyngeal bowl is pre-formed in shape and is non-inflatable. The peri-pharyngeal bowl 318 has a posterior bowl portion 319 having a back dorsal portion 320 and a side wall 334 extending around and depending from the periphery of the back dorsal portion 320 which creates an internal space 330a. The peri-pharyngeal bowl 318 also has a resiliently deformable flange 335 which extends laterally from the side wall 334 of the back dorsal portion 320 which creates an extended internal space 330b. The resiliently deformable flange 335 has an inner and an outer surface that extend to a circumferential edge 322 which may be provided with a circumferential lip 327. The peri-pharyngeal bowl 318 is generally ovoid in shape.

In the embodiment illustrated the circumferential lip 327 is formed by providing the circumferential edge 322 with a bend towards to the outer surface of the circumferential edge 322, preferably the bend is 70° to 90°. Alternatively, the circumferential lip 327 may be a separate component connected to the outer surface of the circumferential edge 322.

The proximal end 316 of the airway tube 312 is fitted with a connector 324 such that the proximal end 316 of the airway tube 312 can be connected to the relevant gas supply.

The airway device 310 also optionally has a shoulder 326. The shoulder 326 is used to prevent over-insertion of the airway device 310, and to provide a visual confirmation of insertion depth. The shoulder 326 if present is located laterally or perpendicular to the direction of the airflow, and thus the airway tube 312. The shoulder 326 is used to create a point of contact between the airway device 310 and the faucial pillars located at the back of the mouth of a human or animal patient. This creates a positive stopping feature that in use prevents the shoulder 326 going forward beyond the faucial pillars of the patient to prevent over-insertion of the airway device 310.

The internal volume and depth of the peri-pharyngeal bowl 318, i.e. combination of the internal space 330a and extended internal space 330b together referred to as the combined internal space 330, has been increased compared to that found in the laryngeal cuffs of prior art devices. Previously it was thought that the best way to prevent the epiglottis from occluding the airway was to provide a location external to the laryngeal cuff upon which the epiglottis could rest. This may have been through the use of something extending above and across the opening of the airway in the form of an epiglottic rest for example. It has now been discovered, in particular in devices for use particularly in small animals and paediatric humans, that contrary to the teaching of prior art devices, it is better instead to provide a peri-pharyngeal bowl 318 with a large combined internal space 330, which is configured to contain the body of the larynx of the patient. The combined internal space 330 is configured to not only contain the body of the larynx, but also to be sufficiently sized such that once the body of the larynx has been contained therein that there is still sufficient space in the combined internal space 330 for gases to freely flow to and from the patient without being impeded by the body of the larynx. Preferably the combined internal space 330 contains 50% to 100% of the body of the larynx of the human or animal patient, and more typically 70% to 90% of the body of the larynx of the human or animal patient. In addition, the combined internal space 330 is also configured to contain the body of the larynx of the patient, the body of the larynx should be able to be contained within the combined internal space 330 without any contact being made with any part of the peri-pharyngeal bowl 318 once the airway device 310 is in situ, in particular no contact should be made with the circumferential edge 322, resiliently deformable flange 335 or side wall 334 of the posterior bowl portion 319 of peri-pharyngeal bowl 318. Preferably in this case the whole of the body of the larynx is contained within the combined internal space 330.

In order to achieve a sufficiently large enough combined internal space 330 to accomplish the above, not only has the depth of the peri-pharyngeal bowl been increased, but the sides of the peri-pharyngeal bowl 318 in the form of the resiliently deformable flange 335 extending from the side wall 334 posterior bowl portion 319 has also been reduced in thickness compared to the teaching of prior art laryngeal cuff devices, which taught that thick padded walls were required in order to provide the required sealing levels. Ideally the thickness of the resiliently deformable flange 335 is about 1% to 15% of the external width of the peri-pharyngeal bowl at its widest point In addition to creating a large combined internal space 330, the fact that the resiliently deformable flange 335 is much thinner means that it is more flexible and can be readily deformed when required. In particular, the fact that the peri-pharyngeal bowl 318 is readily deformable means that the peri-pharyngeal bowl 318 can be made larger overall than other pre-formed non-inflatable laryngeal cuff prior art devices as the peri-pharyngeal bowl 318 can be readily deformed to pass through structures, such as the faucial pillars, which in the past have led to a reduced size laryngeal cuff in prior art devices. As the peri-pharyngeal bowl 318 comes into contact with the faucial pillars, the resiliently deformable flange 335 deforms inwards allowing the peri-pharyngeal bowl to pass through and beyond the faucial pillars. After the peri-pharyngeal bowl 318 has passed beyond the faucial pillars, the resiliently deformable flange 335, and thus the peri-pharyngeal bowl 318 regain their original shapes. As the dimensions of the peri-pharyngeal bowl 318 are larger than seen in non-inflatable laryngeal cuff prior arts devices a more effective seal is created, which allows for higher sealing pressures which are required for IPPV especially in larger human or animal patients. The seal that is created is an impaction seal.

When pressure is applied to the peri-pharyngeal bowl 318 either from the direction of the back dorsal portion 320 or the circumferential edge 322 of resiliently deformable flange 335, the force is directed through the peri-pharyngeal bowl 318 to the resiliently deformable flange 335, wherein the resiliently deformable flange 335 is configured to bend with the force in order to create a seal between the circumferential edge 322 thereof and the peri-larynx, i.e. the area around the larynx and not the larynx itself as was the case in prior art devices. Given that the circumferential edge 322 of the resiliently deformable flange 335 has a small contact area to form a seal in comparison to the prior art pad style airway devices, less force is required to be applied to the airway device 310 in order for the seal to form.

The thickness of the sides of the peri-pharyngeal bowl 318 in general may be uniform, however, in the embodiment illustrated the thickness is configured to vary from the side walls 334 of the posterior bowl portion 319 of the peri-pharyngeal bowl 318 to the circumferential edge 322 of the resiliently deformable flange 335 of the peri-pharyngeal bowl 318. In the embodiment illustrated the thickness of the sides is greatest in the side walls 334 of the posterior bowl portion 319 of the peri-pharyngeal bowl 318 and gradually reduces as it moves towards the start of the resiliently deformable flange 335 wherein the thickness is then generally uniform up to the circumferential edge 322. The thickness of the sides may be graduated, or it may be stepped.

The side wall 334 is configured to extend substantially around the entire circumference of the peri-pharyngeal bowl 318. The depth of the side wall 334 may be configured to vary around the circumference of the peri-pharyngeal bowl. In one alternative the depth of the side wall 334 is greatest at the proximal end of the peri-pharyngeal bowl 318 and gradually reduces as it moves towards the distal end of the peri-pharyngeal bowl 318. In another alternative the depth of the side wall 334 may be substantially uniform around the circumference of the peri-pharyngeal bowl 318.

The peri-pharyngeal bowl 318 is provided with a tip 332 at the distal end of the peri-pharyngeal bowl 318. The tip 332 of the peri-pharyngeal bowl 318 is configured to wedge anatomically correctly into the upper oesophagus region of the human or animal patient. In addition, tip 332 is optionally provided with one or more annular sealing rings (not shown) for improved sealing of the tip 332 of the peri-pharyngeal bowl 318 in the upper oesophagus region of the patient. The tip 332 is configured in such a way to optimize the secondary seal at the upper oesophagus such that excess ventilation does not pass beyond which could otherwise result in gastric insufflation and distension; which could otherwise lead to reflux of the gastric contents into the peri-laryngeal bowl 318 of the device.

The resiliently deformable flange 335 is configured to extend substantially around the entire circumference of the peri-pharyngeal bowl 318. The depth of the resiliently deformable flange 335 may be configured to vary around the circumference of the peri-pharyngeal bowl. In one alternative as in the embodiment illustrated the depth of the resiliently deformable flange 335 is greatest at the proximal end of the peri-pharyngeal bowl 318 and gradually reduces as it moves towards the distal end of the peri-pharyngeal bowl 318. In another alternative the depth of the resiliently deformable flange 335 may be substantially uniform around the circumference of the peri-pharyngeal bowl 318.

The circumferential edge 322 of the peri-pharyngeal bowl 318 is preferably rounded or curved such that is it blunt and does not have any squared edges in such a way that whilst it is able to maintain the seal, the circumferential edge 322 does not cause excessive mucosal pressures thus avoiding any trauma to the delicate structures. The circumferential lip 327 is also preferably rounded or curved such that is it blunt and does not have any squared edges in such a way that it does not cause excessive mucosal pressures thus avoiding any trauma to the delicate structures The airway device 310 is formed from a single shot of plastics material over moulded around the connector 324. Preferably the plastics material is of 10 to 90 Shore Hardness on the A scale. In the case of a device for guinea pigs for example the device will be formed from a plastics material of typically 20 to 70 Shore Hardness on the A scale. In the case of a device for rabbits for example the device will be formed from a plastics material of typically 35 to 70 Shore Hardness on the A scale. In the case of a device for cats and/or dogs for example the device will be formed from a plastics material of typically 20 to 60 Shore Hardness on the A scale. In the case of a device for horses for example the device will be formed from a plastics material of typically 20 to 60 Shore Hardness on the A scale. In the case of a device for humans the device will be formed from a plastics material of typically 20 to 50 Shore Hardness on the A scale, preferably less than 50 Shore Hardness on the A scale, preferably less than 40 Shore Hardness on the A scale, preferably 30 to 35 Shore Hardness on the A scale.

The connector 324 may be formed from a material which loses its structure and/or rigidity when exposed to water. In one alternative the connector 324 may be formed from a material that swells when exposed to water such as starch or cellulose. In another alternative the connector 324 may be formed from a material that becomes flexible or collapses or dissolves when exposed to water such as polyvinyl alcohol.

In an alternative the connector 324 may be formed from a standard plastics material whose structure is not impacted on exposure to water such as polycarbonate, polyurethane, polypropylene or polyvinylchloride.

In addition, as illustrated in FIGS. 34 to 38 the connector 324 is optionally provided with loops or rings 380 which when over moulded prevents the removal of the connector from the airway tube of the device without also destroying the airway tube of the device. In an alternative not illustrated the connector 324 is optionally provided with a tube within a tube arrangement wherein the inner tube corresponds to the diameter of the airway tube 312 and the outer tube corresponds with the diameter required to connect to the to the relevant gas supply wherein one or more spigots are provided to connect the inner tube to the outer tube. In this arrangement when the connector 324 is over moulded the plastics material fills the void between the inner and outer tubes and over and around the one of more spigots which prevents the removal of the connector 324 from the airway tube 312 of the airway device 310 without also destroying the airway tube 312 of the airway device 310. In one alternative the connector is a reduced or low dead space connector.

The airway device 310 is optionally also further provided with a plurality of ribs 360 near the proximal end 316 of the airway tube 312 near to the connector 324. The ribs 360 provide a friction point for tying the airway device 310 around an animal's head as it is generally not possible to use tape as in humans due to the animal's fur.

The back dorsal portion 320 of the posterior bowl portion 319 or the peri-pharyngeal bowl 218 is optionally flattened with gently squared corners 323. This squared rather than curved feature prevents the peri-pharyngeal bowl 318 from rocking when in situ in the human or animal patient and therefore gives greater stability to the airway device 310 when it is in situ in the human or animal patient.

The airway device 310 is optionally provided with an oesophageal gastric channel 382 extending along the length of the device exiting through tip 332 of peri-pharyngeal bowl 318. In typical prior art devices, the gastric channel entry point at the distal end of the device is a round hole. The clinician would then feed a gastric tube or the like into this hole for it to then pass down the channel into the stomach of the patient in order to decompress the stomach of gastric fluids and gases. It can sometimes be challenging to get the small round gastric tube into the small round opening of the gastric channel, as the gastric tube is itself flexible and will bend if not inserted exactly. In the present invention in order to overcome this problem, the distal end of the gastric channel is provided with a graduated oval entry point 384 rather than a circular entry point, as if the distal end of the channel had been cut at an angle. This gives a greater sized opening and a ramp to guide the gastric tube down into the gastric channel 382.

In this embodiment the airway tube 312 is oval rather than cylindrical, however, the connection to the breathing machine is cylindrical. Therefore, an adaptor 370 is provided to "reduce" the diameter of airway tube 312 at its proximal end 314 from the oval shape to a circle into which a standard 15 mm connector can be fitted. The proximal end 316 of the airway tube is then fitted with a standard 15 mm connector such that the proximal end 316 of the airway tube 312 can be connected to the relevant gas supply.

FIGS. 39 to 43 are provided to illustrate and provide understanding of the anatomy of the upper airway of a dog and in particular the functioning of the epiglottis.

Figure 39:
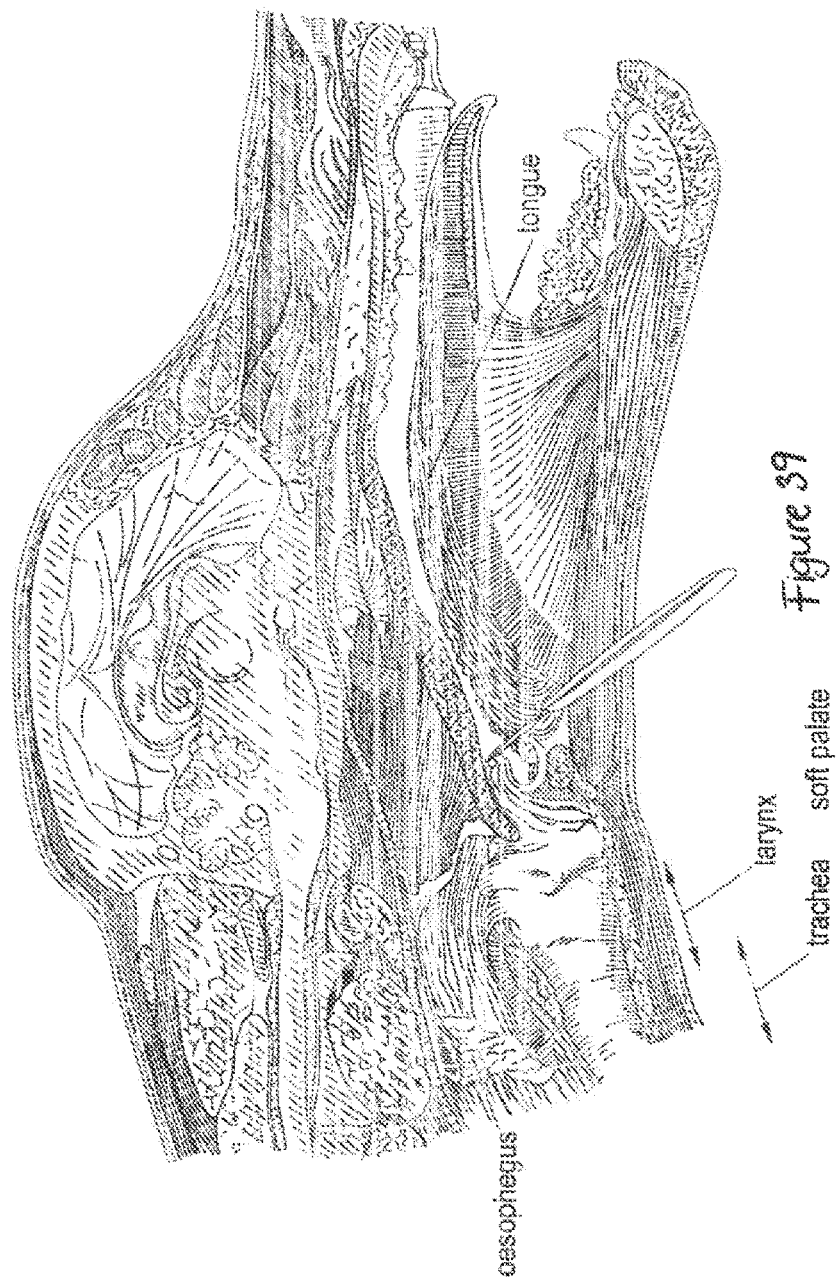
FIG. 39 is a cross-sectional view of the upper airway of a dog.

FIG. 39 illustrates the cross-sectional view of the upper airway of a dog. The larynx, trachea and epiglottis form one complete structure. It can be seen that the soft palate is sitting against the epiglottis, which would be the normal position if the dog were breathing through its nose. When a dog is panting, this means that it is breathing through both its mouth and its nose, in this scenario the soft palate would move away from the epiglottis to open up the larynx for air flow by both channels.

Figure 40:
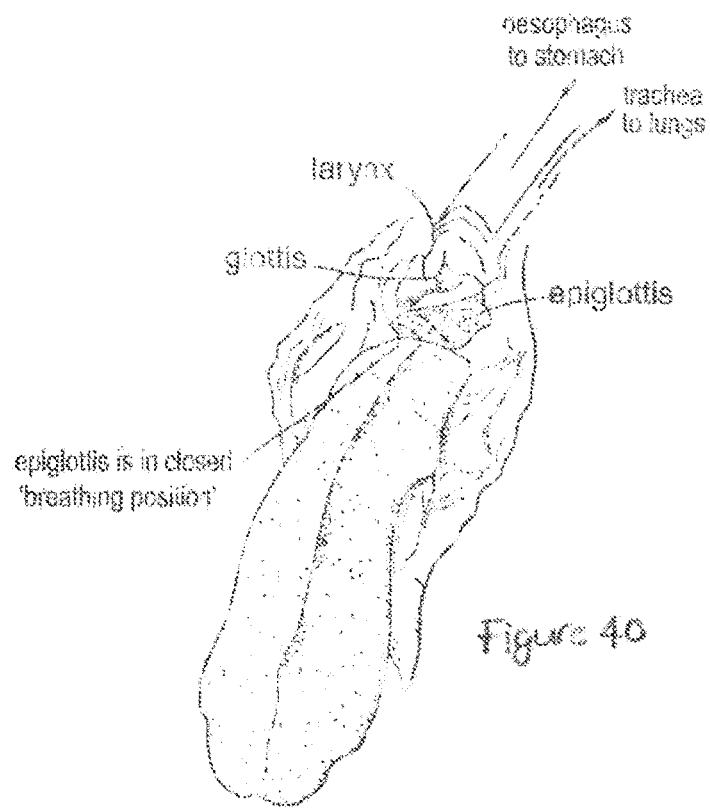
FIGS. 40 and 41 are perspective views of the upper airway of a dog.
Figure 41:
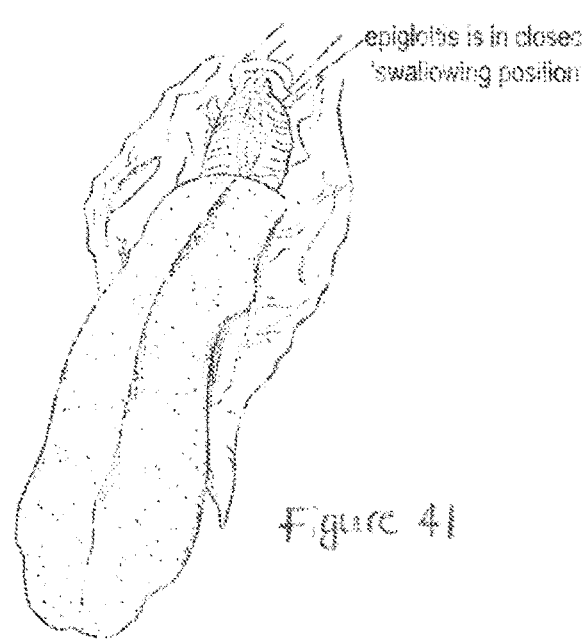
Figures 2, 4:
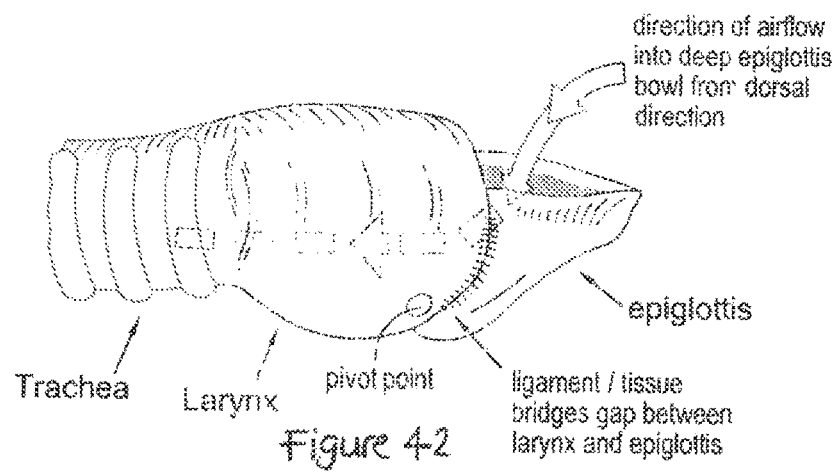
FIG. 2 is a bottom (ventral) view of an airway device according to a first embodiment of the present invention.
FIG. 4 is a side cross-sectional view through B-B of FIG. 2.

FIGS. 40 and 41 illustrate perspective views of the upper airway of a dog. FIG. 40 illustrates the upper airway when the epiglottis is in the open position for breathing. The epiglottis is in the form of a deep bowl with pronounced lateral sides. When the epiglottis is in the open position the larynx can be accessed. FIG. 41 illustrates the upper airway when the epiglottis is in the closed position for swallowing. The epiglottis moves from the open to the closed position by pivoting about the base thereof.

Figure 43:
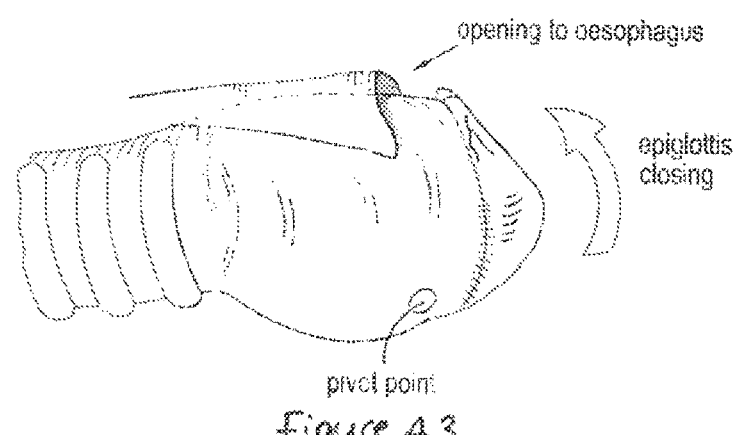

FIGS. 42 and 43 illustrate perspective views of the trachea, larynx and epiglottis assembly. FIG. 42 illustrates the assembly when the epiglottis is in the open position. FIG. 43 illustrates the assembly when the epiglottis is in the closed position. Both of these figures illustrate the point about which the epiglottis pivots as it moves between the open and the closed positions.

Thus, in all breeds of dog, the bowl of the epiglottis in its natural open breathing position sits so that its open face is upwards against the soft palate. When the dog breaths the bowl of the epiglottis and the soft palate disengage to allow the flow of air through the open face of the bowl of the epiglottis down into the larynx. When the dog swallows while awake the epiglottis pivots to fully cover the larynx.

Figure 44:
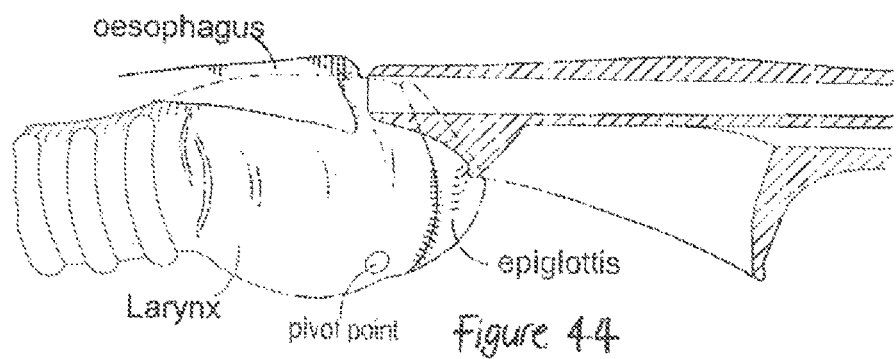
FIGS. 44 to 46 are views illustrating the insertion of an airway device wherein the airway device is shown in cross section, and wherein the anatomical features of the patient are not shown in cross section.
Figure 45:
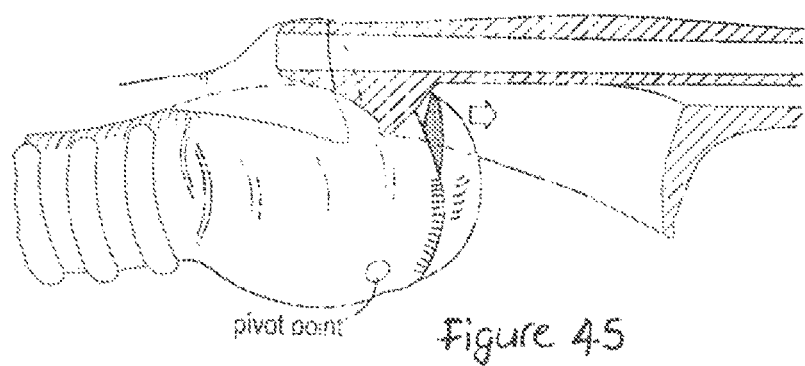
Figure 46:
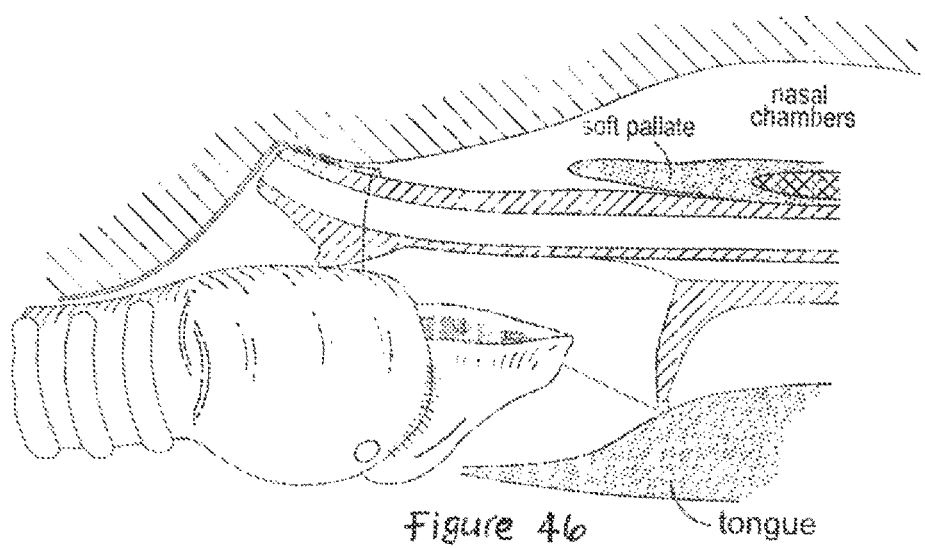

FIGS. 44 to 46 illustrate what happens during the insertion of airway device 310 wherein the airway device is shown in cross section, and wherein the anatomical features of the patient are not shown in cross section.

Figure 47:
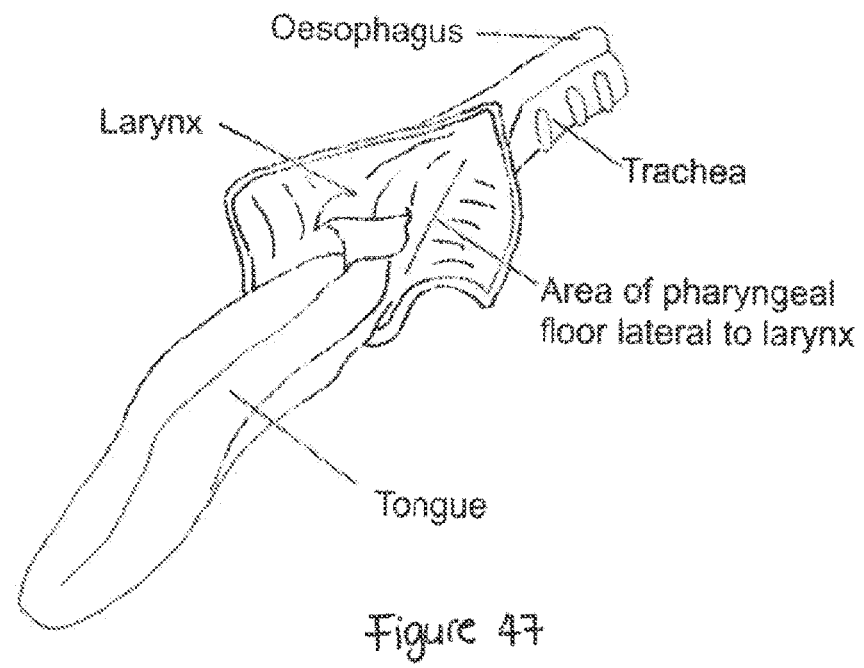
FIGS. 47 to 49 illustrate dorsocranial views of the tongue, pharynx, larynx and oesophagus of a dog.
Figure 48:
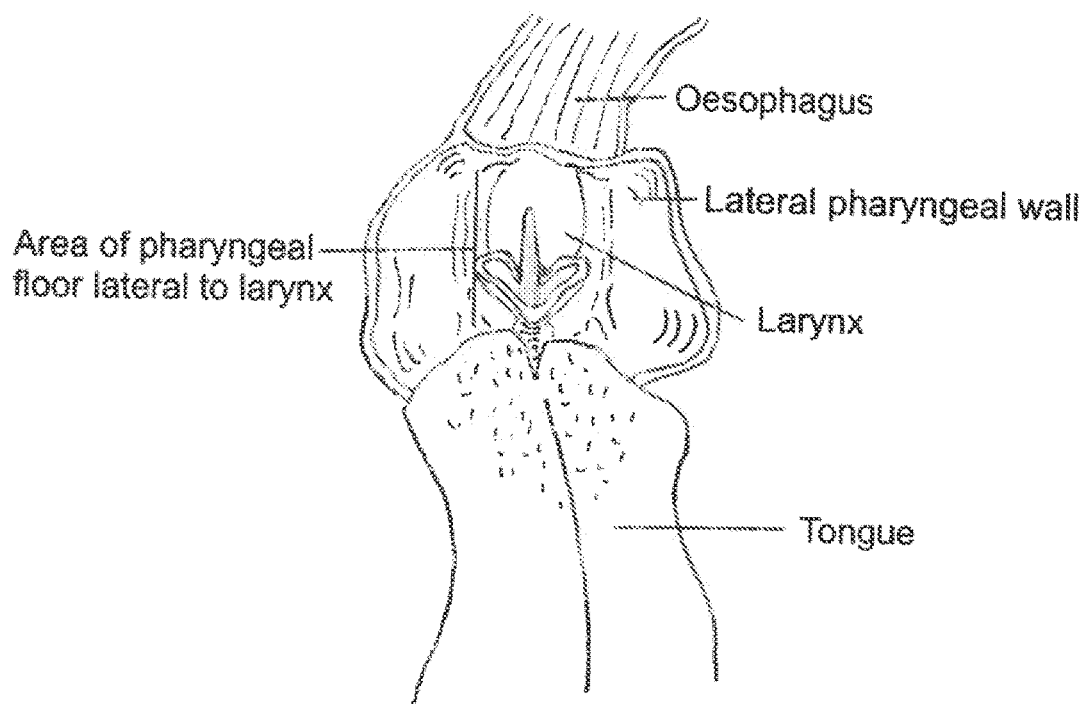
Figure 49:
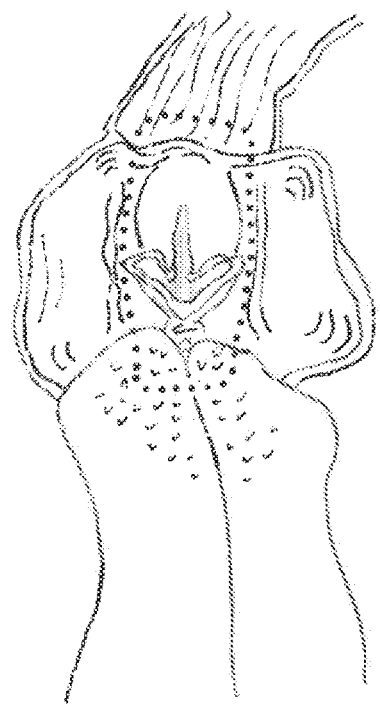
Figure 50:
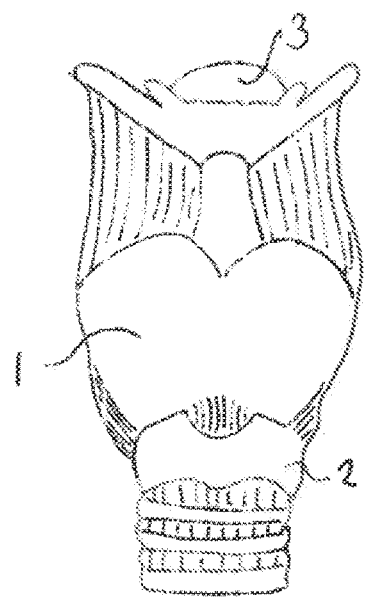
FIG. 50 illustrates an anterior view of an exemplary body of a larynx.
Figure 51:
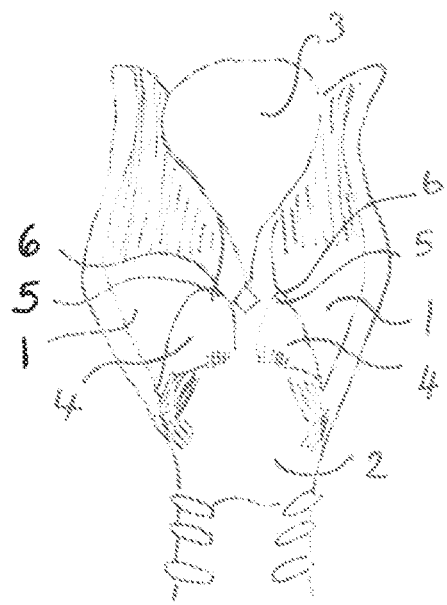
FIG. 51 illustrates a posterior view of an exemplary body of a larynx.
Figure 52:
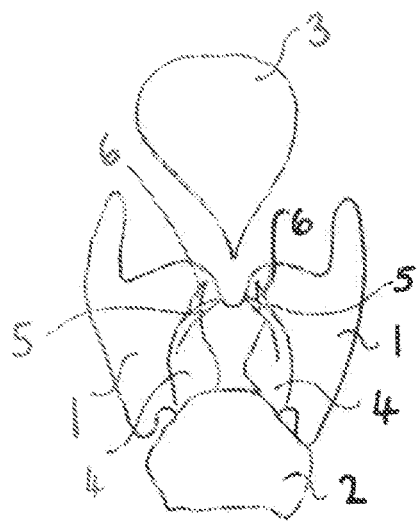
FIG. 52 illustrates a posterior view the cartilages of an exemplary body of a larynx.
Figure 55:
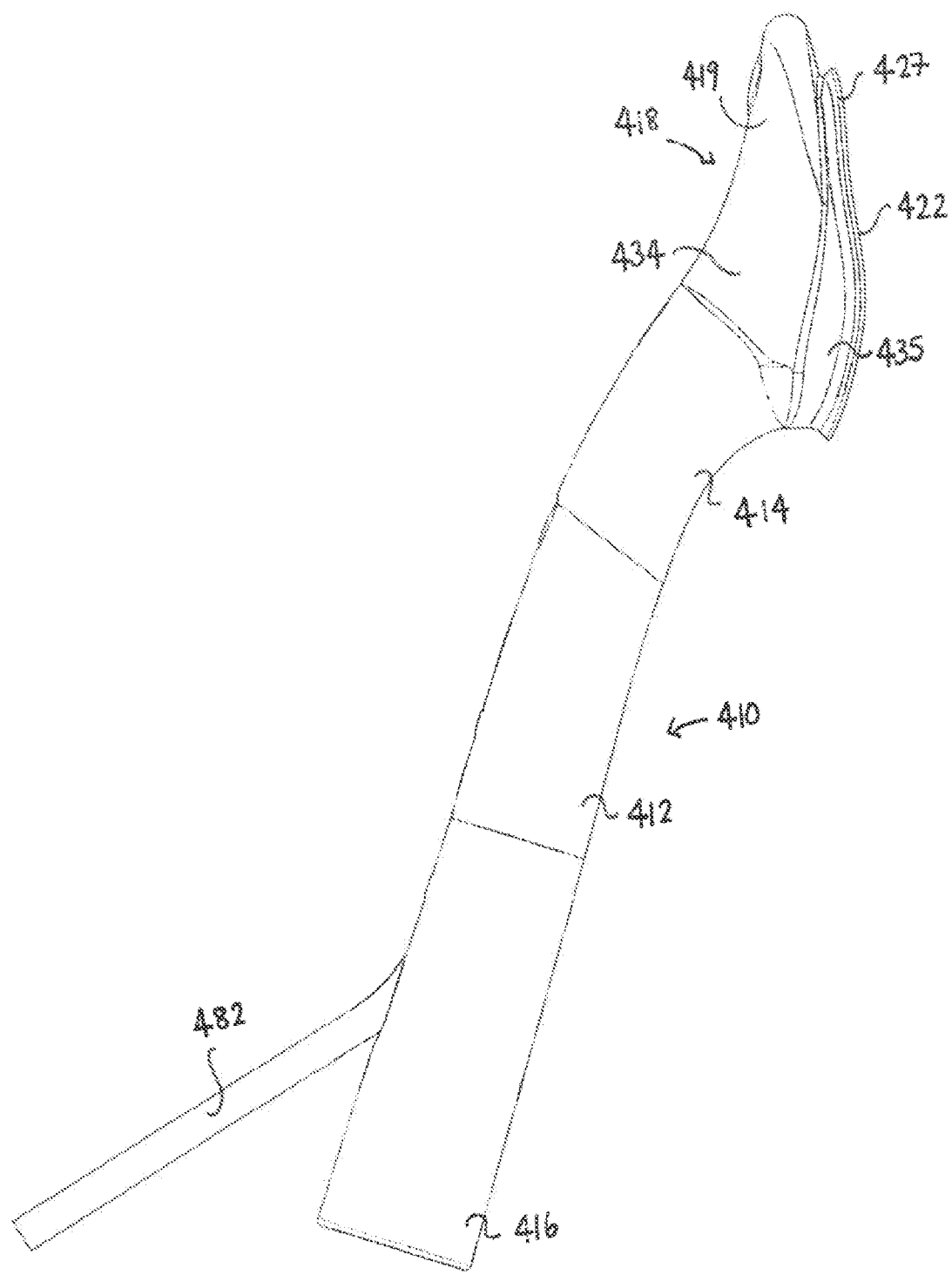
FIG. 55 is a side view of an airway device according to a fifth embodiment of the present invention.
Figure 56:
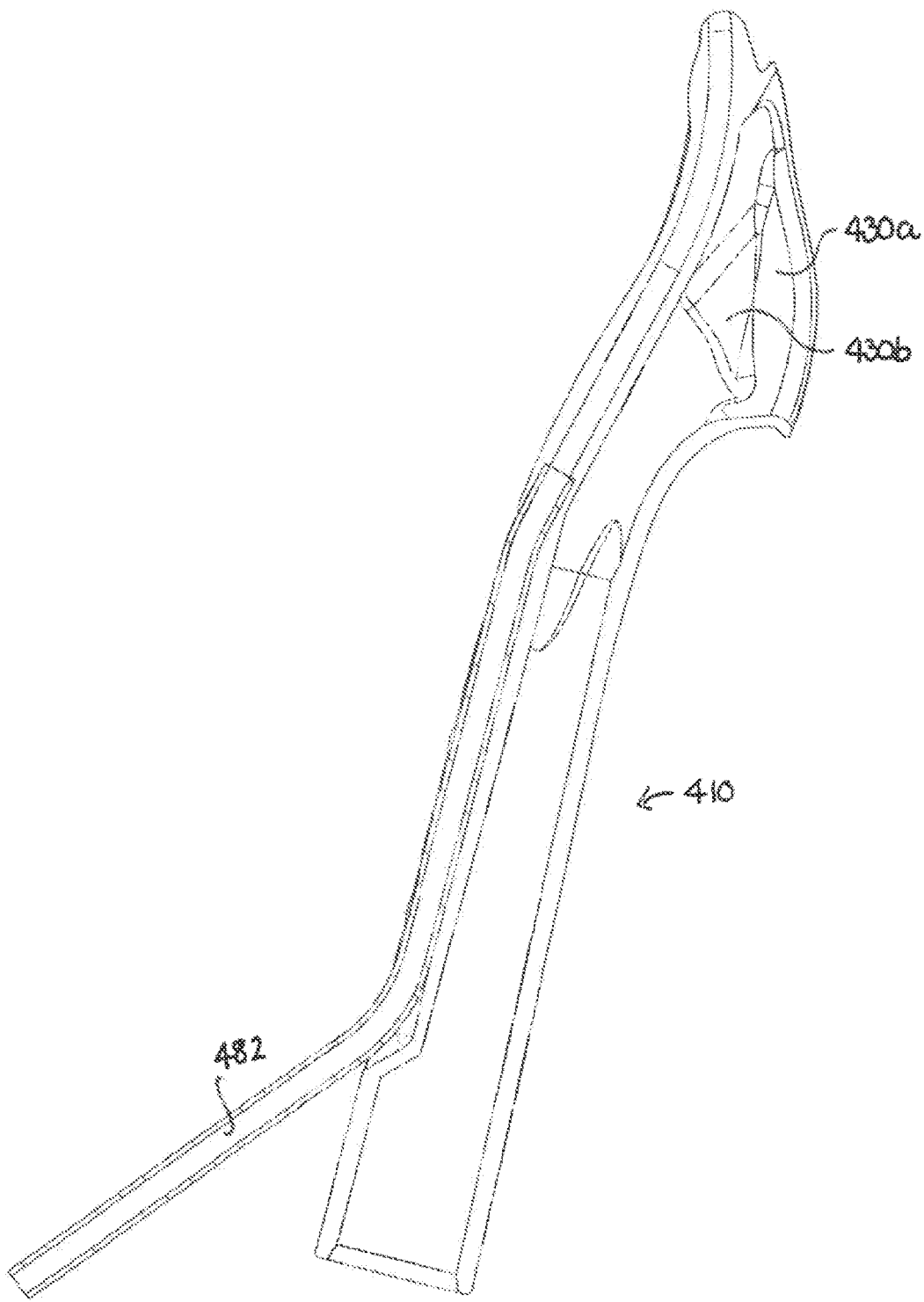
FIG. 56 is a cross-sectional view is a cross-sectional view through B-B of FIG. 54.

FIGS. 47 and 49 illustrate dorsocranial views of the tongue, pharynx, larynx and oesophagus of a dog.

FIGS. 53 to 59 illustrate a fifth embodiment of an airway device 410 according to the present invention. The airway device 410 has an airway tube 412 with a distal end 414 and a proximal end 416. The distal end 414 of the airway tube 412 is provided with a peri-pharyngeal bowl 418. The peri-pharyngeal bowl is pre-formed in shape and is non-inflatable. The peri-pharyngeal bowl 418 has a posterior bowl portion 419 having a back dorsal portion 420 and a side wall 434 extending around and depending from the periphery of the back dorsal portion 420 which creates an internal space 430a. The peri-pharyngeal bowl 418 also has a resiliently deformable flange 435 which extends laterally from the side wall 434 of the back dorsal portion 420 which creates an extended internal space 430b. The resiliently deformable flange 435 has an inner and an outer surface that extend to a circumferential edge 422 which may be provided with a circumferential lip 427. The peri-pharyngeal bowl 418 is generally ovoid in shape.

In the embodiment illustrated the circumferential lip 427 is formed by providing the circumferential edge 422 with a bend towards to the outer surface of the circumferential edge 422, preferably the bend is 70° to 90°. Alternatively, the circumferential lip 427 may be a separate component connected to the outer surface of the circumferential edge 422.

The proximal end 416 of the airway tube 412 may be fitted with a connector (not shown) such that the proximal end 416 of the airway tube 412 can be connected to the relevant gas supply.

The airway device 410 may optionally have a shoulder (not illustrated). The shoulder if present is used to prevent over-insertion of the airway device 410, and to provide a visual confirmation of insertion depth. The shoulder if present is located laterally or perpendicular to the direction of the airflow, and thus the airway tube 412. The shoulder if present is used to create a point of contact between the airway device 410 and the faucial pillars located at the back of the mouth of a human or animal patient. This creates a positive stopping feature that in use prevents the shoulder if present going forward beyond the faucial pillars of the patient to prevent over-insertion of the airway device 410.

The internal volume and depth of the peri-pharyngeal bowl 418, i.e. combination of the internal space 430a and extended internal space 330b together referred to as the combined internal space 430, has been increased compared to that found in the laryngeal cuffs of prior art devices. Previously it was thought that the best way to prevent the epiglottis from occluding the airway was to provide a location external to the laryngeal cuff upon which the epiglottis could rest. This may have been through the use of something extending above and across the opening of the airway in the form of an epiglottic rest for example. It has now been discovered, in particular in devices for use particularly in small animals and paediatric humans, that contrary to the teaching of prior art devices, it is better instead to provide a peri-pharyngeal bowl 418 with a large combined internal space 430, which is configured to contain the body of the larynx of the patient. The combined internal space 430 is configured to not only contain the body of the larynx, but also to be sufficiently sized such that once the body of the larynx has been contained therein that there is still sufficient space in the combined internal space 430 for gases to freely flow to and from the patient without being impeded by the body of the larynx. Preferably the combined internal space 430 contains 50% to 100% of the body of the larynx of the human or animal patient, and more typically 70% to 90% of the body of the larynx of the human or animal patient. In addition, the combined internal space 430 is also configured to contain the body of the larynx of the patient, the body of the larynx should be able to be contained within the combined internal space 430 without any contact being made with any part of the peri-pharyngeal bowl 418 once the airway device 410 is in situ, in particular no contact should be made with the circumferential edge 422, resiliently deformable flange 435 or side wall 434 of the posterior bowl portion 419 of peri-pharyngeal bowl 418. Preferably in this case the whole of the body of the larynx is contained within the combined internal space 430.

In order to achieve a sufficiently large enough combined internal space 430 to accomplish the above, not only has the depth of the peri-pharyngeal bowl been increased, but the sides of the peri-pharyngeal bowl 418 in the form of the resiliently deformable flange 435 extending from the side wall 434 posterior bowl portion 419 has also been reduced in thickness compared to the teaching of prior art laryngeal cuff devices, which taught that thick padded walls were required in order to provide the required sealing levels. Ideally the thickness of the resiliently deformable flange 335 is about 1% to 15% of the external width of the peri-pharyngeal bowl at its widest point In addition to creating a large combined internal space 430, the fact that the resiliently deformable flange 435 is much thinner means that it is more flexible and can be readily deformed when required. In particular, the fact that the peri-pharyngeal bowl 418 is readily deformable means that the peri-pharyngeal bowl 418 can be made larger overall than other pre-formed non-inflatable laryngeal cuff prior art devices as the peri-pharyngeal bowl 418 can be readily deformed to pass through structures, such as the faucial pillars, which in the past have led to a reduced size laryngeal cuff in prior art devices. As the peri-pharyngeal bowl 418 comes into contact with the faucial pillars, the resiliently deformable flange 435 deforms inwards allowing the peri-pharyngeal bowl to pass through and beyond the faucial pillars. After the peri-pharyngeal bowl 318 has passed beyond the faucial pillars, the resiliently deformable flange 335, and thus the peri-pharyngeal bowl 418 regain their original shapes. As the dimensions of the peri-pharyngeal bowl 418 are larger than seen in non-inflatable laryngeal cuff prior arts devices a more effective seal is created, which allows for higher sealing pressures which are required for IPPV especially in larger human or animal patients. The seal that is created is an impaction seal.

When pressure is applied to the peri-pharyngeal bowl 418 either from the direction of the back dorsal portion 420 or the circumferential edge 422 of resiliently deformable flange 435, the force is directed through the peri-pharyngeal bowl 418 to the resiliently deformable flange 435, wherein the resiliently deformable flange 435 is configured to bend with the force in order to create a seal between the circumferential edge 422 thereof and the peri-larynx, i.e. the area around the larynx and not the larynx itself as was the case in prior art devices. Given that the circumferential edge 422 of the resiliently deformable flange 435 has a small contact area to form a seal in comparison to the prior art pad style airway devices, less force is required to be applied to the airway device 410 in order for the seal to form.

The thickness of the sides of the peri-pharyngeal bowl 418 in general may be uniform, however, in the embodiment illustrated the thickness is configured to vary from the side walls 434 of the posterior bowl portion 419 of the peri-pharyngeal bowl 418 to the circumferential edge 422 of the resiliently deformable flange 435 of the peri-pharyngeal bowl 418. In the embodiment illustrated the thickness of the sides is greatest in the side walls 434 of the posterior bowl portion 419 of the peri-pharyngeal bowl 418 and gradually reduces as it moves towards the start of the resiliently deformable flange 435 wherein the thickness is then generally uniform up to the circumferential edge 422. The thickness of the sides may be graduated, or it may be stepped.

The peri-pharyngeal bowl 418 is provided with a tip 432 at the distal end of the peri-pharyngeal bowl 418. The tip 432 of the peri-pharyngeal bowl 418 is configured to wedge anatomically correctly into the upper oesophagus region of the human or animal patient. In addition, tip 432 is optionally provided with one or more annular sealing rings (not shown) for improved sealing of the tip 432 of the peri-pharyngeal bowl 418 in the upper oesophagus region of the patient. The tip 432 is configured in such a way to optimize the secondary seal at the upper oesophagus such that excess ventilation does not pass beyond which could otherwise result in gastric insufflation and distension; which could otherwise lead to reflux of the gastric contents into the peri-laryngeal bowl 418 of the device.

The resiliently deformable flange 435 is configured to extend substantially around the entire circumference of the peri-pharyngeal bowl 418. The depth of the resiliently deformable flange 435 may be configured to vary around the circumference of the peri-pharyngeal bowl. In one alternative as in the embodiment illustrated the depth of the resiliently deformable flange 435 is greatest at the proximal end of the peri-pharyngeal bowl 418 and gradually reduces as it moves towards the distal end of the peri-pharyngeal bowl 418. In another alternative the depth of the resiliently deformable flange 435 may be substantially uniform around the circumference of the peri-pharyngeal bowl 418.

The circumferential edge 422 of the peri-pharyngeal bowl 418 is preferably rounded or curved such that is it blunt and does not have any squared edges in such a way that whilst it is able to maintain the seal, the circumferential edge 422 does not cause excessive mucosal pressures thus avoiding any trauma to the delicate structures. The circumferential lip 427 is also preferably rounded or curved such that is it blunt and does not have any squared edges in such a way that it does not cause excessive mucosal pressures thus avoiding any trauma to the delicate structures The airway device 410 is formed from a single shot of plastics material which may be moulded around a connector if provided. Preferably the plastics material is of 10 to 90 Shore Hardness on the A scale. In the case of a device for guinea pigs for example the device will be formed from a plastics material of typically 20 to 70 Shore Hardness on the A scale. In the case of a device for rabbits for example the device will be formed from a plastics material of typically 35 to 70 Shore Hardness on the A scale. In the case of a device for cats and/or dogs for example the device will be formed from a plastics material of typically 20 to 60 Shore Hardness on the A scale. In the case of a device for horses for example the device will be formed from a plastics material of typically 20 to 60 Shore Hardness on the A scale. In the case of a device for humans the device will be formed from a plastics material of typically 20 to 50 Shore Hardness on the A scale, preferably less than 50 Shore Hardness on the A scale, preferably less than 40 Shore Hardness on the A scale, preferably 30 to 35 Shore Hardness on the A scale.

The connector may be formed from a material which loses its structure and/or rigidity when exposed to water. In one alternative the connector may be formed from a material that swells when exposed to water such as starch or cellulose. In another alternative the connector may be formed from a material that becomes flexible or collapses or dissolves when exposed to water such as polyvinyl alcohol.

In an alternative the connector may be formed from a standard plastics material whose structure is not impacted on exposure to water such as polycarbonate, polyurethane, polypropylene or polyvinylchloride.

The connector is optionally provided with loops or rings or other member which when over moulded prevents the removal of the connector from the airway tube of the device without also destroying the airway tube of the device. In an alternative the connector is optionally provided with a tube within a tube arrangement wherein the inner tube corresponds to the diameter of the airway tube 412 and the outer tube corresponds with the diameter required to connect to the to the relevant gas supply wherein one or more spigots are provided to connect the inner tube to the outer tube. In this arrangement when the connector is over moulded the plastics material fills the void between the inner and outer tubes and over and around the one of more spigots which prevents the removal of the connector from the airway tube 412 of the airway device 410 without also destroying the airway tube 412 of the airway device 410. In one alternative the connector is a reduced or low dead space connector.

The airway device 410 is optionally also further provided with a plurality of ribs (not shown) near the proximal end 416 of the airway tube 412. The ribs 360 provide a friction point for tying the airway device 410 around an animal's head as it is generally not possible to use tape as in humans due to the animal's fur.

The airway device 410 is optionally provided with an oesophageal gastric channel 482 extending along the length of the device exiting through tip 432 of peri-pharyngeal bowl 418.

The invention claimed is:

1. An airway device for human or animal use, the device comprising an airway tube having a distal end and a proximal end, the distal end of the airway tube is provided with a pre-formed and non-inflatable peri-pharyngeal bowl, the peri-pharyngeal bowl comprising a posterior bowl portion having a back dorsal portion and a side wall extending around and depending from the periphery of the back dorsal portion to define an internal space, the peri-pharyngeal bowl further comprising a resiliently deformable flange extending lateral and perpendicular to the side wall of the back dorsal portion which defines an extended internal space, the resiliently deformable flange having inner and outer surfaces that extend to a circumferential edge wherein the circumferential edge is provided with a circumferential lip and wherein the resiliently deformable flange is configured to extend substantially around the entire circumference of the peri-pharyngeal bowl and wherein the resiliently deformable flange is configured to form a seal with the peri-larynx in the hypopharynx within and against the mucosa of the pharyngeal and hypo-pharyngeal walls of the human or animal patient by enveloping the glottis within the peri-pharyngeal bowl when in situ in a human or animal patient and wherein the internal space and the extended internal space together comprises a combined internal space and wherein the combined internal space is configured to contain and envelope 50% to 100% of the body of the larynx of the human or animal patient without making contact therewith once the airway device is in situ in a human or animal patient.

2. The airway device as claimed in claim 1 wherein the circumferential edge is rounded or curved such that it is blunt and does not have any square edges.

3. The airway device as claimed in claim 1 wherein the circumferential lip is rounded or curved such that it is blunt and does not have any square edges.

4. The airway device as claimed in claim 1 wherein the circumferential lip is formed by providing the circumferential edge with a bend towards to the outer surface of the resiliently deformable flange.

5. The airway device as claimed in claim 4 wherein the bend is 70° to 90°.

6. The airway device as claimed in claim 1 wherein the circumferential lip is the same depth and thickness as the thickness of the resiliently deformable flange.

7. The airway device as claimed in claim 1 wherein the resiliently deformable flange forms a generally ovoid shape.

8. The airway device as claimed in claim 1 wherein the resiliently deformable flange splays outwardly upon application of a force.

9. The airway device as claimed in claim 1 wherein the resiliently deformable flange splays outwardly upon application of a force when in situ in a human or animal patient.

10. The airway device as claimed in claim 1 wherein the resiliently deformable flange is configured to form a substantially continuous ovoid seal with the flattest areas of the mucosa to the front, back and sides of the body of the larynx.

11. The airway device as claimed in claim 1 wherein the circumferential edge of the resiliently deformable flange forms the seal.

12. The airway device as claimed in claim 1 wherein the circumferential lip of the circumferential edge forms the seal.

13. The airway device as claimed in claim 1 wherein the depth of the resiliently deformable flange is configured to vary around the circumference of the peri-pharyngeal bowl.

14. The airway device as claimed in claim 1 wherein the thickness of the resiliently deformable flange of the peri-pharyngeal bowl is about 1% to 15% of the external width of the peri-pharyngeal bowl at its widest point.

15. The airway device as claimed in claim 1 wherein the thickness of the back dorsal portion of the peri-pharyngeal bowl is between about 1 mm to about 15 mm, the thickness of the side wall is between about 0.5 mm to about 10 mm, and the thickness of the resiliently deformable flange is between about 0.5 mm to about 5 mm.

16. The airway device as claimed in claim 1 wherein the peri-pharyngeal bowl is provided with a tip at the distal end of the peri-pharyngeal bowl configured to wedge into the upper oesophagus region of the human or animal.

17. The airway device as claimed in claim 1 wherein the exterior of the posterior bowl portion is provided with rounded square corners between the exterior of the back dorsal portion and the side walls of the posterior bowl.

18. The airway device as claimed in claim 1 wherein the exterior of the posterior bowl portion is provided with a flattened back dorsal portion.

19. The airway device as claimed in claim 1 wherein the airway device is further provided with a gastric tube passageway.

20. The airway device as claimed in claim 1 wherein the device is further provided with a connector for connecting the device to a gas supply.

21. The airway device as claimed in claim 20 wherein the connector is formed from a material which loses its structure and/or rigidity when exposed to water.

22. A method of making an airway device as claimed in claim 20 wherein the device is formed from a single shot of plastics material over moulded around the connector.

23. The method as claimed in claim 22 wherein the plastics material is of 10 to 90 Shore Hardness on the A scale.

24. The method as claimed in claim 22 wherein the connector is provided with a loop, ring or other member which when over moulded prevents the removal of the connector from the airway tube of the device without also destroying the airway tube of the device.

* * * * *